United States Patent
Flores et al.

(10) Patent No.: US 10,815,236 B2
(45) Date of Patent: Oct. 27, 2020

(54) SEMICONDUCTING POLYMER

(71) Applicant: BASF SE, Ludwigshafen am Rhein (DE)

(72) Inventors: Jean-Charles Flores, Basel (CH); Pascal Hayoz, Basel (CH); Iain McCulloch, Eastleigh (GB); Nkechinyerem Onwubiko, London (GB); Daniel Kaelblein, Ludwigshafen (DE); Wan Yue, Guangzhou (CN); Hung-Yang Chen, Somerset, NJ (US); Astrid-Caroline Knall, London (GB)

(*) Notice: Subject to any disclaimer, the term of this patent is extended or adjusted under 35 U.S.C. 154(b) by 0 days.

(21) Appl. No.: 16/080,166

(22) PCT Filed: Feb. 27, 2017

(86) PCT No.: PCT/EP2017/054507
§ 371 (c)(1),
(2) Date: Aug. 27, 2018

(87) PCT Pub. No.: WO2017/148864
PCT Pub. Date: Sep. 8, 2017

(65) Prior Publication Data
US 2019/0048015 A1    Feb. 14, 2019

(30) Foreign Application Priority Data

Feb. 29, 2016 (EP) ..................... 16157844
Dec. 29, 2016 (EP) ..................... 16207316

(51) Int. Cl.
C07D 487/04    (2006.01)
C09B 57/00     (2006.01)
(Continued)

(52) U.S. Cl.
CPC ............ *C07D 487/04* (2013.01); *C09B 57/00* (2013.01); *C09B 57/004* (2013.01);
(Continued)

(58) Field of Classification Search
CPC .... C08G 2261/3243; C08G 2261/3246; C08G 61/126; C08G 2261/414; C08G 2261/91;
(Continued)

(56) References Cited

U.S. PATENT DOCUMENTS

2010/0297405 A1    11/2010  Flores et al.
2015/0295179 A1    10/2015  Li
(Continued)

FOREIGN PATENT DOCUMENTS

WO    WO 2009/053291 A1    4/2009
WO    WO 2014/071524 A1    5/2014
(Continued)

OTHER PUBLICATIONS

International Search Report dated Apr. 4, 2017 in PCT/EP2017/054507 filed Feb. 27, 2017.

*Primary Examiner* — Shane Fang
(74) *Attorney, Agent, or Firm* — Oblon, McClelland, Maier & Neustadt, L.L.P.

(57) ABSTRACT

Compounds of formula (I) and polymers comprising at least a structure of formula (II), wherein $T^1$ or $T^2$ are indepen-
(Continued)

IDrain, IGate vs V Gate-Source dently of each other a group of Formula (III), Formula (iv) $Q^a$, $Q^b$, $Q^c$, $Q^d$, $Q^e$ or $Q^f$ are independently of each other O, S or $NR^1$.

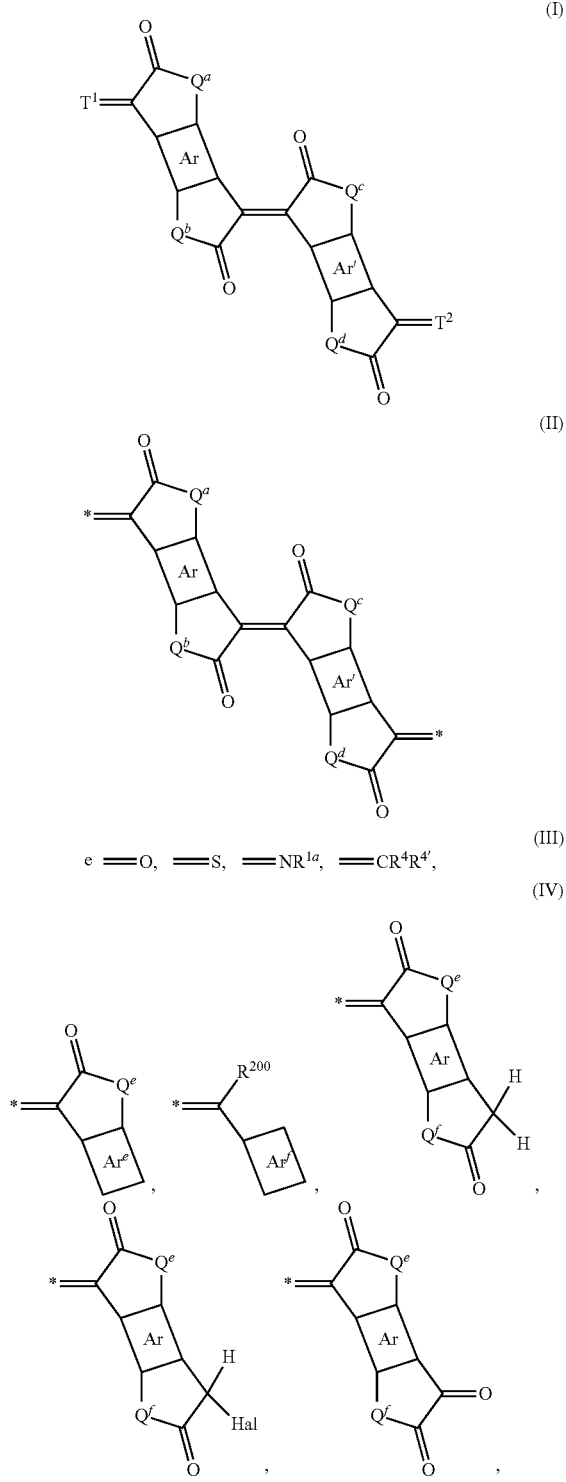

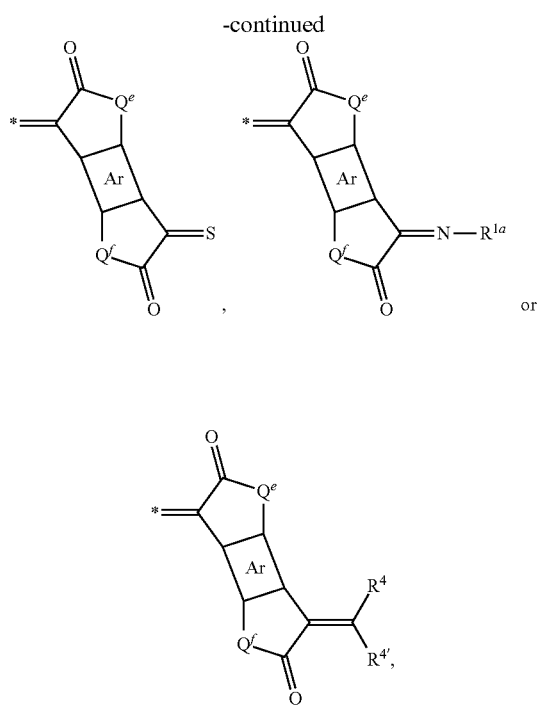

13 Claims, 1 Drawing Sheet

(51) Int. Cl.
  *C09B 69/10* (2006.01)
  *H01L 51/00* (2006.01)
  *H01L 51/05* (2006.01)

(52) U.S. Cl.
  CPC ........ *C09B 69/109* (2013.01); *H01L 51/0034* (2013.01); *H01L 51/0508* (2013.01); *C08G 2261/3223* (2013.01)

(58) Field of Classification Search
  CPC .............. C07D 417/14; H01L 51/0043; H01L 51/0036; H01L 51/0047; H01L 51/4253; Y02E 10/549
  See application file for complete search history.

(56) References Cited

U.S. PATENT DOCUMENTS

2016/0362517 A1  12/2016  He et al.
2016/0365518 A1  12/2016  He et al.

FOREIGN PATENT DOCUMENTS

WO   WO 2015/130915 A1   9/2015
WO   WO 2015/139602 A1   9/2015
WO   WO 2016/005891 A1   1/2016

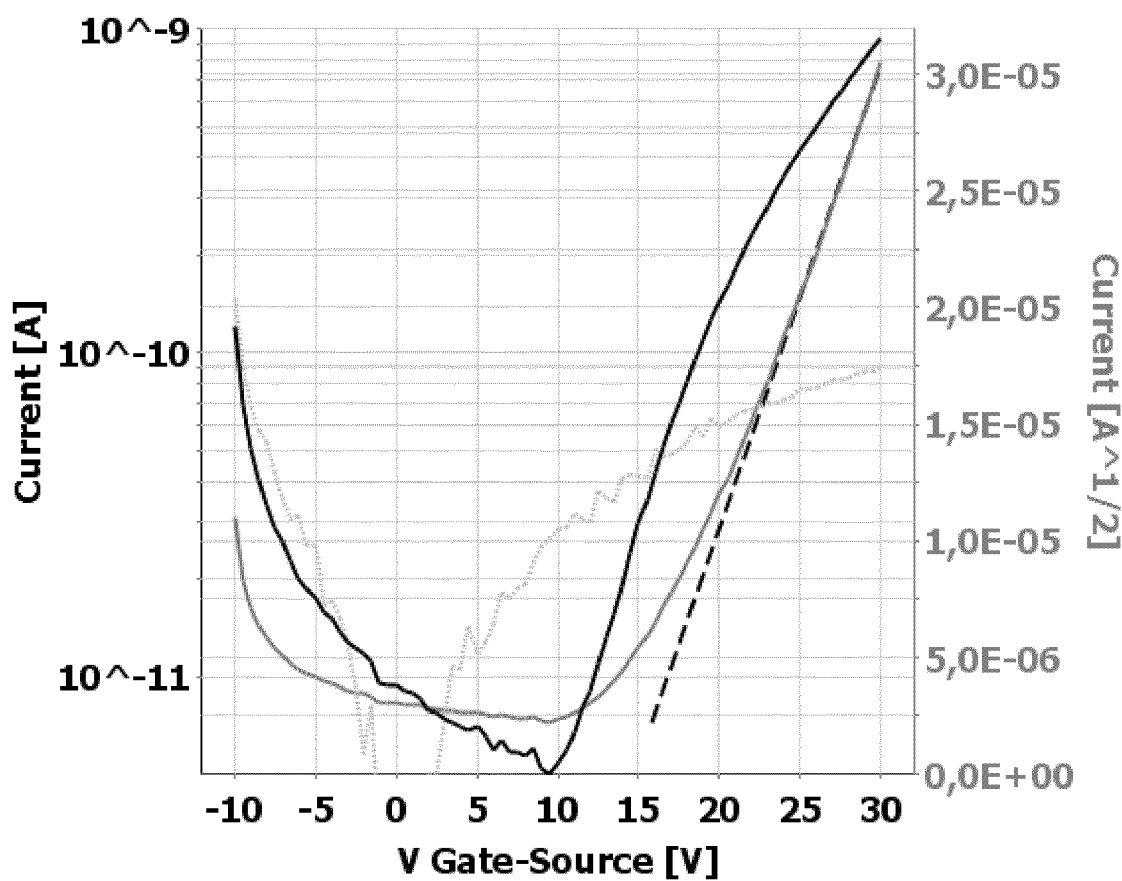

SEMICONDUCTING POLYMER

This application is a National Stage of PCT/EP2017/054507, which was filed on Feb. 27, 2017. This application is based upon and claims the benefit of priority to European Application No. 16207316.7, which was filed on Dec. 29, 2016, and to European Application No. 16157844.8, which was filed on Feb. 29, 2016.

The present invention relates to polymers, to a process for the preparation of these polymers, to intermediates, to electronic devices comprising these polymers, as well as to the use of these polymers as semiconducting material.

Organic semiconducting materials can be used in electronic devices such as organic photovoltaic devices (OPVs), organic field-effect transistors (OFETs), organic light emitting diodes (OLEDs), organic photodiodes (OPDs) and organic electrochromic devices (ECDs).

It is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

For application in organic photovoltaic devices (OPVs), organic field-effect transistors (OFETs), and organic photodiodes (OPDs), it is further desirable that the organic semiconducting materials show high charge carrier mobility.

For application in organic photovoltaic devices (OPVs) and organic photodiodes (OPDs), the organic semiconducting materials should also show a strong absorption of the visible light and of the near infra-red light.

G. Kossmehl and G. Manecke, Die Makromolekulare Chemie 176 (1975), pp. 333-340 discloses the following structures

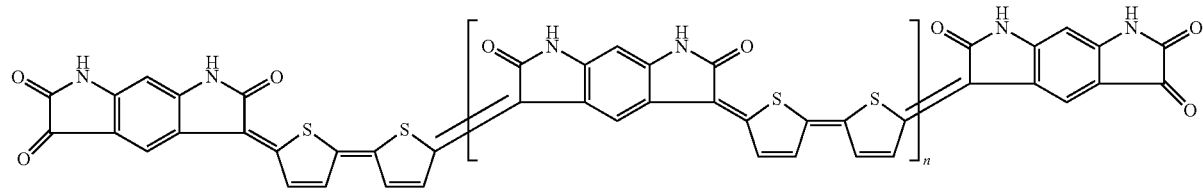

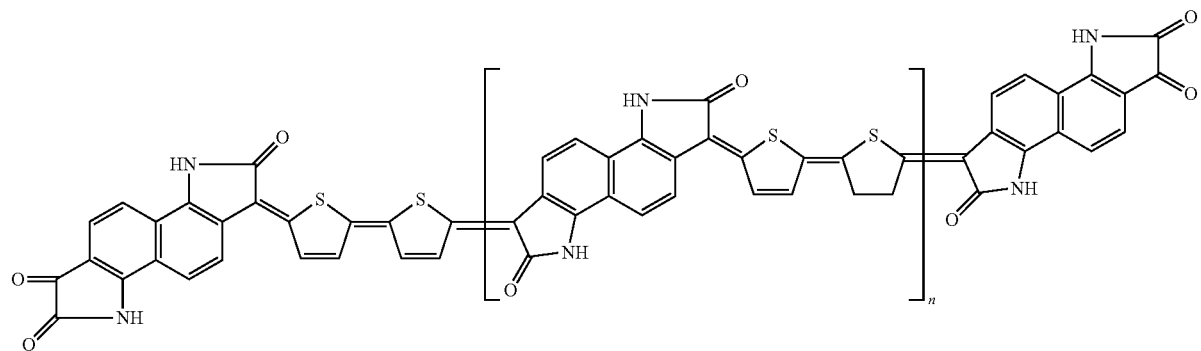

which have coplanar conjugated π-electron systems.

WO 2009/053291 describes semiconducting polymers comprising the following units

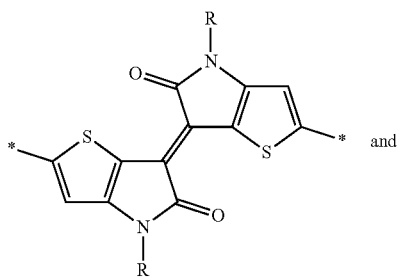

and

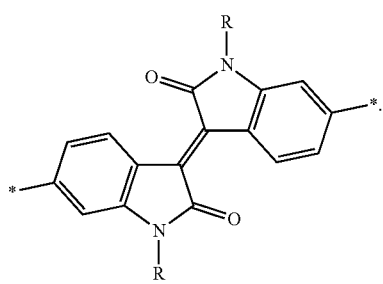

and organic field effect transistors comprising these polymers.

WO 2014/071524 discloses monomers, oligomers and polymers comprising a fused ring moiety of the following structure

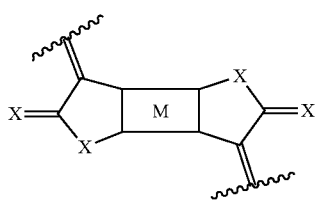

where X is independently O, S or NR and R is independently hydrogen, or an optionally substituted hydrocarbon.

WO 2016/005891 discloses polymers comprising at least one unit of formulae

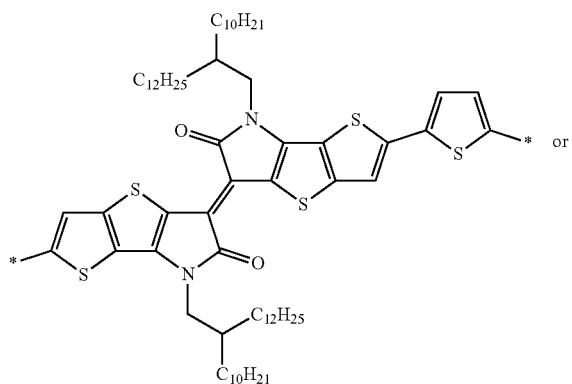

or

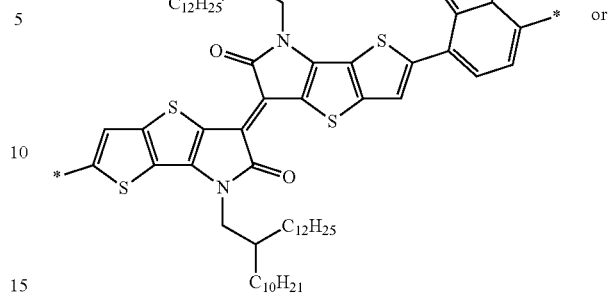

or

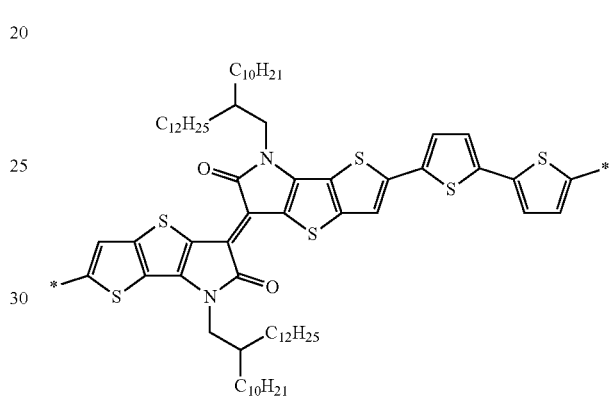

as semiconducting materials for electronic devices.

It was the object of the present invention to provide organic semiconducting materials.

It was a second object of the present invention to provide semiconducting polymers which can be synthesized without the need of noble metal catalysts.

The problem is solved by compounds of formula (I)

(I)

$T^1$, $Ar$, $Q^a$, $Q^b$, $Q^c$, $Q^d$, $Ar'$, $T^2$ and polymers comprising at least a structure of formula (II)
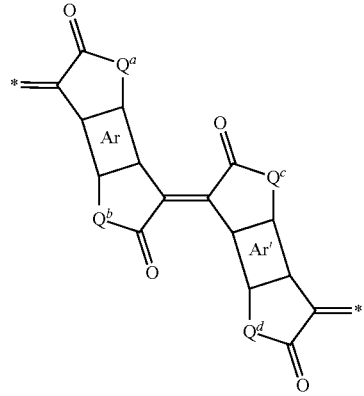
(II)
and preferably polymers comprising at least a structure of formula (II')
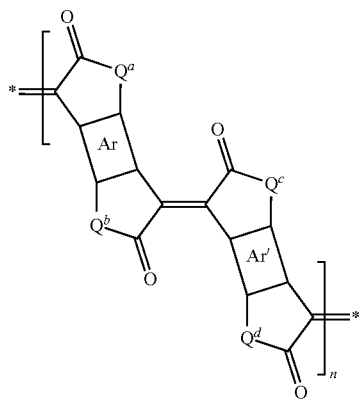
(II')
wherein
n is 3 to 1000,
$T^1$ or $T^2$ are independently of each other a group of formulae =O, =S, =NR$^{1a}$, =CR$^4$R$^{4'}$,
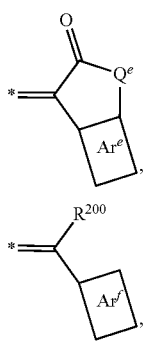
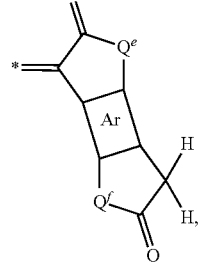
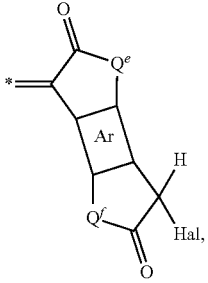
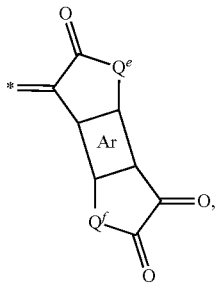
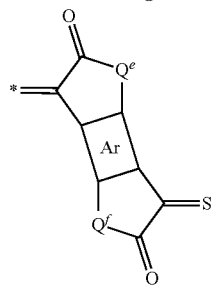
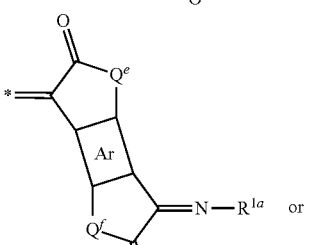 or
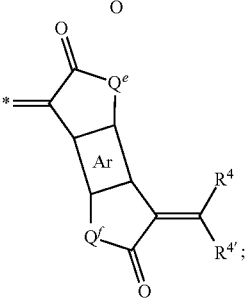

$Q^a$, $Q^b$, $Q^c$, $Q^d$, $Q^e$ or $Q^f$ are independently of each other O, S or $NR^1$, preferably O or $NR^1$, Hal is halogen, preferably Cl or Br, especially Cl.

$T^1$ or $T^2$ are preferably independently of each other a group of formulae =O, =$CR^4R^{4'}$,

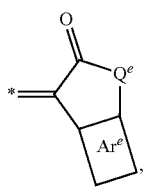

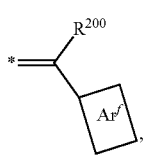

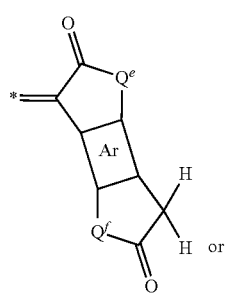

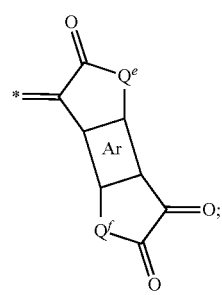

$T^1$ or $T^2$ are more preferably independently of each other a group of formulae

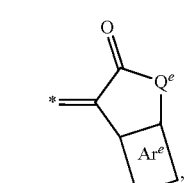

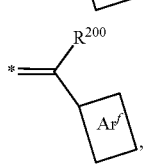

-continued

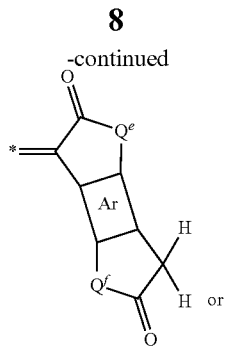

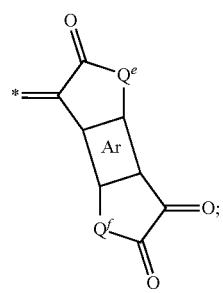

$T^1$ or $T^2$ are even more preferably independently of each other a group of formulae

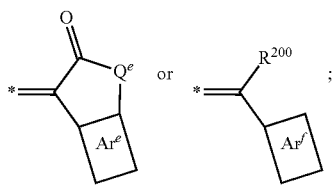

$T^1$ or $T^2$ are most preferably independently of each other a group of formula;

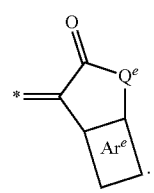

The polymers comprising a structure of formula (II) or (II') can be linked to other moieties by double bonds, e.g. to other groups of formula (II) or (II'), or e.g. to end groups $T^1$ or $T^2$.

Ar, Ar', $Ar^e$ and $Ar^f$ are independently of each other a 5- to 6-membered ring, or a ring system comprising from 2 to 6 fused 5- to 6-membered rings, wherein at least one of the rings is an aromatic or heteroaromatic ring.

Ar and Ar' are preferably independently of each other selected from the group consisting of

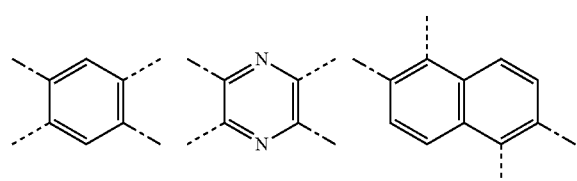
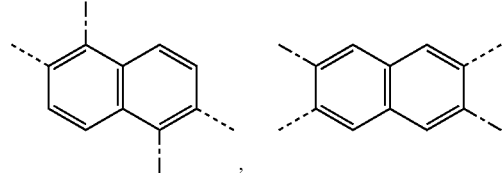
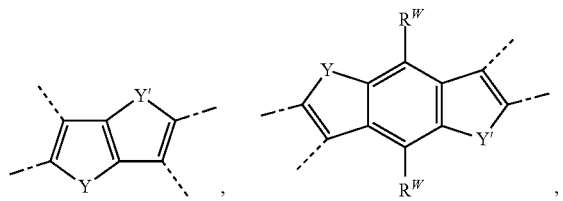
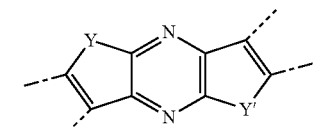
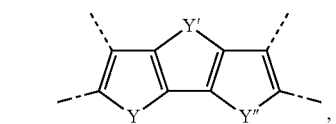
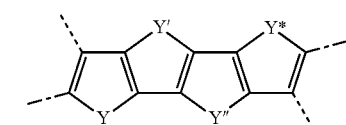
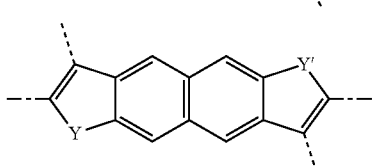
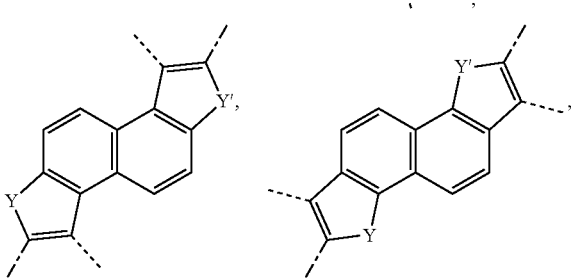
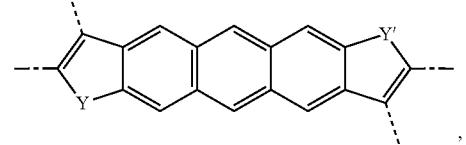
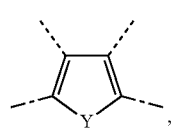
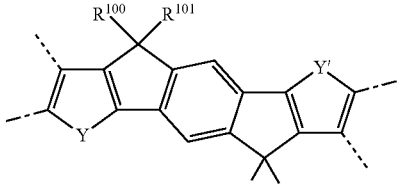
wherein Ar or Ar' is bound via the single bonds ----- and —··— to the moieties
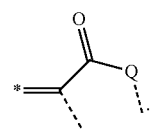
wherein Q is O, S or NR$^1$, preferably O or NR$^1$,
Ar and Ar' are more preferably independently of each other selected from the group consisting of
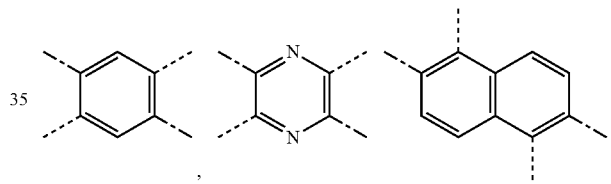
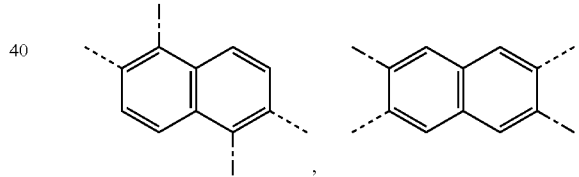
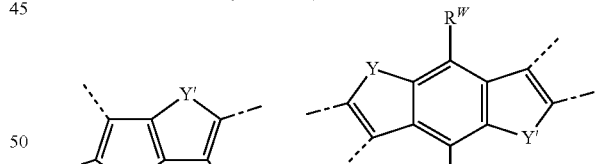
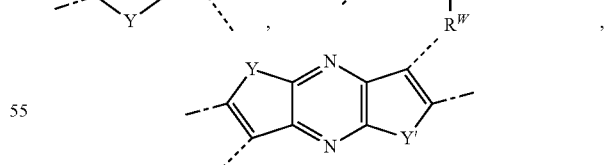
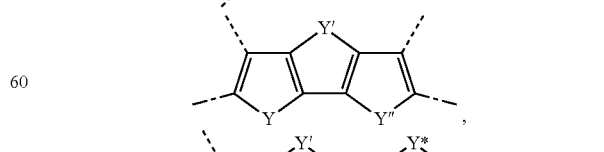
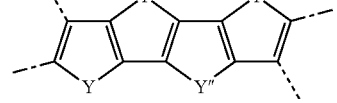

-continued

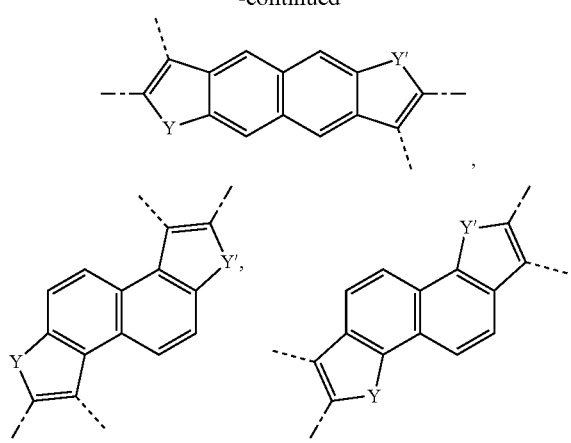

wherein Ar or Ar' is bound via the single bonds ----- and —-- to the moieties

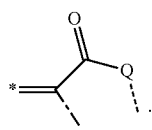

wherein Q is O, S or NR¹, preferably O or NR¹,

Ar and Ar' are even more preferably independently of each other selected from

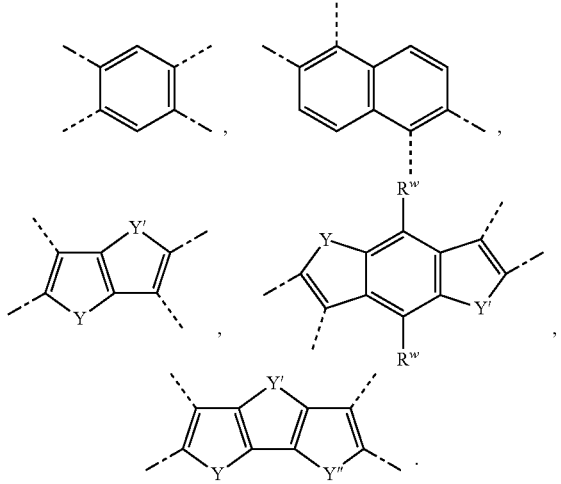

Ar and Ar' are most preferably independently of each other selected from

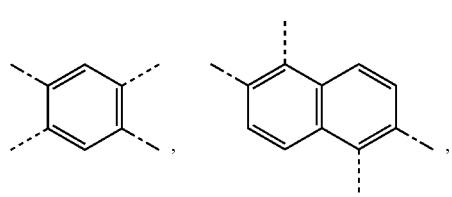

-continued

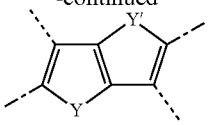

Ar$^e$ is preferably selected from

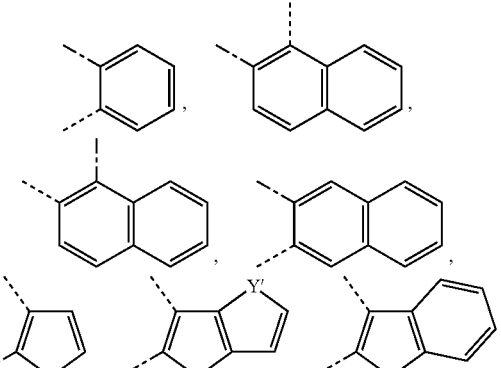

where Ar$^e$ is bound via the bonds ----- and —-- to the moiety

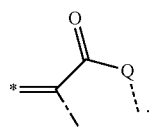

Ar$^e$ is more preferably selected from

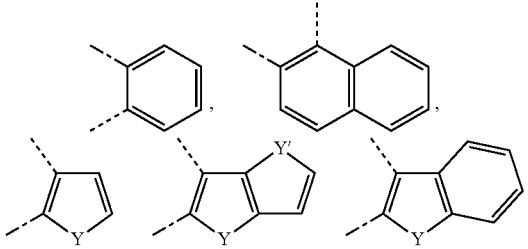

Ar$^e$ is even more preferably selected from

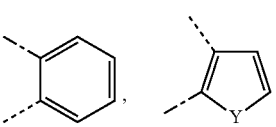

Ar$^e$ is most preferably

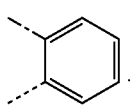

Ar$^f$ is preferably selected from the group consisting of

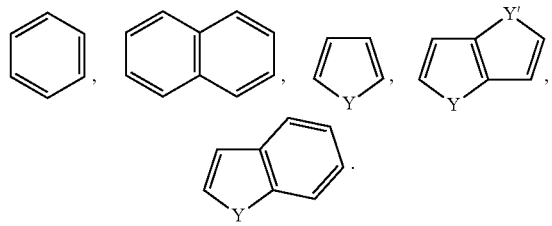

Ar$^f$ is more preferably selected from

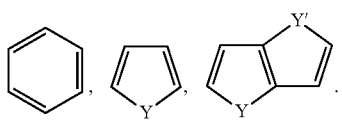

Ar$^f$ is most preferably selected from

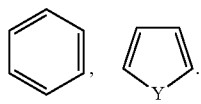

wherein Ar, Ar', Ar$^e$, Ar$^f$ can be substituted by one or more substituents R$^2$.

Y, Y', Y" and Y* are at each occurrence O, S, NR$^{1a}$, Se, Te, preferably O, S, NR$^{1a}$, Se, more preferably O, S, Se, still more preferably S, Se and most preferably S.

R$^W$ is at each occurrence H, C$_{1-30}$-alkyl, C$_{1-30}$-alkoxy, or a moiety

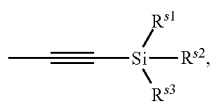

preferably H, C$_{1-30}$-alkyl, or C$_{1-30}$-alkoxy, more preferably H or C$_{1-30}$-alkoxy, most preferably H, wherein R$^{s1}$, R$^{s2}$, R$^{s3}$ are independently of each other H, C$_{1-20}$-alkyl, C$_{2-20}$-alkenyl, or phenyl, preferably C$_{1-20}$-alkyl.

R$^1$, R$^{1a}$ are at each occurrence selected from the group consisting of H, C$_{1-100}$-alkyl, C$_{2-100}$-alkenyl, C$_{2-100}$-alkynyl, C$_{5-12}$-cycloalkyl, C$_{6-18}$-aryl, a 5 to 20 membered heteroaryl, C(O)—C$_{1-100}$-alkyl, C(O)—C$_{5-12}$-cycloalkyl and C(O)—OC$_{1-100}$-alkyl,
wherein
C$_{1-100}$-alkyl, C$_{2-100}$-alkenyl and C$_{2-100}$-alkynyl can be substituted with one to forty substituents independently selected from the group consisting of C$_{5-8}$-cycloalkyl, C$_{6-14}$-aryl, 5 to 14 membered heteroaryl, OR$^a$, OC(O)—R$^a$, C(O)—OR$^a$, C(O)—R$^a$, NR$^a$R$^b$, NR$^a$—C(O)R$^b$, C(O)NR$^a$R$^b$, N[C(O)R$^a$][C(O)R$^b$], SR$^a$, Si(R$^{Sia}$)(R$^{Sib}$)(R$^{Sic}$), —O—Si(R$^{Sia}$)(R$^{Sib}$)(R$^{Sic}$), halogen, CN, and NO$_2$; and at least two CH$_2$-groups, but not adjacent CH$_2$-groups, of C$_{1-100}$-alkyl, C$_{2-100}$-alkenyl and C$_{2-100}$-alkynyl can be replaced by O or S, C$_{5-12}$-cycloalkyl can be substituted with one to six substituents independently selected from the group consisting of C$_{1-60}$-alkyl, C$_{2-60}$-alkenyl, C$_{2-60}$-alkynyl, C$_{5-8}$-cycloalkyl, C$_{6-14}$-aryl, 5 to 14 membered heteroaryl, OR$^a$, OC(O)—R$^a$, C(O)—OR$^a$, C(O)—R$^a$, NR$^a$R$^b$, NR$^a$—C(O)R$^b$, C(O)—NR$^a$R$^b$, N[C(O)R$^a$][C(O)R$^b$], SR$^a$, Si(R$^{Sia}$)(R$^{Sib}$)(R$^{Sic}$), —O—Si(R$^{Sia}$)(R$^{Sib}$)(R$^{Sic}$), halogen, CN, and NO$_2$; and one or two CH$_2$-groups, but not adjacent CH$_2$-groups, of C$_{5-12}$-cycloalkyl can be replaced by O, S, OC(O), CO, NR$^a$ or NR$^a$—CO, C$_{6-18}$-aryl and 5 to 20 membered heteroaryl can be substituted with one to six substituents independently selected from the group consisting of C$_{1-60}$-alkyl, C$_{2-60}$-alkenyl, C$_{2-60}$-alkynyl, C$_{5-8}$-cycloalkyl, C$_{6-14}$-aryl, 5 to 14 membered heteroaryl, OR$^a$, OC(O)—R$^a$, C(O)—OR$^a$, C(O) R$^a$, NR$^a$R$^b$, NR$^a$—C(O)R$^b$, C(O)—NR$^a$R$^b$, N[C(O)R$^a$][C(O)R$^b$], SR$^a$, Si(R$^{Sia}$)(R$^{Sib}$)(R$^{Sic}$), —O—Si(R$^{Sia}$)(R$^{Sib}$)(R$^{Sic}$), halogen, CN, and NO$_2$,
wherein
R$^a$ and R$^b$ are independently selected from the group consisting of H, C$_{1-60}$-alkyl, C$_{2-60}$-alkenyl, C$_{2-60}$-alkynyl, C$_{5-8}$-cycloalkyl, C$_{6-14}$-aryl and 5 to 14 membered heteroaryl, R$^{Sia}$, R$^{Sib}$ and R$^{Sic}$ are independently selected from the group consisting of H, C$_{1-60}$-alkyl, C$_{2-60}$-alkenyl, C$_{2-60}$-alkynyl, C$_{5-8}$-cycloalkyl, C$_{6-14}$-aryl, 5 to 14 membered heteroaryl, O—C$_{1-60}$-alkyl, O—C$_{2-60}$-alkenyl, O—C$_{2-60}$-alkynyl, O—C$_{5-8}$-cycloalkyl, O—C$_{6-14}$-aryl, O-5 to 14 membered heteroaryl, —[O—SiR$^{Sid}$R$^{Sie}$]$_o$—R$^{Sif}$, NR$^5$R$^6$, halogen and O—C(O)—R$^5$,
wherein
o is an integer from 1 to 50, R$^{Sid}$, R$^{Sie}$, R$^{Sif}$ are independently selected from the group consisting of H, C$_{1-60}$-alkyl, C$_{2-60}$-alkenyl, C$_{2-60}$-alkynyl, C$_{5-8}$-cycloalkyl, C$_{6-14}$-aryl, 5 to 14 membered heteroaryl, O—C$_{1-60}$-alkyl, O—C$_{2-60}$-alkenyl, O—C$_{2-60}$-alkynyl, O—C$_{5-8}$-cycloalkyl, O—C$_{6-14}$-aryl, O-5 to 14 membered heteroaryl, —[O—SiR$^{Sig}$R$^{Sih}$]$_p$—R$^{Sii}$, NR$^{50}$R$^{60}$, halogen and O—C(O)—R$^{50}$;
wherein
p is an integer from 1 to 50, R$^{Sig}$, R$^{Sih}$, R$^{Sii}$ are independently selected from the group consisting of H, C$_{1-30}$-alkyl, C$_{2-30}$-alkenyl, C$_{2-30}$-alkynyl, C$_{5-6}$-cycloalkyl, C$_{6-10}$-aryl, 5 to 10 membered heteroaryl, O—C$_{1-30}$-alkyl, O—C$_{2-30}$-alkenyl, O—C$_{2-30}$-alkynyl, O—C$_{5-6}$-cycloalkyl, OC$_{6-10}$-aryl, O-5 to 10 membered heteroaryl, O—Si(CH$_3$)$_3$, NR$^{500}$R$^{600}$, halogen and O—C(O)—R$_{500}$, R$^5$, R$^6$, R$^{50}$, R$^{60}$, R$^{500}$ and R$^{600}$ are independently selected from the group consisting of H, C$_{1-60}$-alkyl, C$_{2-60}$-alkenyl, C$_{2-60}$-alkynyl, C$_{5-8}$-cycloalkyl, C$_{6-14}$-aryl, and 5 to 14 membered heteroaryl, C$_{1-60}$-alkyl, C$_{2-60}$-alkenyl and C$_{2-60}$-alkynyl can be substituted with one to twenty substituents selected from the group consisting of C$_{5-6}$-cycloalkyl, C$_{6-10}$-aryl, OR$^c$, OC(O)—R$^c$, C(O)—OR$^c$, C(O)—R$^c$, NR$^c$R$^d$, NR$^c$—C(O)R$^d$, C(O)—NR$^c$R$^d$, N[C(O)R$^c$][C(O)R$^d$], SR$^c$, Si(R$^{Sij}$)(R$^{Sik}$)(R$^{Sil}$), —O—Si(R$^{Sij}$)(R$^{Sik}$)(R$^{Sil}$), halogen, CN, and NO$_2$; and at least two CH$_2$-groups, but not adjacent CH$_2$-groups, of C$_{1-60}$-alkyl, C$_{2-60}$-alkenyl and C$_{2-60}$-alkynyl can be replaced by O or S, C$_{5-8}$-cycloalkyl can be substituted with one to five substituents selected from the group consisting of C$_{1-30}$-alkyl, C$_{2-30}$-alkenyl, C$_{2-30}$-alkynyl, C$_{5-6}$-cycloalkyl, C$_{6-10}$-aryl, OR$^c$, OC(O)—R$^c$, C(O)—OR$^c$, C(O)—R$^c$, NR$^c$R$^d$, NR$^c$—C(O)R$^d$, C(O)—NR$^c$R$^d$, N[C(O)R$^c$][C(O)R$^d$], SR$^c$, Si(R$^{Sij}$)(R$^{Sik}$)(R$^{Sil}$), —O—Si($R^{Sij}$)($R^{Sik}$)($R^{Sil}$), halogen, CN, and $NO_2$; and one or two $CH_2$-groups, but not adjacent $CH_2$-groups, of $C_{5-8}$-cycloalkyl can be replaced by O, S, OC(O), CO, $NR^c$ or $NR^c$—CO, $C_{6-14}$-aryl and 5 to 14 membered heteroaryl can be substituted with one to five substituents independently selected from the group consisting of $C_{1-30}$-alkyl, $C_{2-30}$-alkenyl, $C_{2-30}$-alkynyl, $C_{5-6}$-cycloalkyl, $C_{6-10}$-aryl, $OR^c$, OC(O)—$R^c$, C(O)—$OR^c$, C(O)—$R^c$, $NR^cR^d$, $NR^c$—C(O)$R^d$, C(O)—$NR^cR^d$, N[C(O)$R^c$][C(O)$R^d$], $SR^c$, Si($R^{Sij}$)($R^{Sik}$)($R^{Sil}$), —O—Si($R^{Sij}$)($R^{Sik}$)($R^{Sil}$), halogen, CN and $NO_2$, wherein $R^c$ and $R^d$ are independently selected from the group consisting of H, $C_{1-30}$-alkyl, $C_{2-30}$-alkenyl and $C_{2-30}$-alkynyl, $R^{Sij}$, $R^{Sik}$ and $R^{Sil}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, —[O—Si$R^{Sim}R^{Sin}]_q$—$R^{Sio}$, $NR^7R^8$, halogen, and O—C(O)—$R^7$, wherein q is an integer from 1 to 50, $R^{Sim}$, $R^{Sin}$, $R^{Sio}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, —[O—Si$R^{Sip}R^{Siq}]_r$—$R^{Sir}$, $NR^{70}R^{80}$, halogen, and O—C(O)—$R^{70}$, wherein r is an integer from 1 to 50, $R^{Sip}$, $R^{Siq}$, $R^{Sir}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, O—Si($CH_3$)$_3$, $NR^{700}R^{800}$, halogen and O—C(O)—$R^{700}$, $R^7$, $R^8$, $R^{70}$, $R^{80}$, $R^{700}$ and $R^{800}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, and 5 to 10 membered heteroaryl, $C_{1-30}$-alkyl, $C_{2-30}$-alkenyl and $C_{2-30}$-alkynyl can be substituted with one to ten substituents selected from the group consisting of halogen, CN and $NO_2$.

$R^1$, $R^{1a}$ are preferably at each occurrence selected from the group consisting of H, $C_{1-100}$-alkyl, $C_{3-100}$-alkenyl, $C_{3-100}$-alkynyl, wherein $C_{1-100}$-alkyl, $C_{3-100}$-alkenyl and $C_{3-100}$-alkynyl can be substituted with one to forty substituents independently selected from the group consisting of $C_{5-8}$-cycloalkyl, $OR^a$, OC(O)—$R^a$, C(O)—$OR^a$, C(O)—$R^a$, Si($R^{Sia}$)($R^{Sib}$)($R^{Sic}$), and halogen; and at least two $CH_2$-groups, but not adjacent $CH_2$-groups, of $C_{1-100}$-alkyl, $C_{3-100}$-alkenyl and $C_{3-100}$-alkynyl can be replaced by O or S, wherein $R^a$ is selected from the group consisting of H, $C_{1-60}$-alkyl, $C_{3-60}$-alkenyl, $C_{3-60}$-alkynyl, $C_{5-8}$-cycloalkyl, $R^{Sia}$, $R^{Sib}$ and $R^{Sic}$ are independently selected from the group consisting of H, $C_{1-60}$-alkyl, $C_{2-60}$-alkenyl, $C_{2-60}$-alkynyl, $C_{5-8}$-cycloalkyl, —[O—Si $R^{Sid}R^{Sie}]_o$—$R^{Sif}$, wherein o is an integer from 1 to 50, $R^{Sid}$, $R^{Sie}$, $R^{Sif}$ are independently selected from the group consisting of H, $C_{1-60}$-alkyl, $C_{2-60}$-alkenyl, $C_{2-60}$-alkynyl, $C_{5-8}$-cycloalkyl and —[O—Si$R^{Sig}R^{Sih}]_p$—$R^{Sii}$;

wherein p is an integer from 1 to 50, $R^{Sig}$ $R^{Sih}$, $R^{Sii}$ are independently selected from the group consisting of H, $C_{1-30}$-alkyl, $C_{2-30}$-alkenyl, $C_{2-30}$-alkynyl, $C_{5-6}$-cycloalkyl, O—Si($CH_3$)$_3$, $R^1$, $R^{1a}$ are more preferably at each occurrence selected from the group consisting of H, $C_{1-50}$-alkyl, $C_{3-50}$-alkenyl, $C_{3-50}$-alkynyl, wherein $C_{1-50}$-alkyl, $C_{3-50}$-alkenyl and $C_{3-50}$-alkynyl can be substituted with one to twenty substituents independently selected from the group consisting of $OR^a$, OC(O)—$R^a$, C(O)—$OR^a$, Si($R^{Sia}$)($R^{Sib}$)($R^{Sic}$), and halogen; and at least two $CH_2$-groups, but not adjacent $CH_2$-groups, of $C_{1-50}$-alkyl, $C_{3-50}$-alkenyl and $C_{3-50}$-alkynyl can be replaced by O or S, wherein $R^a$ is selected from the group consisting of H, $C_{1-20}$-alkyl, $C_{3-20}$-alkenyl, $C_{3-20}$-alkynyl, $R^{Sia}$, $R^{Sib}$ and $R^{Sic}$ are independently selected from the group consisting of H, $C_{1-20}$-alkyl, $C_{2-20}$-alkenyl, —[O—Si$R^{Sid}R^{Sie}]_o$—$R^{Sif}$, wherein o is an integer from 1 to 20, $R^{Sid}$, $R^{Sie}$, $R^{Sif}$ are independently selected from the group consisting of H, $C_{1-20}$-alkyl, $C_{2-20}$-alkenyl, and —[O—Si$R^{Sig}R^{Sih}]_p$—$R^{Sii}$;

wherein p is an integer from 1 to 20, $R^{Sig}$ $R^{Sih}$, $R^{Sii}$ are independently selected from the group consisting of H, $C_{1-20}$-alkyl, $C_{2-20}$-alkenyl, O—Si($CH_3$)$_3$, $R^1$, $R^{1a}$ are even more preferably at each occurrence selected from the group consisting of $C_{1-50}$-alkyl, $C_{3-50}$-alkenyl, $C_{3-50}$-alkynyl, wherein $C_{1-50}$-alkyl, $C_{3-50}$-alkenyl and $C_{3-50}$-alkynyl can be substituted with one to twenty substituents independently selected from the group consisting of $OR^a$, and halogen; and at least two $CH_2$-groups, but not adjacent $CH_2$-groups, of $C_{1-50}$-alkyl, $C_{3-50}$-alkenyl and $C_{3-50}$-alkynyl can be replaced by O or S, wherein $R^a$ is selected from the group consisting of H, $C_{1-20}$-alkyl, $C_{3-20}$-alkenyl, $C_{3-20}$-alkynyl, $R^1$, $R^{1a}$ are much more preferably at each occurrence selected from the group consisting of $C_{1-50}$-alkyl, wherein $C_{1-50}$-alkyl can be substituted with one to twenty substituents independently selected from the group consisting of $OR^a$, and halogen; and at least two $CH_2$-groups, but not adjacent $CH_2$-groups, of $C_{1-50}$-alkyl can be replaced by O or S, wherein $R^a$ is selected from the group consisting of H, or $C_{1-20}$-alkyl, $R^1$, $R^{1a}$ are especially preferably at each occurrence selected from the group consisting of $C_{1-50}$-alkyl,
wherein
$C_{1-50}$-alkyl can be substituted with one to twenty halogens;
$R^1$, $R^{1a}$ are most preferably $C_{1-50}$-alkyl,
$R^2$ is at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl, 5 to 20 membered heteroaryl, $OR^{21}$, $OC(O)$—$R^{21}$, $C(O)OR^{21}$, $C(O)$—$R^{21}$, $NR^{21}R^{22}$, $NR^{21}$—$C(O)R^{22}$, $C(O)$—$NR^{21}R^{22}$, $N[C(O)R^{21}][C(O)R^{22}]$, $SR^{21}$, halogen, CN, $SiR^{Sis}R^{Sit}R^{Siu}$ and OH,
wherein
$R^{21}$ and $R^{22}$ and are independently selected from the group consisting of H, $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, and
$C_{1-30}$-alkyl, $C_{2-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, $OR^e$, $OC(O)$—$R^e$, $C(O)$—$OR^e$, $C(O)$—$R^e$, $NR^eR^f$, $NR^e$—$C(O)R^f$, $C(O)NR^eR^f$, $N[C(O)R^e][C(O)R^f]$, $SR^e$, halogen, CN, $SiR^{Sis}R^{Sit}R^{Siu}$ and $NO_2$; and at least two $CH_2$-groups, but not adjacent $CH_2$-groups, of $C_{1-30}$-alkyl, $C_{2-30}$-alkenyl and $C_{2-30}$-alkynyl can be replaced by O or S,
$C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^e$, $OC(O)$—$R^e$, $C(O)$—$OR^e$, $C(O)$—$R^e$, $NR^eR^f$, $NR^e$—$C(O)R^f$, $C(O)$—$NR^eR^f$, $N[C(O)R^e][C(O)R^f]$, $SR^e$, halogen, CN, $SiR^{Sis}R^{Sit}R^{Siu}$ and $NO_2$; and one or two $CH_2$-groups, but not adjacent $CH_2$-groups, of $C_{5-12}$-cycloalkyl can be replaced by O, S, OC(O), CO, $NR^e$ or $NR^e$—CO,
$C_{6-18}$-aryl and 5 to 20 membered heteroaryl can be substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^e$, $OC(O)$—$R^e$, $C(O)$—$OR^e$, $C(O)R^e$, $NR^eR^f$, $NR^e$—$C(O)R^f$, $C(O)$—$NR^eR^f$, $N[C(O)R^e][C(O)R^f]$, $SR^e$, halogen, CN, $SiR^{Sis}R^{Sit}R^{Siu}$ and $NO_2$,
wherein
$R^{Sis}$, $R^{Sit}$ and $R^{Siu}$ are independently from each other selected from the group consisting of H, $C_{1-20}$-alkyl, $C_{2-20}$-alkenyl, $C_{2-20}$-alkynyl, $C_{5-6}$-cycloalkyl, phenyl and O—$Si(CH_3)_3$,
$R^e$ and $R^f$ are independently selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl,
wherein
$C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^g$, $OC(O)$—$R^g$, $C(O)$—$OR^g$, $C(O)$—$R^g$, $NR^gR^h$, $NR^g$—$C(O)R^h$, $C(O)NR^gR^h$, $N[C(O)R^g][C(O)R^h]$, $SR^g$, halogen, CN, and $NO_2$,
$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^g$, $OC(O)$—$R^g$, $C(O)$—$OR^g$, $C(O)$—$R^g$, $NR^gR^h$, $NR^gC(O)R^h$, $C(O)$—$NR^gR^h$, $N[C(O)R^g][C(O)R^h]$, $SR^g$, halogen, CN, and $NO_2$,
$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^g$, $OC(O)$—$R^g$, $C(O)$—$OR^g$, $C(O)$—$R^g$, $NR^gR^h$, $NR^g$—$C(O)R^h$, $C(O)$—$NR^gR^h$, $N[C(O)R^g][C(O)R^h]$, $SR^g$, halogen, CN, and $NO_2$,
wherein
$R^g$ and $R^h$ are independently selected from the group consisting of H, $C_{1-10}$-alkyl, $C_{2-10}$-alkenyl and $C_{2-10}$-alkynyl,
wherein
$C_{1-10}$-alkyl, $C_{2-10}$-alkenyl and $C_{2-10}$-alkynyl can be substituted with one to five substituents selected from the group consisting of halogen, CN and $NO_2$.
$R^2$ is preferably at each occurrence selected from the group consisting of $C_{1-30}$-alkyl, $C_{2-30}$-alkenyl, $C_{2-30}$-alkynyl, $OR^{21}$, $C(O)$—$OR^{21}$, $C(O)$—$R^{21}$, halogen, and CN,
wherein
$R^{21}$ is selected from the group consisting of H, $C_{1-30}$-alkyl, $C_{3-30}$-alkenyl, $C_{3-30}$-alkynyl, and
$C_{1-30}$-alkyl, $C_{3-30}$-alkenyl and $C_{3-30}$-alkynyl can be substituted with one to ten substituents independently selected from the group consisting of $OR^e$, $OC(O)$—$R^e$, $C(O)$—$OR^e$, $C(O)$—$R^e$, and halogen; and at least two $CH_2$-groups, but not adjacent $CH_2$-groups, of $C_{1-30}$-alkyl, $C_{3-30}$-alkenyl and $C_{3-30}$-alkynyl can be replaced by O or S,
wherein
$R^e$ is selected from the group consisting of H, $C_{1-20}$-alkyl, $C_{3-20}$-alkenyl, $C_{3-20}$-alkynyl.
$R^2$ is more preferably at each occurrence selected from the group consisting of $C_{1-30}$-alkyl, $OR^{21}$, and halogen,
wherein
$R^{21}$ is $C_{1-30}$-alkyl, and
$C_{1-30}$-alkyl can be substituted with one to ten substituents independently selected from the group consisting of $OR^e$, and halogen; and at least two $CH_2$-groups, but not adjacent $CH_2$-groups, of $C_{1-30}$-alkyl can be replaced by O or S,
wherein $R^e$ is independently selected from the group consisting of H, or $C_{1-20}$-alkyl.
$R^2$ is even more preferably at each occurrence selected from the group consisting of $C_{1-20}$-alkyl, $OR^{21}$, and halogen,
wherein $R^{21}$ is $C_{1-20}$-alkyl, and
$C_{1-20}$-alkyl can be substituted with one to ten halogens; and at least two $CH_2$-groups, but not adjacent $CH_2$-groups, of $C_{1-20}$-alkyl can be replaced by O or S.
$R^2$ is much more preferably at each occurrence selected from the group consisting of $C_{1-20}$-alkyl, $OR^{21}$, and halogen,
wherein
$R^{21}$ is $C_{1-20}$-alkyl, which can optionally be substituted with one to ten halogens.
$R^2$ is especially preferably at each occurrence selected from the group consisting of $C_{1-20}$-alkyl, $OR^{21}$, and halogen, wherein R$^{21}$ is C$_{1-20}$-alkyl.

R$^2$ is most preferably at each occurrence selected from the group consisting of OR$^{21}$, and halogen, wherein R$^{21}$ is C$_{1-20}$-alkyl.

R$^4$ and R$^{4'}$ are independently and at each occurrence selected from the group consisting of H, C$_{1-30}$-alkyl, C$_{2-30}$-alkenyl, C$_{2-30}$-alkynyl, C$_{5-12}$-cycloalkyl, C$_{6-18}$-aryl and 5 to 20 membered heteroaryl, C(O)—R$^{41}$, C(O)—NR$^{41}$R$^{42}$, C(O)—OR$^{41}$ and CN, wherein R$^{41}$ und R$^{42}$ are independently from each other and at each occurrence selected from the group consisting of H, C$_{1-30}$-alkyl, C$_{2-30}$-alkenyl, C$_{2-30}$-alkynyl, C$_{5-12}$-cycloalkyl, C$_{6-18}$-aryl and 5 to 20 membered heteroaryl, and wherein C$_{1-30}$-alkyl, C$_{2-30}$-alkenyl and C$_{2-30}$-alkynyl can be substituted with one to ten substituents independently selected from the group consisting of C$_{5-8}$-cycloalkyl, C$_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, and NO$_2$; and at least two CH$_2$-groups, but not adjacent CH$_2$-groups of C$_{1-30}$-alkyl, C$_{2-30}$-alkenyl and C$_{2-30}$-alkynyl can be replaced by O or S, C$_{5-12}$-cycloalkyl can be substituted with one to six substituents independently selected from the group consisting of C$_{1-20}$-alkyl, C$_{2-20}$-alkenyl and C$_{2-20}$-alkynyl, C$_{5-8}$-cycloalkyl, C$_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, and NO$_2$; and one or two CH$_2$-groups, but not adjacent CH$_2$-groups, of C$_{5-12}$-cycloalkyl can be replaced by O, S, OC(O), CO, NR$^i$ or NR$^i$—CO, C$_{6-18}$-aryl and 5 to 20 membered heteroaryl can be substituted with one to six substituents independently selected from the group consisting of C$_{1-20}$-alkyl, C$_{2-20}$-alkenyl, C$_{2-20}$-alkynyl, C$_{5-8}$-cycloalkyl, C$_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, and NO$_2$, Ri and Rj are independently selected from the group consisting of H, C$_{1-20}$-alkyl, 20 C$_{2-20}$-alkenyl, C$_{2-20}$-alkynyl, C$_{5-8}$-cycloalkyl, R$^4$ and R$^{4'}$ are preferably independently and at each occurrence selected from the group consisting of H, C$_{1-30}$-alkyl, C$_{2-30}$-alkenyl, C$_{2-30}$-alkynyl, C$_{6-18}$-aryl and 5 to 20 membered heteroaryl, C(O)—R$^{41}$, C(O)—NR$^{41}$R$^{42}$, C(O)—OR$^{41}$ and CN, wherein R$^{41}$ und R$^{42}$ are independently from each other and at each occurrence selected from the group consisting of H, C$_{1-30}$-alkyl, C$_{2-30}$-alkenyl, C$_{2-30}$-alkynyl, and wherein C$_{1-30}$-alkyl, C$_{2-30}$-alkenyl and C$_{2-30}$-alkynyl can be substituted with one to ten substituents independently selected from the group consisting of OR$^i$, and halogen; and at least two CH$_2$-groups, but not adjacent CH$_2$-groups of C$_{1-30}$-alkyl, C$_{2-30}$-alkenyl and C$_{2-30}$-alkynyl can be replaced by O or S, C$_{6-18}$-aryl and 5 to 20 membered heteroaryl can be substituted with one to six substituents independently selected from the group consisting of C$_{1-20}$-alkyl, OR$^i$, halogen, Ri is selected from the group consisting of H, C$_{1-20}$-alkyl, 20 C$_{2-20}$-alkenyl, C$_{2-20}$-alkynyl, C$_{5-8}$-cycloalkyl, R$^4$ and R$^{4'}$ are more preferably independently and at each occurrence selected from the group consisting of H, C$_{1-30}$-alkyl, C(O)—R$^{41}$, C(O)—NR$^{41}$R$^{42}$, C(O)—OR$^{41}$ and CN, wherein R$^{41}$ und R$^{42}$ are independently from each other and at each occurrence selected from the group consisting of H, or C$_{1-30}$-alkyl, R$^4$ and R$^{4'}$ are most preferably independently and at each occurrence selected from the group consisting of C(O)—R$^{41}$, C(O)—NR$^{41}$R$^{42}$, C(O)—OR$^{41}$ and CN, wherein R$^{41}$ und R$^{42}$ are independently from each other and at each occurrence selected from the group consisting of H, or C$_{1-30}$-alkyl, R$^{200}$ is hydrogen, C$_1$-C$_{36}$alkyl, C$_2$-C$_{36}$alkenyl, C$_2$-C$_{36}$alkinyl, Ar$^{200}$, CN, COOR$^{201}$, CONR$^{202}$R$^{203}$, COR$^{204}$.

R$^{201}$, R$^{202}$, R$^{203}$ and R$^{204}$ are independently of each other hydrogen, C$_1$-C$_{36}$alkyl, C$_2$-C$_{36}$alkenyl, C$_2$-C$_{36}$alkinyl, or phenyl;

Ar$^{200}$ has the meaning of Ar$^f$;

Halogen can be F, Cl, Br and I.

C$_{1-4}$-alkyl, C$_{1-10}$-alkyl, C$_{1-20}$-alkyl, C$_{1-30}$-alkyl, C$_{1-36}$-alkyl, C$_{1-50}$-alkyl, C$_{1-60}$-alkyl and C$_{1-100}$-alkyl can be branched or unbranched. Examples of C$_{1-4}$-alkyl are methyl, ethyl, n-propyl, isopropyl, n-butyl, sec-butyl, isobutyl and tert-butyl. Examples of C$_{1-10}$-alkyl are C$_{1-4}$-alkyl, n-pentyl, neopentyl, isopentyl, n-(1-ethyl)propyl, n-hexyl, n-heptyl, n-octyl, n-(2-ethyl)hexyl, n-nonyl and n-decyl. Examples of C$_{1-20}$-alkyl are C$_{1-10}$-alkyl and n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl (C$_{20}$). Examples of C$_{1-30}$-alkyl, C$_{1-36}$-alkyl, C$_{1-50}$-alkyl, C$_{1-60}$-alkyl and C$_{1-100}$-alkyl are C$_{1-20}$-alkyl and n-docosyl (C$_{22}$), n-tetracosyl (C$_{24}$), n-hexacosyl (C$_{26}$), n-octacosyl (C$_{28}$) and n-triacontyl (C$_{30}$).

C$_{2-10}$-alkenyl, C$_{2-20}$-alkenyl, C$_{2-30}$-alkenyl, C$_{2-60}$-alkenyl and C$_{2-100}$-alkenyl can be branched or unbranched. Examples of C$_{1-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl and docenyl. Examples of C$_{2-20}$-alkenyl, C$_{2-60}$-alkenyl and C$_{2-100}$-alkenyl are C$_{2-10}$-alkenyl and linoleyl (C$_{18}$), linolenyl (C$_{18}$), oleyl (C$_{18}$), and arachidonyl (C$_{20}$). Examples of C$_{2-30}$-alkenyl are C$_{2-20}$-alkenyl and erucyl (C$_{22}$).

C$_{2-10}$-alkynyl, C$_{2-20}$-alkynyl, C$_{2-30}$-alkynyl, C$_{2-60}$-alkynyl and C$_{2-100}$-alkynyl can be branched or unbranched. Examples of C$_{2-10}$-alkynyl are ethynyl, 2-propynyl, 2-butynyl, 3-butynyl, pentynyl, hexynyl, heptynyl, octynyl, nonynyl and decynyl. Examples of C$_{2-20}$-alkynyl, C$_{2-30}$-alkenyl, C$_{2-60}$-alkynyl and C$_{2-100}$-alkynyl are undecynyl, dodecynyl, undecynyl, dodecynyl, tridecynyl, tetradecynyl, pentadecynyl, hexadecynyl, heptadecynyl, octadecynyl, nonadecynyl and icosynyl (C$_{20}$).

Examples of C$_{5-6}$-cycloalkyl are cyclopentyl and cyclohexyl. Examples of C$_{5-8}$-cycloalkyl are C$_{5-6}$-cycloalkyl and cycloheptyl and cyclooctyl. $C_{5-12}$-cycloalkyl are $C_{5-8}$-cycloalkyl and cyclononyl, cyclodecyl, cycloundecyl and cyclododecyl.

Examples of $C_{6-10}$-aryl are phenyl,

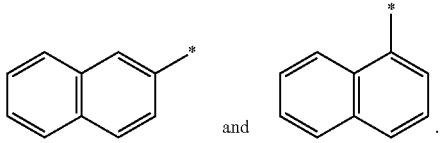 [SMILES: *c1ccc2ccccc2c1 ; *c1cccc2ccccc12]

Examples of $C_{6-14}$-aryl are $C_{6-10}$-aryl and

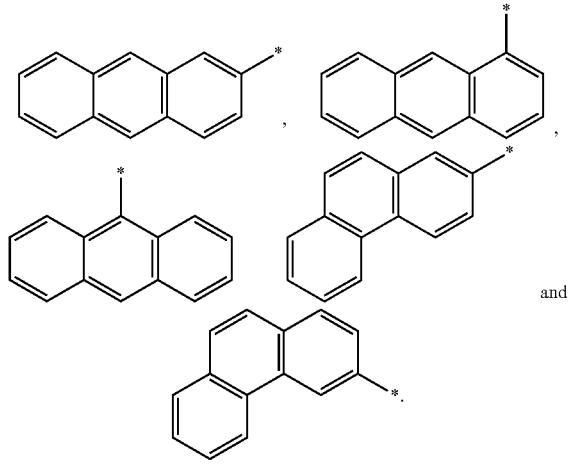

Examples of $C_{6-18}$-aryl are $C_{6-14}$-aryl and

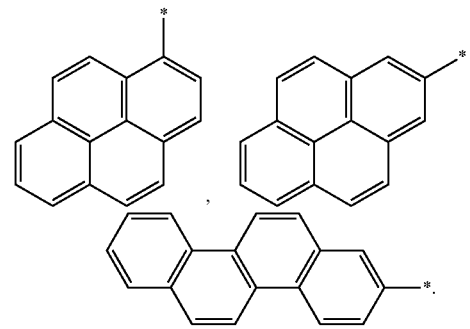

Preferred aryl moieties are phenyl,

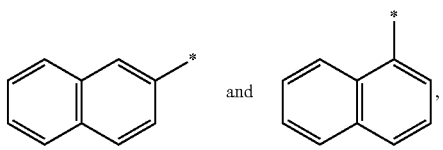 [SMILES: *c1ccc2ccccc2c1 ; *c1cccc2ccccc12]

Most preferred is phenyl.

5 to 10 membered heteroaryl are 5 to 10 membered monocyclic or polycyclic, such as dicyclic, tricyclic or tetracyclic, ring systems, which comprise at least one heteroaromatic ring, and which may also comprise non-aromatic rings, which may be substituted by =O.

5 to 14 membered heteroaryl are 5 to 14 membered monocyclic or polycyclic, such as dicyclic, tricyclic or tetracyclic, ring systems, which comprise at least one heteroaromatic ring, and which may also comprise non-aromatic rings, which may be substituted by =O.

5 to 20 membered heteroaryl are 5 to 20 membered monocyclic or polycyclic, such as dicyclic, tricyclic or tetracyclic, ring systems, which comprise at least one heteroaromatic ring, and which may also comprise non-aromatic rings, which may be substituted by =O.

Examples of 5 to 10 membered heteroaryl are

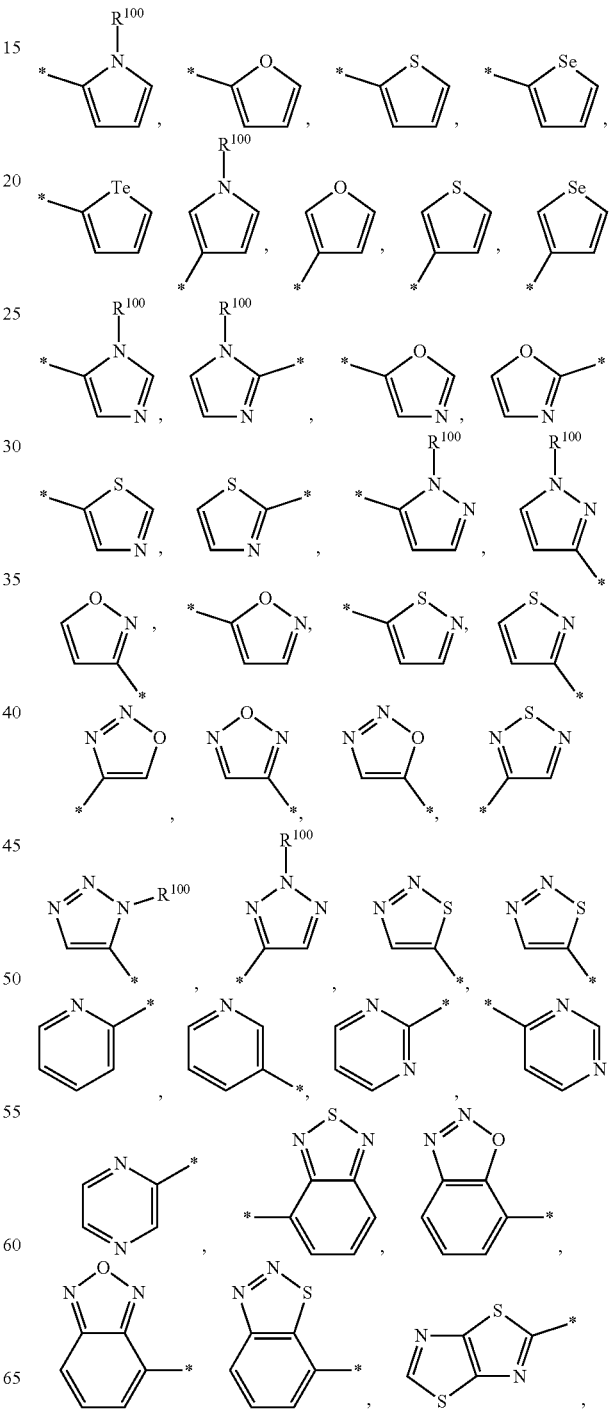

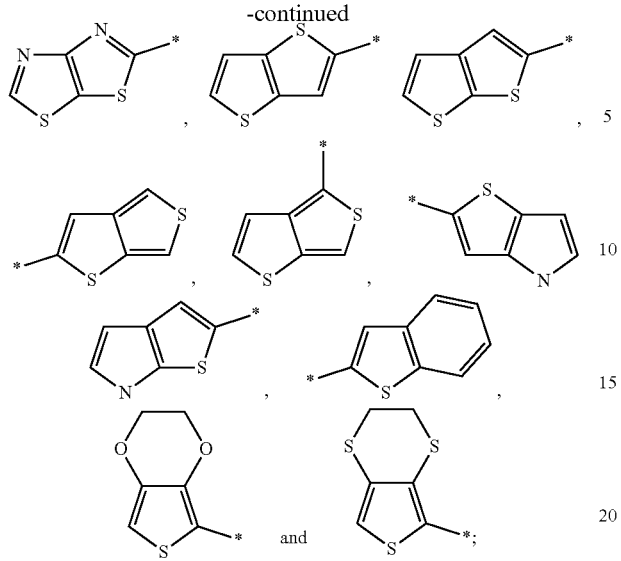
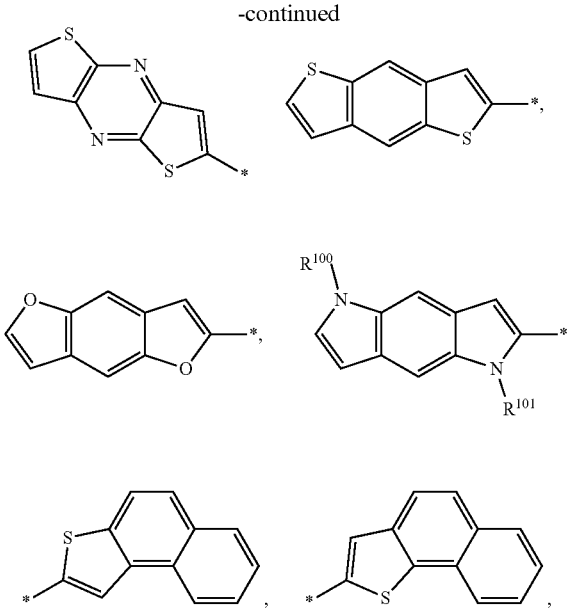
examples of 5 to 14 membered heteroaryl are the examples given for the 5 to 10 membered heteroaryl and
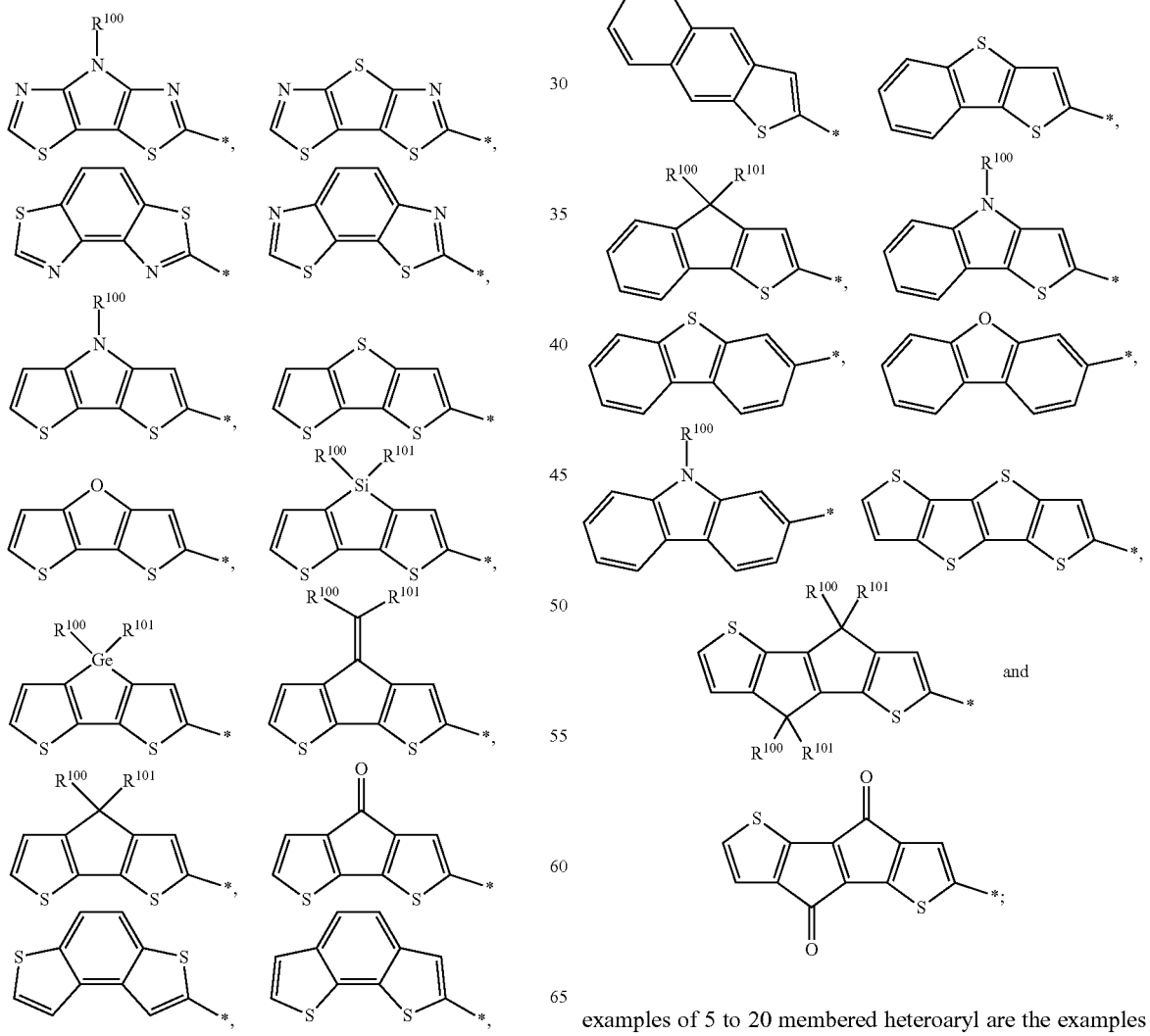
examples of 5 to 20 membered heteroaryl are the examples given for the 5 to 14 membered heteroaryl and

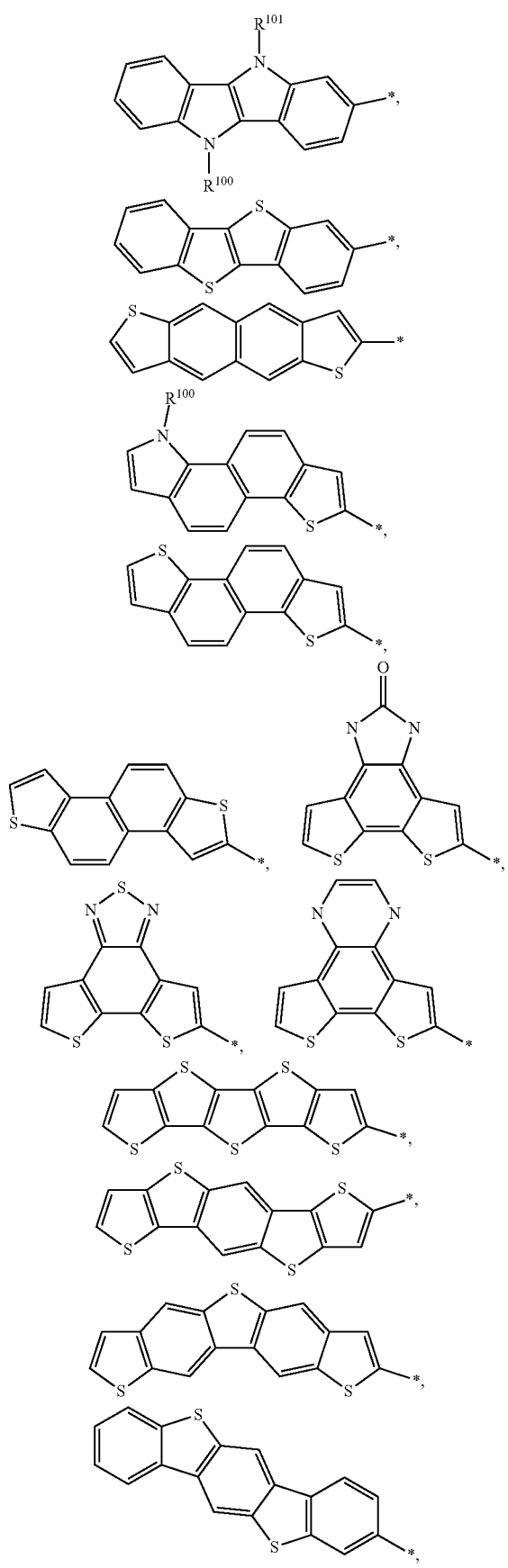
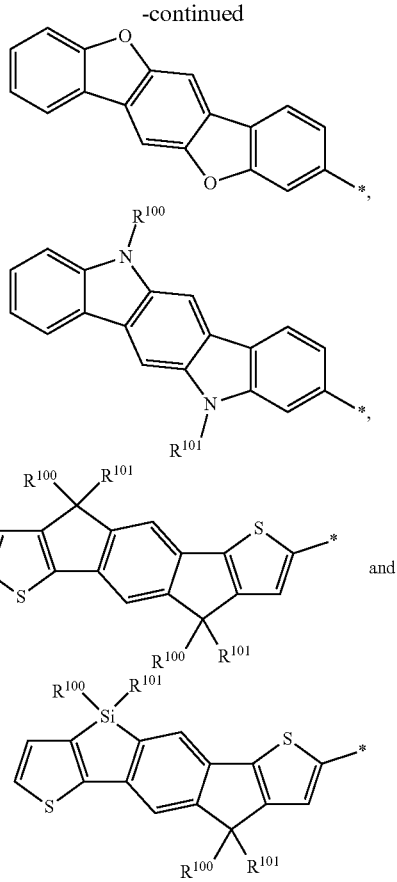

wherein
R[100] and R[101] are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or R[100] and R[101], if attached to the same atom, together with the atom, to which they are attached, form a 5 to 12 membered ring system, wherein
$C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, OR$^q$, OC(O)—R$^q$, C(O)—OR$^q$, C(O)—R$^q$, NR$^q$R$^r$, NR$^q$—C(O)R$^r$, C(O)—NR$^g$R$^r$, N[C(O)R$^q$][C(O)R$^r$], SR$^q$, halogen, CN, and NO$_2$;

$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, OR$^q$, OC(O)—R$^q$, C(O)—OR$^q$, C(O)—R$^q$, NR$^q$R$^r$, NR$^q$—C(O)R$^r$, C(O)NR$^q$R$^r$, N[C(O)R$^q$][C(O)R$^r$], SR$^q$, halogen, CN, and NO$_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, OR$^q$, OC(O)—R$^q$, C(O)—OR$^q$, C(O)—R$^q$, NR$^q$R$^r$, NR$^q$—C(O)R$^r$, C(O)—NR$^q$R$^r$, N[C(O)R$^q$][C(O)R$^r$], SR$^q$, halogen, CN, and NO$_2$;

5 to 12 membered ring system can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^q$, $OC(O)$—$R^q$, $C(O)$—$OR^q$, $C(O)$—$R^q$, $NR^qR^r$, $NR^qC(O)R^r$, $C(O)$—$NR^qR^r$, $N[C(O)R^q][C(O)R^r]$, $SR^q$, halogen, CN, and $NO_2$;

wherein $R^q$ and $R^r$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

$C_{6-18}$-arylene is a 6 to 18 membered monocyclic or polycyclic, such as dicyclic, tricyclic or tetracyclic, ring system, which comprises at least one C-aromatic ring, and which may also comprise non-aromatic rings, which may be substituted by =O.

Preferred heteroaryl moieties are

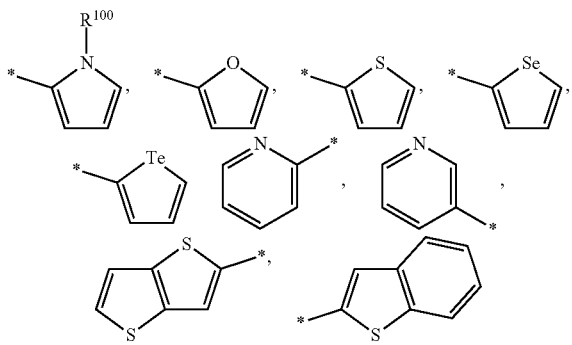

More preferred heteroaryl moieties are

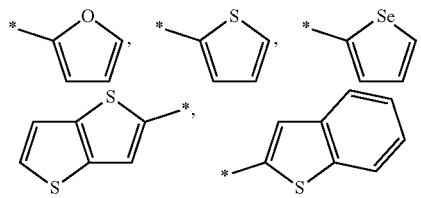

Even more preferred heteroaryl moieties are

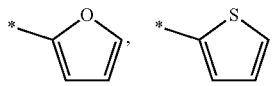

Most preferred heteroaryl moiety is

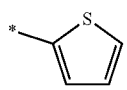

Preferred polymers comprise at least a structure of formula (II')

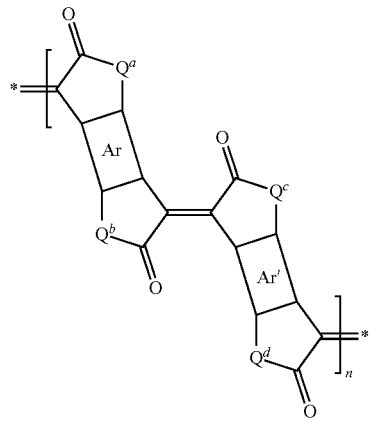

(II')

where n is an integer of 4 to 500, more preferably n is 5 to 400, more preferably n is 6 to 300, even more preferably n is 7 to 200 and most preferably n is 8 to 100, especially 10 to 50.

Preferably the polymers contain more than 10% by weight groups of formula (II'), more preferably contain more than 30% by weight groups of formula (II'), even more preferably contain more than 50% by weight groups of formula (II'), much more preferably contain more than 70% by weight groups of formula (II'), and most preferably contain more than 90% by weight groups of formula (II').

Preferred polymers comprise at least one group of formula 1, 2 or 3, wherein groups of formulas 1 and 2 are especially preferred.

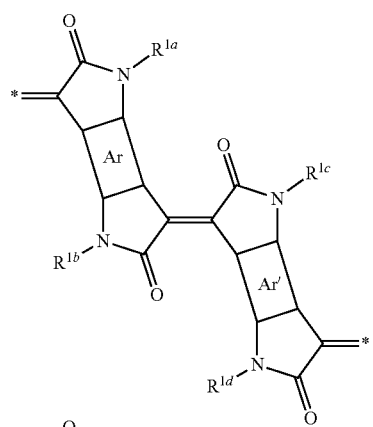

1

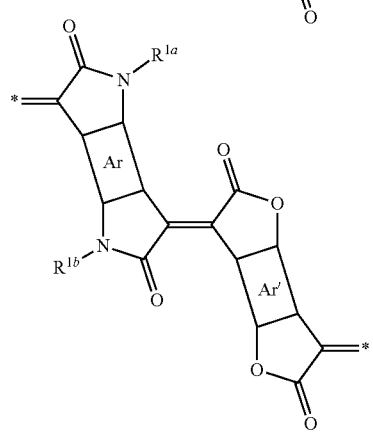

2

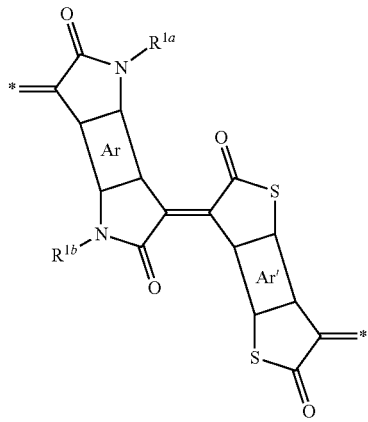

3

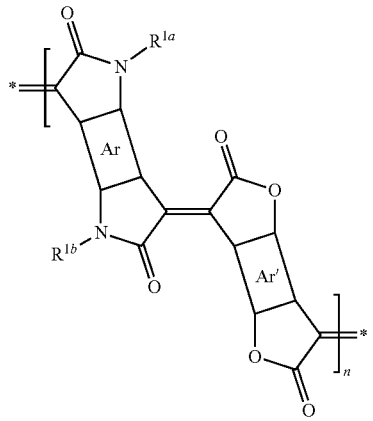

2'

More preferably polymers comprise at least one group of formula 1', 2' or 3', wherein groups of formulas 1' and 2' are especially preferred and n is defined above or below.

Ar and Ar' can be the same.
$R^{1a}$ and $R^{1b}$ can be the same.
$R^{1c}$ and $R^{1d}$ can be the same.
$R^{1a}$, $R^{1b}$, $R^{1c}$ and $R^{1d}$ can be the same.

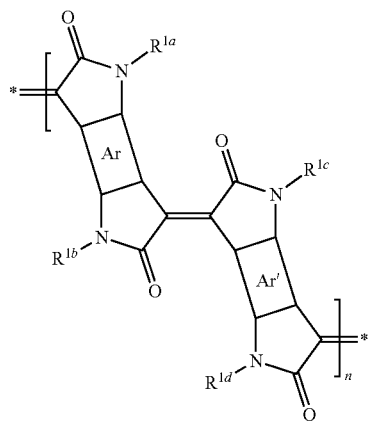

1'

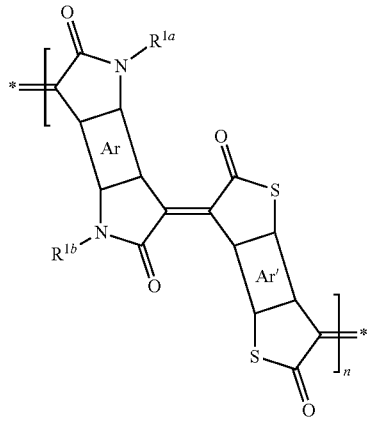

3'

$R^{1b}$, $R^{1c}$ and $R^{1d}$ are defined as $R^{1a}$ above, including the preferred ranges.

The polymers can e.g. be end-capped by moieties $T^1$ or $T^2$.

Very preferred polymers e.g. comprise at least a group

P1

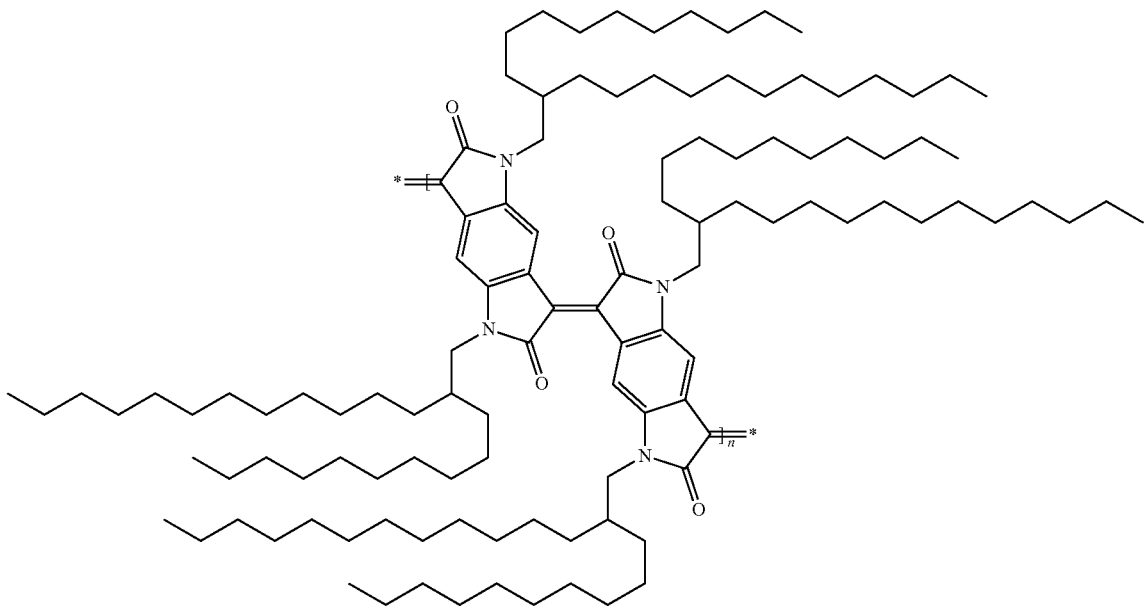

-continued
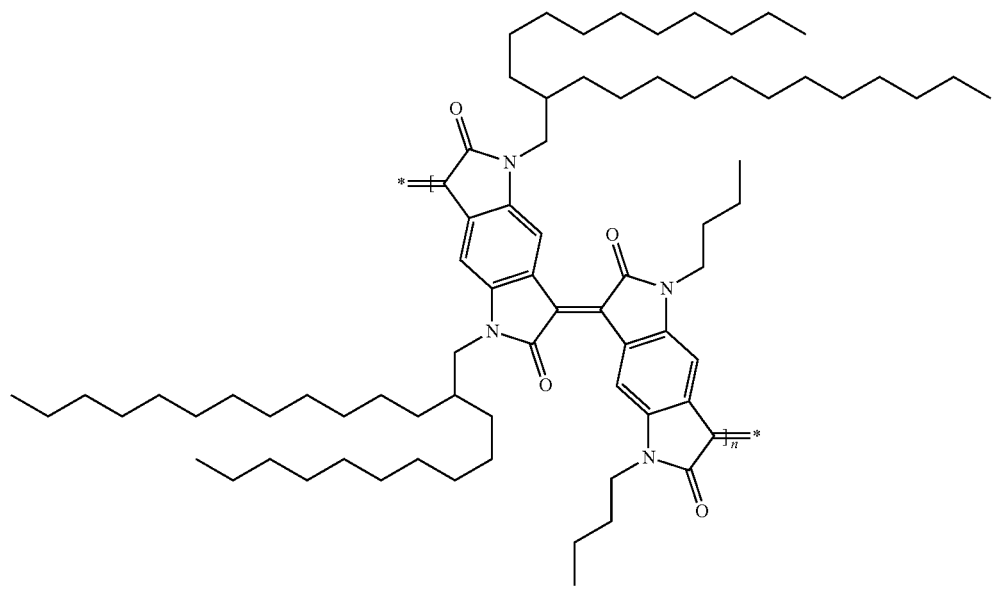
P2
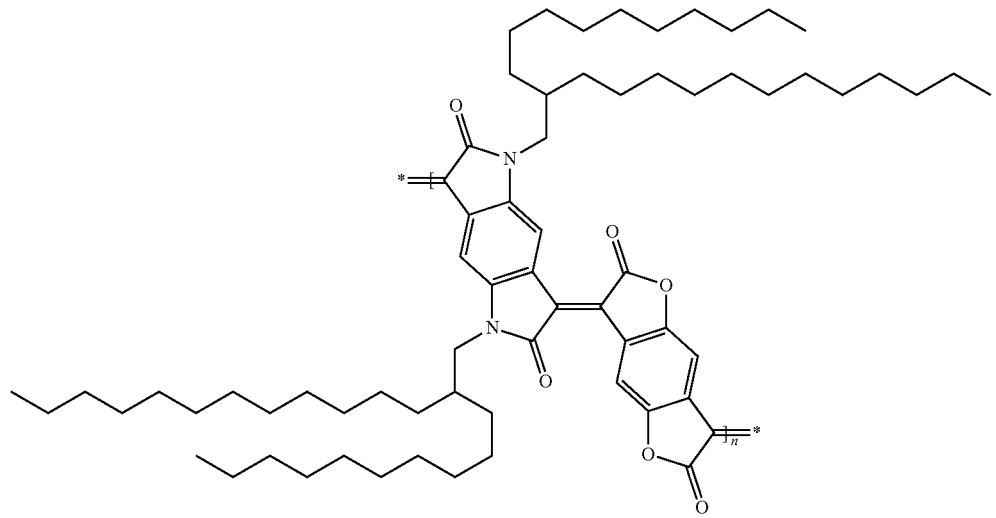
P3
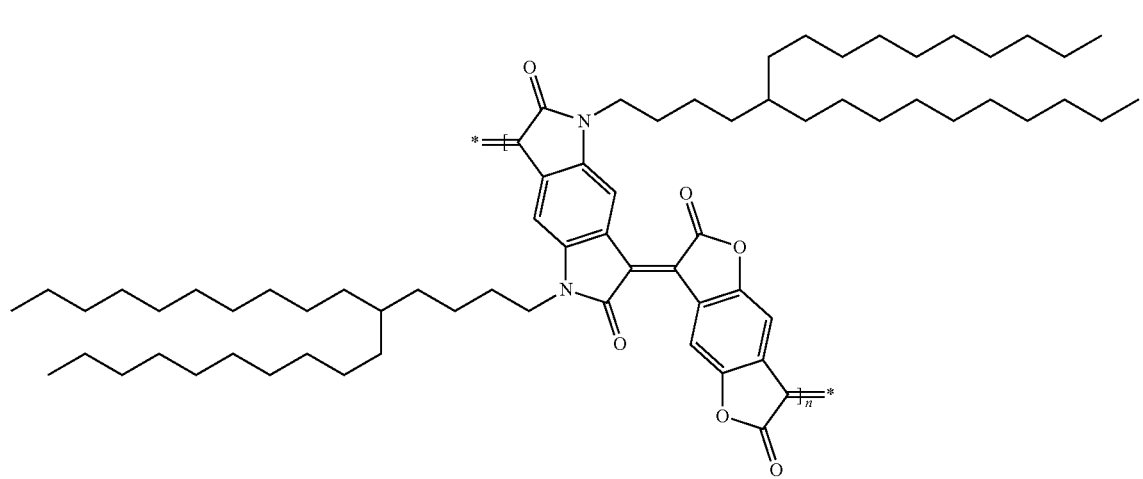
P4

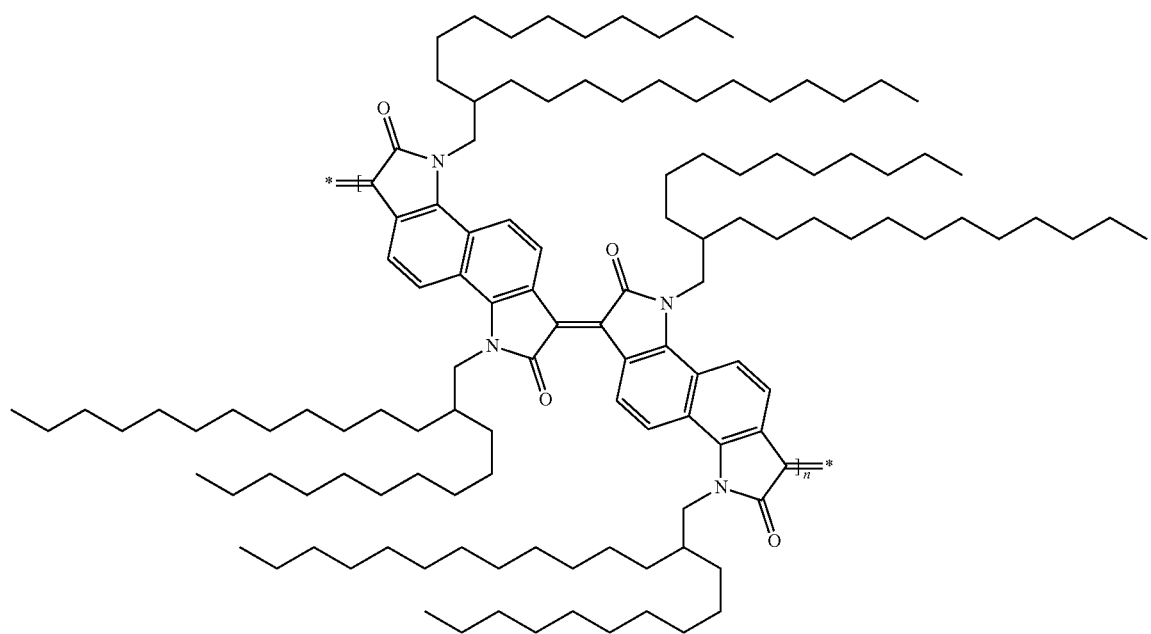
P5
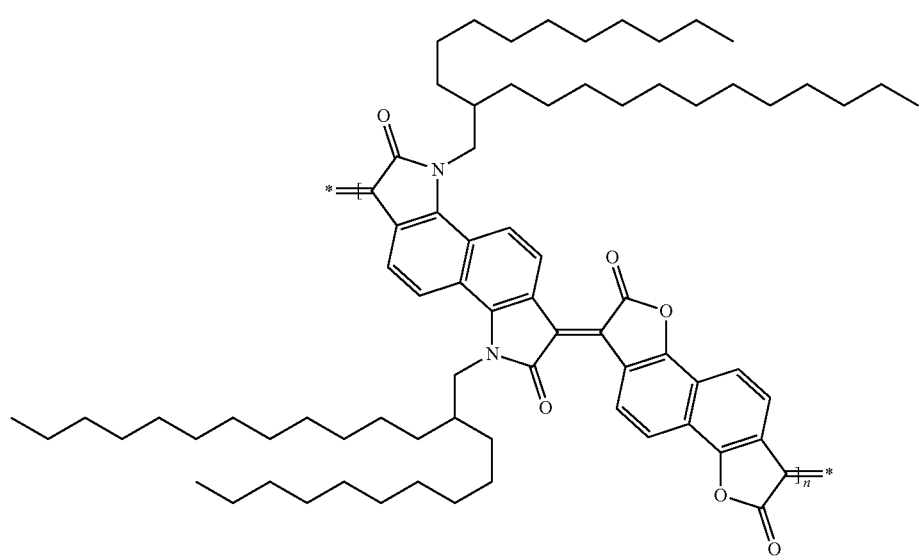
P6

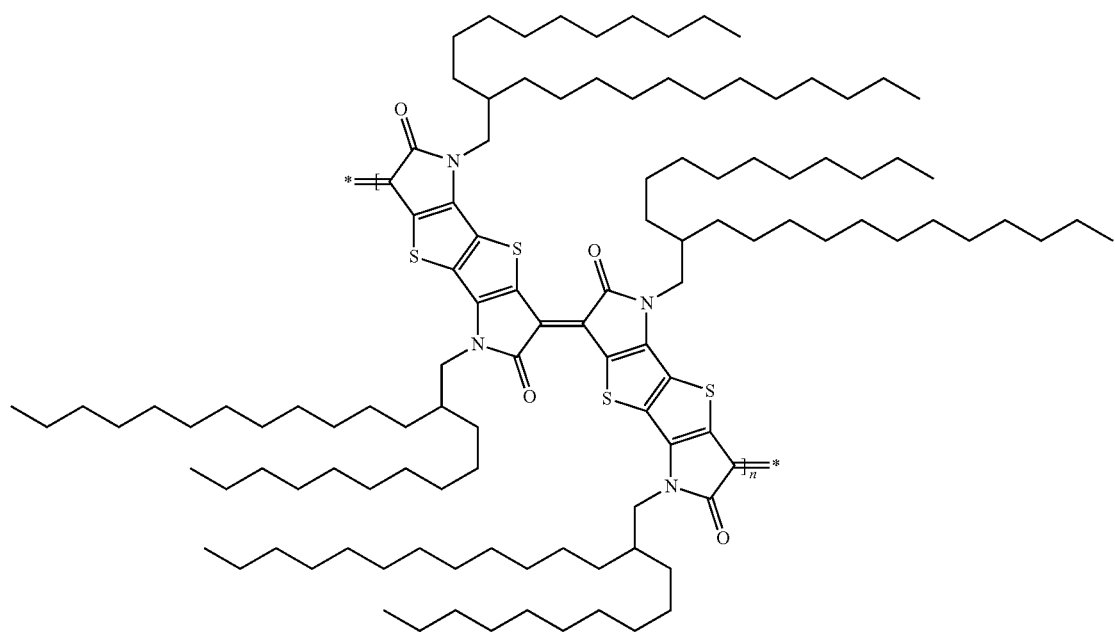
P7
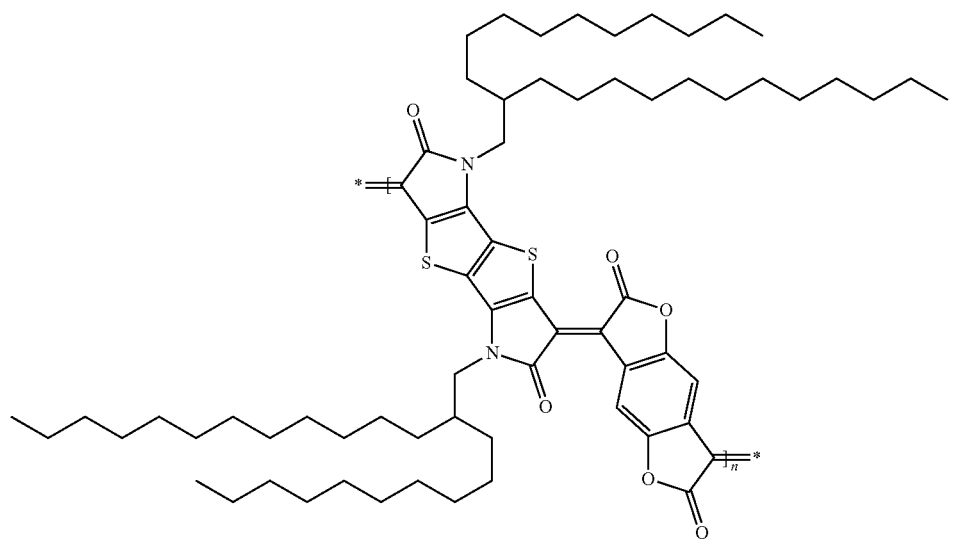
P8
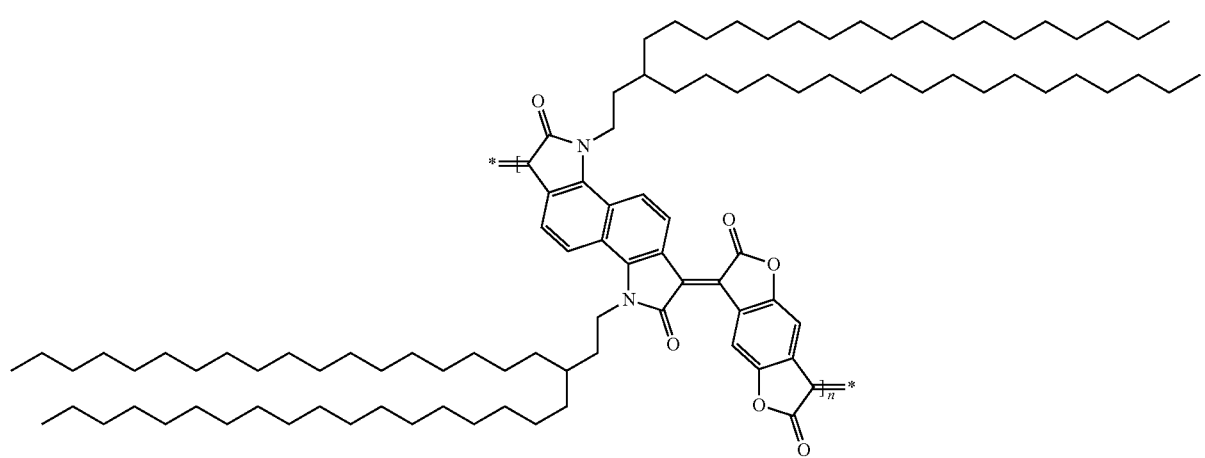
P9

P10
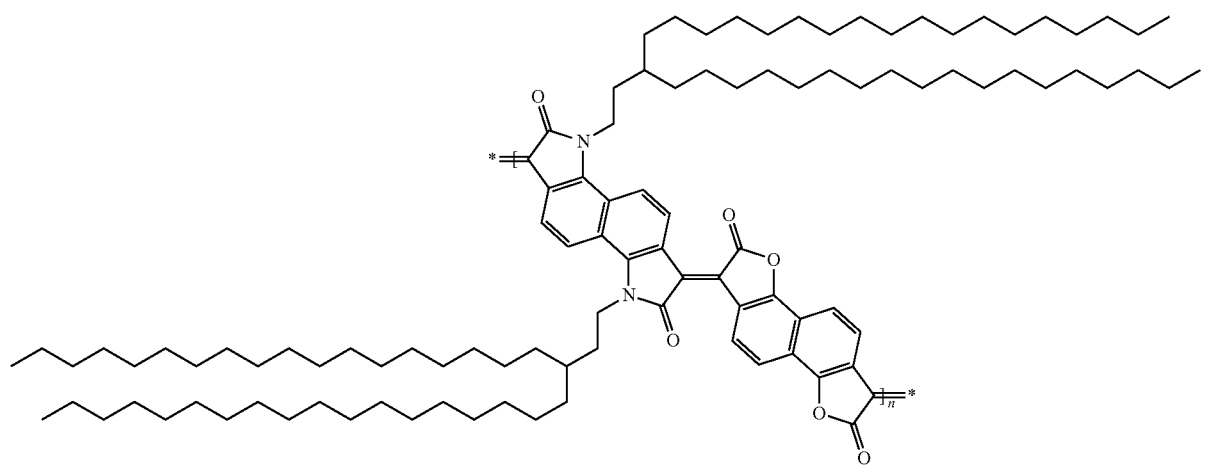
P11
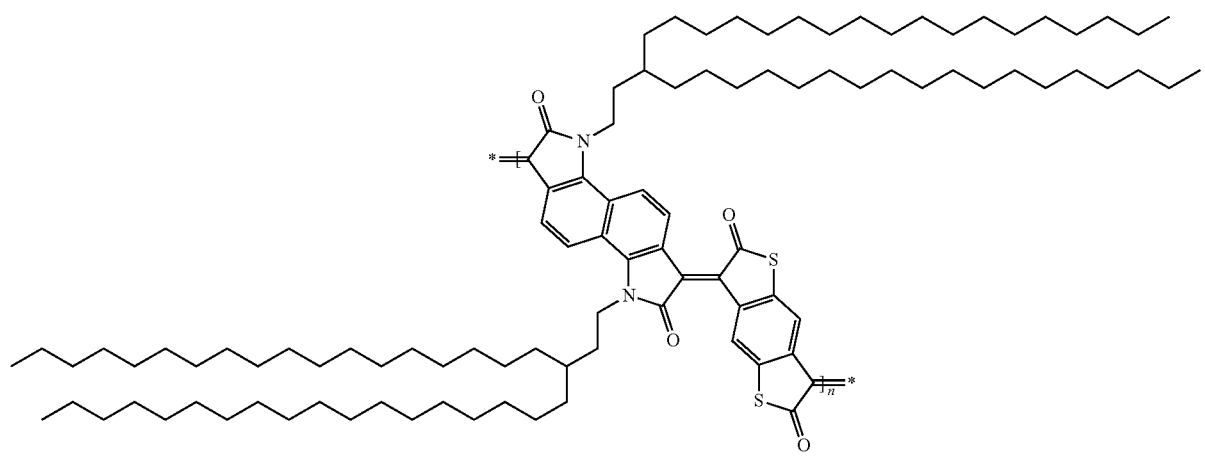
P12
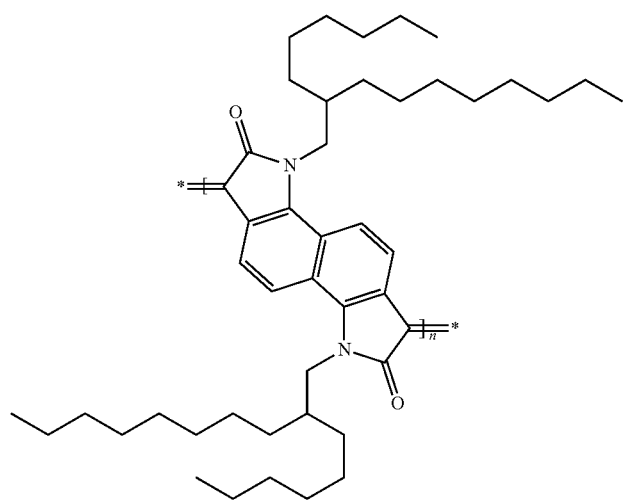

-continued
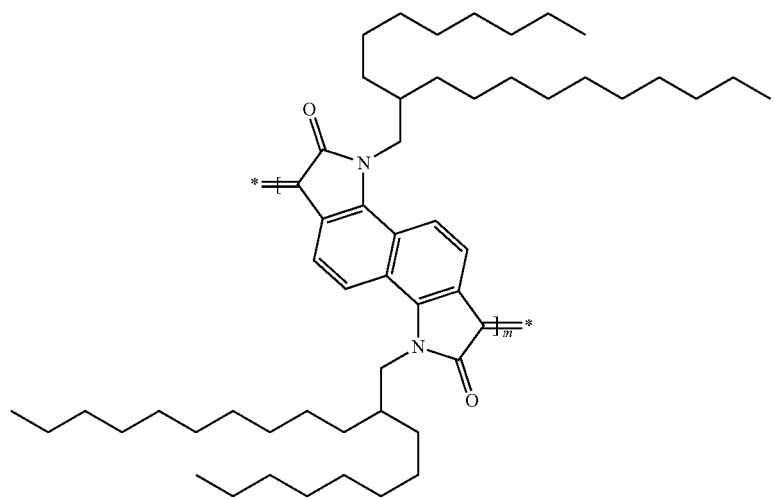
P13
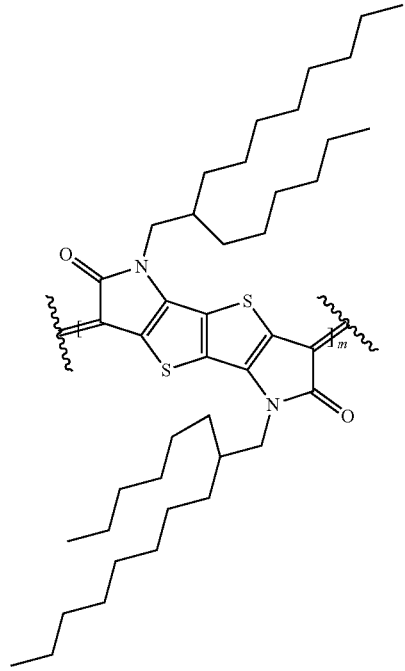
P14 where n is an integer from 3 to 1000 and m is an integer from 3 to 1000.

m is preferably an integer of 4 to 500, more preferably m is 5 to 400, more preferably m is 6 to 300, even more preferably m is 7 to 200 and most preferably m is 8 to 100, especially 10 to 50.

Polymers comprising the formula (II') can be synthesized e.g. via the following synthesis route 1 by condensation of a tetraone A with a dione B:

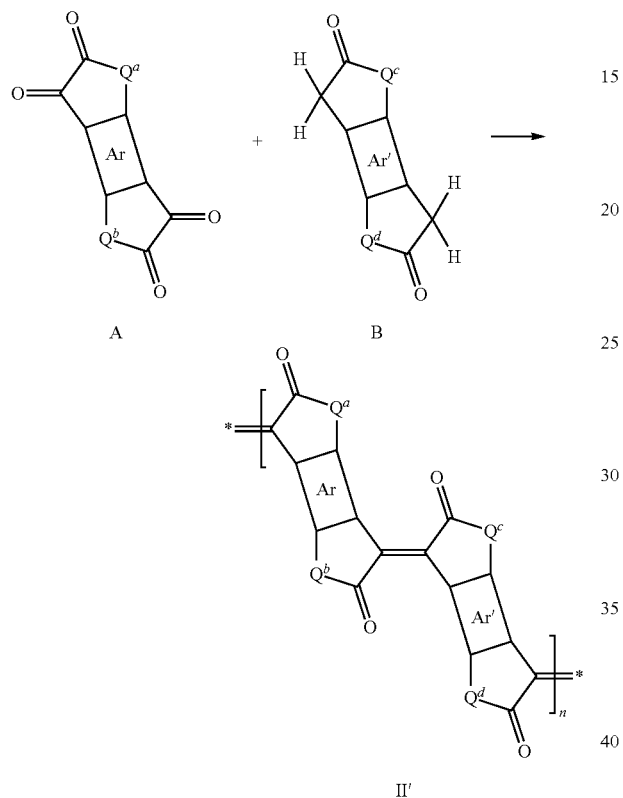

In the case of tetraones A, $Q^a$ and $Q^b$ are preferably substituted nitrogen atoms.

In the case of diones B, $Q^c$ and $Q^d$ are preferably oxygen or substituted nitrogen atoms.

The condensation can be effected in a solvent like acetic acid, toluene, xylene etc. by the application of heat (room temperature up to reflux temperature of the used solvents). Bases or acids, preferably acids can be added as catalysts.

Such bases can be e.g. sodium acetate and sodium hydroxide.

Such acids can be e.g. protic acids like formic acid, acetic acid, propionic acid, trifluoroacetic acid, HCl, $H_2SO_4$, $HPF_6$, para-toluenesulfonic acid, or Lewis acids like $AlCl_3$, preferably protic acids, especially para-toluenesulfonic acid.

The water obtained by the condensation reaction can be removed e.g. by azeotropic distillation with e.g. toluene as solvent, or e.g. with 4 Å molecular sieves. The ends of these polymers are determined by the starting materials A and B. Special end-cappers might be added during the synthesis like e.g.:

preferably

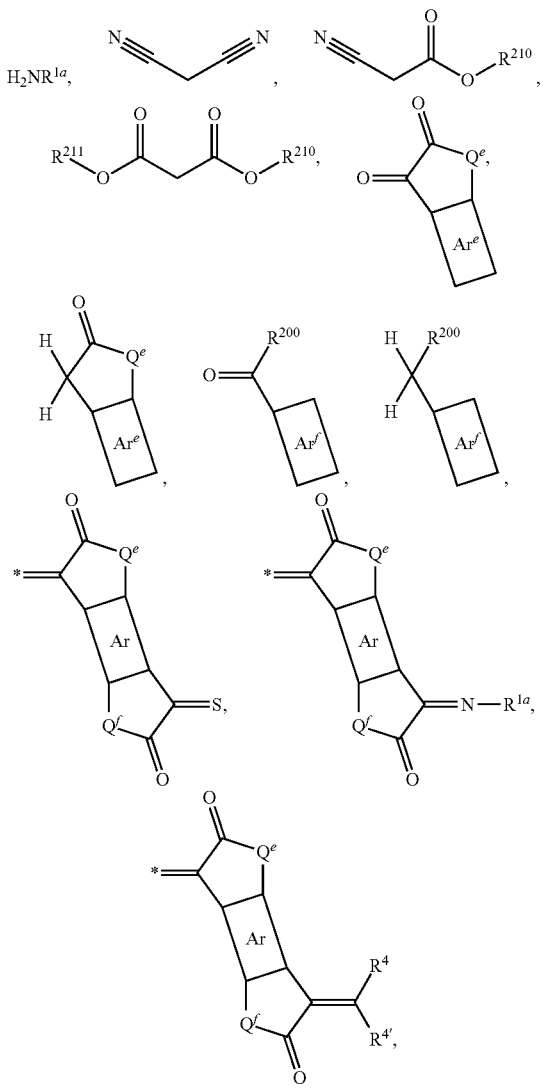

where $R^{210}$ and $R^{211}$ are independently of each other hydrogen, $C_{1-30}$-alkyl, $C_{2-30}$-alkenyl, $C_{2-30}$-alkynyl or $C_{5-12}$-cycloalkyl, preferably $C_{1-30}$-alkyl.

The starting materials A1, A2, B1, B2 wherein $Q^a$, $Q^b$, $Q^c$ and $Q^d$ are substituted nitrogen atoms can e.g. be synthesized as follows by synthesis routes 2 or 3:

Synthesis Route 2:

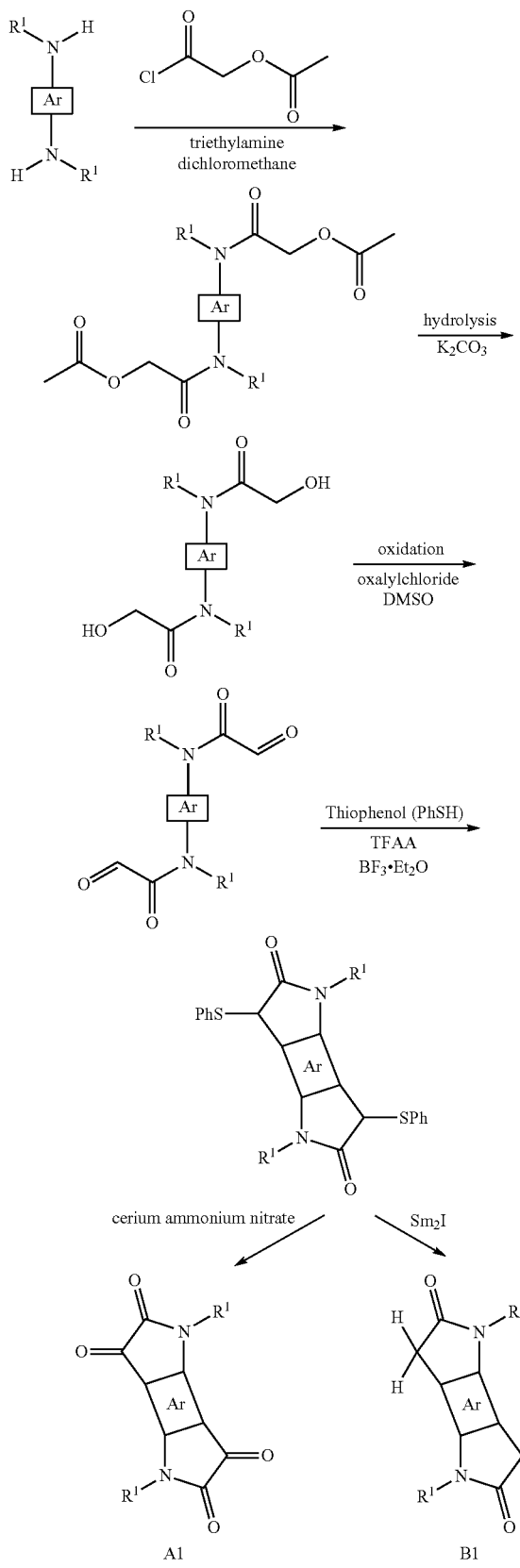

Synthesis Route 3:

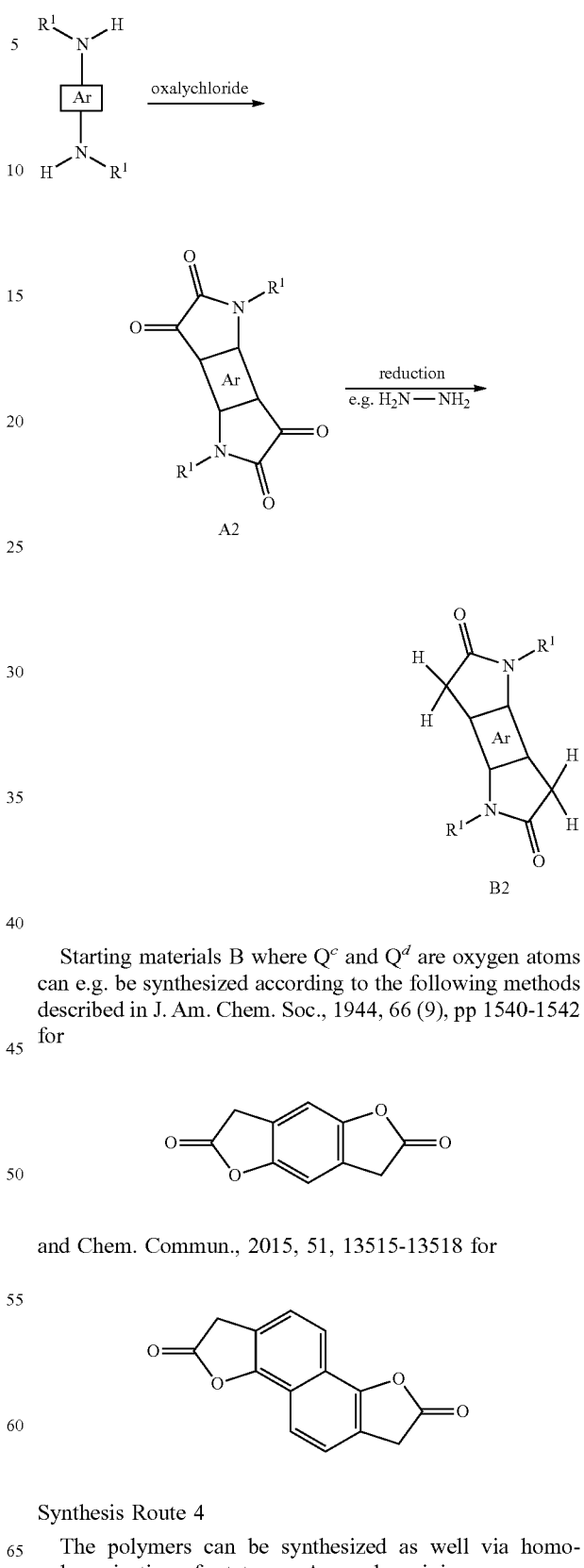

Starting materials B where $Q^c$ and $Q^d$ are oxygen atoms can e.g. be synthesized according to the following methods described in J. Am. Chem. Soc., 1944, 66 (9), pp 1540-1542 for

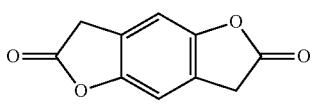 [SMILES: O=C1Cc2cc3c(cc2O1)CC(=O)O3]

and Chem. Commun., 2015, 51, 13515-13518 for

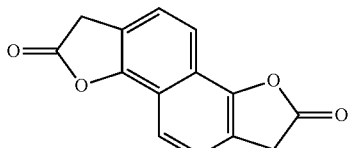

Synthesis Route 4

The polymers can be synthesized as well via homopolymerization of a tetraone A, e.g. by mixing a monomer A with the reagent $P(NEt_2)_3$ in a solvent, e.g. in toluene:

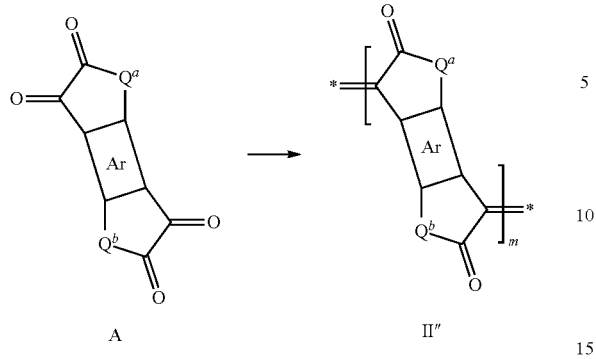

where m is an integer from 3 to 1000.

The invention also relates to electronic devices comprising the compounds or the polymers of the invention, especially organic field effect transistors.

The invention is illustrated by the following non-limiting examples.

EXAMPLES

The scheme for the synthetic route to 1,5-bis(2-decyltetradecyl)-5,7-dihydropyrrolo[2,3-f]indole-2,6(1H,3H)-dione and 1,5-bis(2-decyltetradecyl)-1,5-dihydropyrrolo[2,3-f]indole-2,3,6,7-tetraone is shown below.

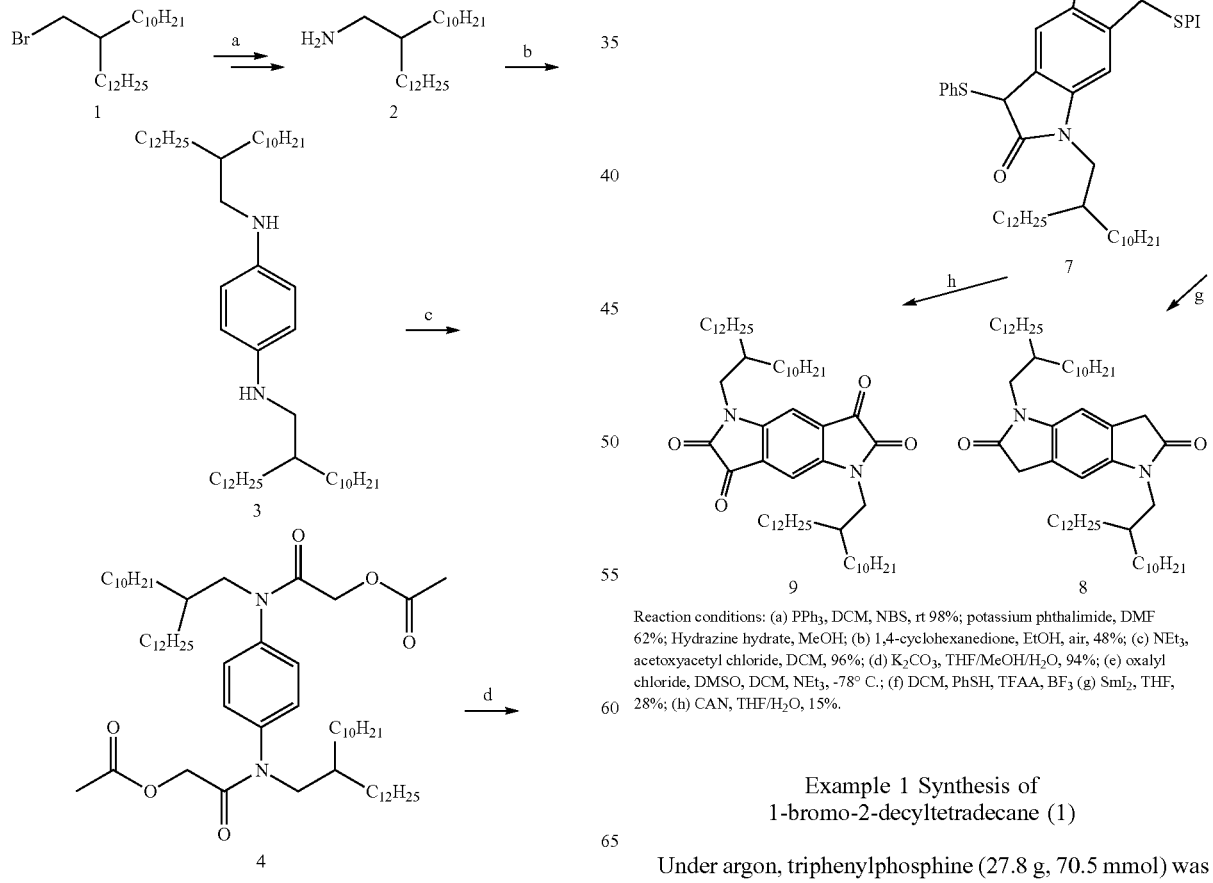

Reaction conditions: (a) PPh₃, DCM, NBS, rt 98%; potassium phthalimide, DMF 62%; Hydrazine hydrate, MeOH; (b) 1,4-cyclohexanedione, EtOH, air, 48%; (c) NEt₃, acetoxyacetyl chloride, DCM, 96%; (d) K₂CO₃, THF/MeOH/H₂O, 94%; (e) oxalyl chloride, DMSO, DCM, NEt₃, -78° C.; (f) DCM, PhSH, TFAA, BF₃ (g) SmI₂, THF, 28%; (h) CAN, THF/H₂O, 15%.

Example 1 Synthesis of 1-bromo-2-decyltetradecane (1)

Under argon, triphenylphosphine (27.8 g, 70.5 mmol) was suspended in a flask with DCM (47 ml). The mixtures was cooled to 0° C. before 2-decyltetradecan-1-ol (29.8 ml, 105.8 mmol) was introduced. After 5 minutes stirring, N-bromosuccinimide (18.8 g, 105.8 mmol) was added portion wise to the flask. The reaction mixture immediately turned yellow and continued to darken to orange. The reaction was stirred for 16 hours after which the solvent was removed by vacuum evaporation. The brown residue was diluted with petroleum ether and the solution flushed through a silica plug. The filtrate was evaporated to give a clear oil. Yield: 28.7 g, 98%. $^1$H NMR (400 MHz, Chloroform-d) δ 3.44 (d, J=4.7 Hz, 2H), 1.66-1.47 (m, 2H), 1.44-1.15 (m, 40H), 0.88 (t, J=6.6 Hz, 7H). $^{13}$C NMR (101 MHz, CDCl$_3$) δ 39.72, 39.70, 32.75, 32.10, 29.97, 29.82, 29.77, 29.53, 26.74, 22.86, 14.26.

Example 2 Synthesis of 2-(2-decyltetradecyl)isoindoline-1,3-dione

A solution of 1-bromo-2-decyltetradecane (20.0 g, 48.0 mmol) and potassium phthalimide (9.98 g, 52.8 mmol) in DMF (57.2 ml) was refluxed for 16 hours. The reaction mixture was cooled to room temperature and poured into water. The aqueous phase was extracted with DCM three times. The combined organic phase was washed with 0.2 M KOH, followed by H$_2$O and NH$_4$Cl. After drying the organic phase with MgSO$_4$ and filtering the salt, the solvent was removed under vacuum. The residue was subjected to a silica plug using 10% EtOAc in petroleum ether, the yellow oil (14.4 g, 62%) obtained was used immediately.

Example 3 Synthesis of 2-decyltetradecan-1-amine (2)

51% Hydrazine hydrate in water (5.00 ml, 3.1 mmol) was introduced to a solution of 2-(2-decyltetradecyl)isoindoline-1,3-dione (14.40 g, 29.80 mmol) in methanol (10 ml) and refluxed for 16 hours. After cooling, the solvent was removed under vacuum before DCM and 10% KOH solution was added to the residue. The phases were separated and the aqueous phase further extracted with DCM three times. The combined organic phase was washed with brine, dried over MgSO$_4$, filtered and the solvent removed under reduced pressure. Pale yellow oil, yield 10.0 g, 94% was obtained. $^1$H NMR (400 MHz, Chloroform-d) δ 3.51 (d, J=5.5 Hz, 2H), 1.54-1.38 (m, 1H), 1.37-1.17 (m, 40H), 0.94-0.78 (m, 6H). $^{13}$C NMR (101 MHz, CDCl$_3$) δ 150.50, 108.43, 45.34, 41.01, 36.21, 32.06, 31.67, 30.25, 29.82, 29.49, 27.96, 26.92, 22.82, 14.23. MS TOF ES+: calculated 354.4100, [M+H]$^+$, C24H51N, found 354.4111.

Example 4 Synthesis of N,N'-bis(2-decyltetradecyl) benzene-1,4-diamine (3)

1,4-Cyclohexanedione (0.6 g, 5.0 mmol) was dissolved in ethanol and 2-decyltetradecan-1-amine added to the solution. Air was bubbled through the reaction mixture for 2 hours before the solvent was removed under reduced pressure. The red residue was purified on basified silica gel using 3% EtOAc in petroleum ether to yield 1.8 g, 46% brown oil. $^1$H NMR (400 MHz, Chloroform-d) δ 6.54 (s, 4H), 3.24-2.71 (m, 4H), 1.57 (s, 2H), 1.26 (s, 80H), 0.88 (t, J=6.7 Hz, 12H). 13C NMR (101 MHz, CDCl3) δ 141.18, 114.77, 49.07, 37.95, 32.33, 32.09, 30.25, 29.82, 29.52, 26.90, 22.85, 14.27. MS TOF ES+: calculated 781.8278 [M+H]$^+$, C54H104N2, found 781.8269.

Example 5 Synthesis of benzene-1,4-diylbis{[(2-decyltetradecyl)imino]-2-oxoethane-2,1-diyl} diacetate (4)

Triethylamine (0.70 ml, 4.99 mmol) was added to N,N'-bis(2-decyltetradecyl)benzene-1,4-diamine (1.77 g, 2.27 mmol) dissolved in dry DCM (22.70 ml) at O ° C. Acetoxyacetyl chloride (0.54 ml, 4.99 mmol) was injected into the flask drop wise before the reaction was allowed to warm to room temperature and stirred for 16 hours. The reaction was quenched with NaHCO$_3$ and EtOAc added. The phases were separated and the aqueous phase extracted three times with EtOAc. The combined organic phase was washed with brine dried over MgSO$_4$, the salts filtered and the solvent removed under pressure to give pale yellow solid, 2.00 g, 96%. 1H NMR (400 MHz, Chloroform-d) δ 7.32 (s, 4H), 4.33 (s, 4H), 3.64 (d, J=7.0 Hz, 4H), 2.12 (s, 6H), 1.53-1.41 (m, 2H), 1.37-1.02 (m, 80H), 0.94-0.79 (m, 12H). 13C NMR (101 MHz, CDCl3) δ 170.61, 166.56, 141.13, 129.79, 61.79, 53.41, 36.25, 32.06, 31.23, 30.15, 29.82, 29.75, 29.50, 26.39, 22.83, 20.65, 14.25. MS TOF LD+: C62H112N2O6 [M+H]$^+$ found 980.9.

Example 6 Synthesis of N,N'-benzene-1,4-diylbis [N-(2-decyltetradecyl)-2-hydroxyacetamide] (5)

Benzene-1,4-diylbis{[(2-decyltetradecyl)imino]-2-oxoethane-2,1-diyl} diacetate (3.6 g, 3.7 mmol) in THF (200 ml) and MeOH/water mixture (180 ml, 20 ml). The reaction mixture was stirred in the presence of excess K$_2$CO$_3$ at room temperature for 16 hours before the salt was filtered off. The mixture was concentrated under reduced pressure and water and ethyl acetate added to the residue. The phases were separated and the aqueous phase is extracted three times with ethyl acetate. The combined organic phases were washed with brine dried over MgSO$_4$, filtered and the solvent removed in the rotary evaporator to furnish light yellow, 3.1 g, 94%. $^1$H NMR (400 MHz, Chloroform-d) δ 7.24 (s, 4H), 3.76 (s, 4H), 3.70 (d, J=7.1 Hz, 4H), 3.47-3.30 (m, 2H), 1.52-1.37 (m, 2H), 1.36-1.04 (m, 80H), 0.86 (t, J=6.7 Hz, 12H). $^{13}$C NMR (101 MHz, CDCl$_3$) δ 171.98, 140.31, 129.69, 60.73, 53.47, 36.21, 32.04, 31.23, 30.11, 29.77, 29.71, 29.47, 26.38, 22.80, 14.22. MS TOF LD+: C58H108N2O4, [M+H]$^+$ found 898.00.

Example 7 Synthesis of N,N'-(1,4-phenylene)bis(N-(2-decyltetradecyl)-2-oxoacetamide) (6)

Under argon atmosphere, oxalyl chloride (0.31 ml, 3.89 mmol) was diluted with DCM (4 ml) and cooled to −78° C. A solution of DMSO (0.28 ml) in DCM (4.2 ml) was added to the reaction flask at −78° C. The reaction flask was stirred for 20 minutes before N,N'-benzene-1,4-diylbis[N-(2-decyltetradecyl)-2-hydroxyacetamide] (1.45 g, 1.62 mmol) diluted in 7 ml DCM was injected dropwise into the flask. The reaction mixture turns aqua green. After 1.5 hours at −78° C., trimethylamine (2.26 ml, 16.2 mmol) was added slowly. The reaction was then stirred at −78° C. for 4 hours before it was allowed to warm to room temperature slowly. The reaction was stirred for 16 hours before it was quenched with saturated NaHCO$_3$ solution. The phases were separated and the aqueous phase extracted three times with DCM. The combined organic phases were dried with MgSO$_4$, filtered and the solvent removed under vacuum to yield brown oil, 0.61 g, which was used immediately.

Example 8 Synthesis of 1,5-bis(2-decyltetradecyl)-3,7-bis(phenylthio)-5,7-dihydropyrrolo[2,3-f]indole-2,6(1H,3H)-dione (7)

Crude N,N'-(1,4-phenylene)bis(N-(2-decyltetradecyl)-2-oxoacetamide) (1.44 g, 1.61 mmol) was diluted with DCM (6 ml) before thiophenol (0.33 ml, 3.23 mml) was added to flask. The reaction mixture was then stirred for 16 hours at room temperature. Following this, TFAA (2.01 ml, 14.50 mmol) was added slowly to the reaction and stirred for 1 hour 30 minutes, after which, $BF_3 \cdot Et_2O$ (0.99 ml, 8.05 mmol) was added to the flask cautiously. Following further stirring for 3 hours, the reaction was cooled to 0° C. before it was quenched with $NaHCO_3$. The aqueous phase was extracted with DCM three times and the organic phases combined and washed with brine and dried over $MgSO_4$. The solvent was removed under reduced pressure to furnish red/brown residue as the crude product, which was used without further purification. Yield (1.32 g, 76%) MS (TOF ES+): calculated 1077.8244 $C_{70}H_{112}N_2O_2S_2$, [M+H]+ found 1077.8278.

Example 9 Synthesis of 1,5-bis(2-decyltetradecyl)-1,5-dihydropyrrolo[2,3-f]indole-2,3,6,7-tetraone (9)

Cerium ammonium nitrate (9.48 g, 17.8 mmol) was added to the solution of 1,5-bis(2-decyltetradecyl)-3,7-bis(phenylthio)-5,7-dihydropyrrolo[2,3-f]indole-2,6(1H,3H)-dione (2.40 g, 2.22 mmol) dissolved in a 6:1 ratio of THF/water (42 ml) mixture. Following 30 minutes stirring at room temperature the reaction mixture takes a deep purple colouration. After 3 hours stirring the reaction mixture was reduced under vacuum. The crude residue was purified by column chromatography at a gradient of 3-10% ethyl acetate in petroleum ether 40-60° C. to furnish the titled compound, yield: 300 mg, 15%. $^1$H NMR (400 MHz, Chloroform-d) δ 7.12 (s, ArH, 2H), 3.62 (d, J=7.5 Hz, $NCH_2$, 4H), 1.84 (d, J=9.9 Hz, CH, 2H), 1.40-1.12 (m, $CH_2$, 80H), 0.88 (t, J=6.7 Hz, $CH_3$, 12H). $^{13}$C NMR (101 MHz, $CDCl_3$) δ 183.36, 157.15, 147.85, 123.24, 106.99, 77.16, 45.49, 36.15, 32.06, 31.52, 30.12, 29.79, 29.76, 29.69, 29.47, 26.40, 22.82, 14.25. MS TOF LD+: $C_{58}H_{100}N_2O_4$, [M+H]$^+$ found 890.0.

Example 10 Synthesis of 1,5-bis(2-decyltetradecyl)-5,7-dihydropyrrolo[2,3-f]indole-2,6(1H,3H)-dione (8)

1,5-bis(2-decyltetradecyl)-3,7-bis(phenylthio)-5,7-dihydropyrrolo[2,3-f]indole-2,6(1H,3H)-dione was dissolved in dry THF (37.0 ml) and 0.1 M $SmI_2$ in THF (40.0 ml, 4.0 mol) added to the solution at room temperature. Following 16 hours, saturated $NaHCO_3$ (200 ml) was introduced into the reaction mixture and the aqueous phase extracted with ethyl acetate three times. The organic layer was washed with brine, dried over $MgSO_4$, filtered and the solvent removed under reduced pressure. Purification by column chromatography in 15% ethyl acetate in 40-60° C. petroleum ether afforded 800 mg beige solid; yield: 28%. 1H NMR (400 MHz, Chloroform-d) δ 6.73 (s, 2H), 3.56 (d, J=7.9 Hz, ArH 4H), 3.54 (s, $CH_2$, 4H), 1.91-1.76 (m, CH, 2H), 1.24 (s, $CH_2$, 80H), 0.87 (t, $CH_3$, J=6.7 Hz, 12H). $^{13}$C NMR (101 MHz, $CDCl_3$) δ 174.85, 140.24, 123.92, 106.05, 44.85, 36.41, 36.25, 32.06, 31.68, 30.20, 29.81, 29.49, 26.60, 22.83, 14.26. MS TOF LD+: $C_{58}H_{104}N_2O_2$ [M+H]$^+$ found 860.9.

Example 11 Polymerization to Give pDPID P1

A microwave vial was charged with 1,5-bis(2-decyltetradecyl)-5,7-dihydropyrrolo[2,3-f]indole-2,6(1H,3H)-dione (8) (50.0 mg, 0.06 mmol), 1,5-bis(2-decyltetradecyl)-1,5-dihydropyrrolo[2,3-f]indole-2,3,6,7-tetraone (9) (51.6 mg, 0.06 mmol), p-toluene sulfonic acid (3.3 mg, 0.02 mmol) and 4 Å molecular sieves. The vial was sealed and dry toluene (2 ml), already degassed for 30 minutes was injected into the vial. The reaction was heated at 120° C. for 21 hours followed by 10 hours at 180° C. in the dark. The reaction mixture changed colour from blue to red/brown to dark purple over the polymerization period. The crude polymer was precipitated in methanol and purified by Soxhlet extraction with methanol, acetone, and hexane. The hexane fraction was collected and reduced under vacuum and the polymer precipitated into methanol. The polymer was filtered and dried. Yield of P1: 83 mg, 82% dark purple solid. $^1$H NMR (400 MHz, Chloroform-d) δ 9.30 (d, J=8.2 Hz, 2H), 8.93 (s, 2H), 7.11 (d, J=8.2 Hz, 2H), 3.75 (dd, J=13.6, 7.3 Hz, 8H), 2.02 (dt, J=12.8, 6.1 Hz, 4H), 1.66-1.12 (m, 150H), 0.91-0.79 (m, J=3.7 Hz, 24H).

$M_n$=18 400 g/mol, $M_w$=29 900 g/mol, PDI=1.6

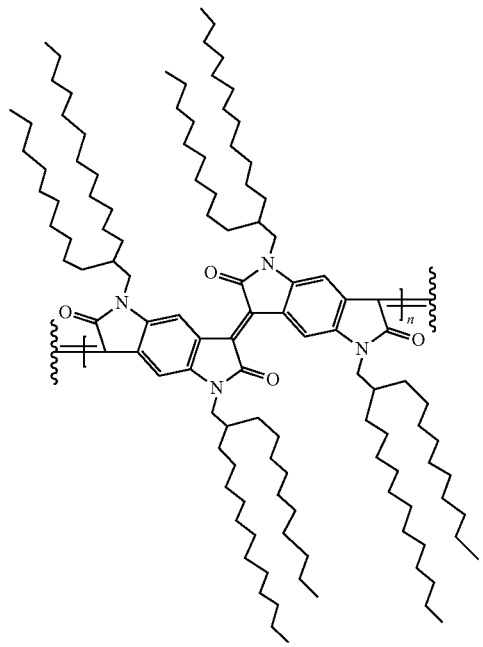

P1

Example 12

Fabrication and Electrical Characterization of an Organic Field-Effect Transistor (OFET) Based on Compound P1
Preparation of Back-Contact, Top-Gate FETs Compound P1 is dissolved at a concentration of 0.75 wt % in toluene. The transistors have been fabricated on a PET-substrate with lithographically prepatterned gold contacts, serving as Source and Drain contact of the FET. Before the deposition of the semiconductor, the substrate been immersed in a 1 wt % solution of 4-methoxybenzenethiol in ethanol for 2 minutes. Afterwards the substrate has been rinsed with ethanol and blown dry using nitrogen. Next, the semiconductor formulation was applied by spin coating (1,000 rpm, 15 seconds). After the coating is completed, the substrate is immediately transferred onto a preheated hotplate and heated for 30 s at 90° C. Next the gate dielectric layer consisting of Cytop CTL-809 M is spincoated on top of the organic semiconductor (1250 rpm, 30 s). After Spin-coating, the substrate is again transferred to the hotplate and annealed for another 5 Min at 90° C. The thickness of the dielectric layer is 500 nm measured by profilometer. Finally 50 nm thick shadow-mask patterend gold gate electrodes are deposited by vacuum evaporation to complete FETs in the BCTG-configuration.

Electrical Characterization

The devices obtained are showing n-type characteristics. The mobility is calculated from the root representation of the transfer characteristic curve (solid grey curve) calculated in the saturation region. The slope m is determined from the dashed black line in FIG. 1. The dashed black line in FIG. 1 is fitted to a region of the root representation of the current characteristic ID such that a good correlation to the linear slope of the root representation is obtained. The threshold voltage $U_{Th}$ can be taken from the intersection of black dashed line in FIG. 1 with the X-axis portion ($V_{GS}$).

In order to calculate the electrical properties of the OFET, the following equations are employed:

$$\mu = \frac{m^2 * 2L}{C_G * W} \quad C_G = \varepsilon_0 * \varepsilon_r \frac{1}{d} \quad U_{Th} = -1 * \frac{m}{b} \quad ON/OFF = \frac{I_D \max}{I_D \min}$$

where $\varepsilon_0$ is the vacuum permittivity of $8.85 \times 10^{-12}$ As/Vm, $\varepsilon_r$=2.1 for Cytop, the thickness of the dielectric d=500 nm, and W/L=25.

The following mobility has been calculated for the respective compound:

| Compound | Field-effect mobility $\mu$ [cm$^2$/Vs] | Threshold voltage $U_{TH}$ [V] | ON/OFF ratio |
|---|---|---|---|
| P1 | 9E−5 | 15 | 2E2 |

FIG. 1 shows a representative transfer characteristics of a FET fabricated from compound P1 with $V_{GS}$=−10 V to +30 V at 0.5V step size with $V_{DS}$=+30V. Drain current (black solid curve), Gate current (dotted grey curve), Square root of drain current (grey solid curve), and fitted slope of square root (dashed black curve).

Example 13

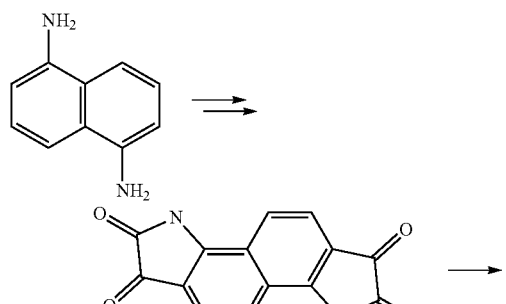

12

-continued

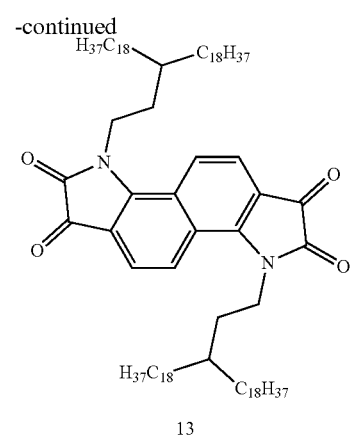

13

Compound 12 was synthesized according to the reference (J. Mater. Chem. A. 2016, 4, 6940-6945), which was used as crude product without purification.

The crude bisisatin 12 (300 mg, 1.13 mmol) and dry K$_2$CO$_3$ (660 mg, 4.78 mmol) and the alkyliodide [1639798-42-7] (2.2 g, 3.26 mmol) were dissolved in 10 mL of dry DMF. The reaction mixture was heated to 100° C. for 4 hours. After cooling down, the reaction mixture was poured over 20 mL H$_2$O. The aqueous layer was extracted with CHCl$_3$. The organic layers were dried over MgSO$_4$ and concentrated to yield the crude reside. The crude product was purified by column chromatography on silica gel (CHCl$_3$:hexane: 2:1) to get the compound 13. Recrystallization with dichloromethane and methanol, collected and dried in vacuum. Total yield: 230 mg (15%). $^1$H NMR (400 MHz, CDCl3, rt): δ=7.99 (d, J=8.7 Hz, 2H), 7.67 (d, J=8.6 Hz, 2H), 4.28-4.24 (m, 4H), 1.79-1.74 (m, 4H), 1.59-1.12 (M, 152H), 0.91-0.88 (m, 12H). $^{13}$C NMR (100 MHz, CDCl3, rt): δ=182.76, 158.96, 152.24, 127.21, 120.08, 119.64, 116.27, 42.12, 35.90, 33.46, 33.16, 31.94, 29.99, 29.72, 29.68, 29.37, 26.63, 22.70, 14.12. Calculated: C92H162N2O. 1359.25, Found: [M+H]: 1360.6.

Example 14 Polymerization to Give pDPID P9

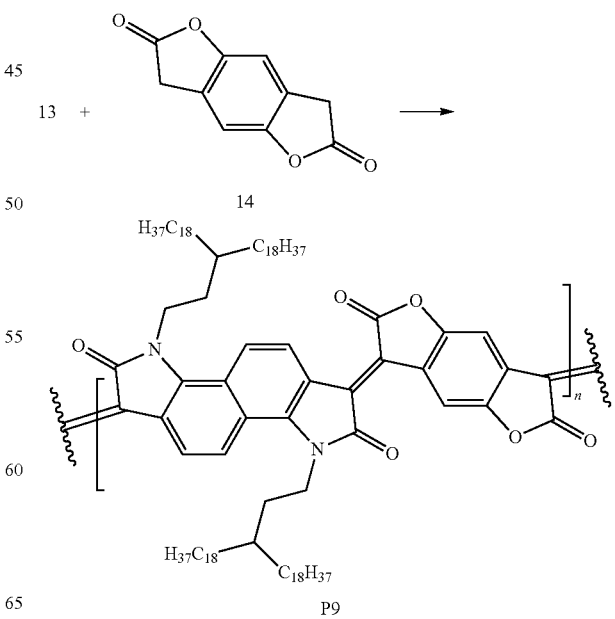

P9

Compound 14 was synthesized according to ref: *J. Am. Chem. Soc.* 2014, 136, 2135-2141. Polymer P9: To a vial was added 13 (71.82 mg, 0.053 mmol, 1 equiv) and bisoxindole 14 (10.04 mg, 0.053 mmol, 1 equiv), PTSA (2 mg). The tube was sealed and flushed with Argon, and then 0.5 ml degassed toluene was added. The mixture was thoroughly degassed under Argon for half an hour, and then the argon inlet was removed. The vial was heated at 120° C. for 3 days. After cooling to RT, the polymer was precipitated into methanol, and filtered through a Soxhlet thimble. The polymer was extracted using Soxhlet apparatus with methanol, acetone, hexane and chloroform. The hexane and chloroform fractions were concentrated and precipitated into methanol. The precipitates were filtered and dried under vacuum to afford P9 as a dark solid (59 mg, 73%). GPC (chlorobenzene, 80° C.): Mn: 25.2 KDa, Mw: 44.3 KDa, PDI=1.76. $^1$H-NMR (TCE-d$_2$, 403 K, 400 Hz): δ=9.04 (broad), 7.76 (broad), 4.34 (broad), 2.18-0.85 (m).

Example 15 Polymerization to Give pDPID P10

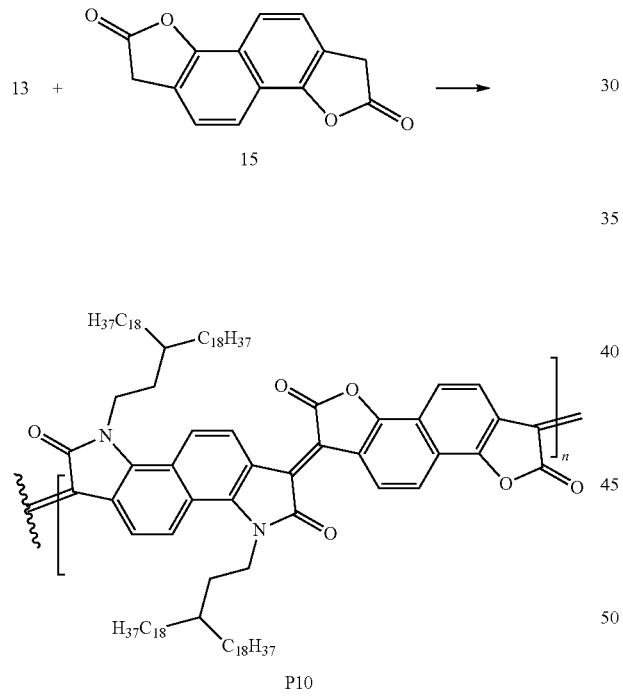

Compound 15 was synthesized according to the ref: *Chem. Commun.*, 2015, 51, 13515. Polymer P10: To a vial was added 13 (52.78 mg, 0.039 mmol, 1 equiv.) and bisoxindole 15 (9.32 mg, 0.039 mmol, 1 equiv), PTSA (2 mg). The tube was sealed and flushed with Argon, and then 0.5 ml degassed toluene was added. The mixture was thoroughly degassed under Argon for half an hour, and then the argon inlet was removed. The vial was heated at 120° C. for 3 days. After cooling to RT, the polymer was precipitated into methanol, and filtered through a Soxhlet thimble. The polymer was extracted using Soxhlet apparatus with methanol, acetone, hexane and chloroform. The hexane and chloroform fractions were concentrated and precipitated into methanol. The precipitates were filtered and dried under vacuum to afford P10 as a dark solid (47 mg, 77%). GPC (chlorobenzene, 80° C.): Mn: 10.5 k, Mw: 15.7 K, PDI: 1.49. $^1$HNMR (TCE-d2, 403 K, 400 Hz): δ=9.33 (d), 9.20 (d), 9.10 (d), 8.05-7.94 (m), 7.71 (d), 7.64 (d), 4.41-4.27 (m), 1.98-1.82 (m), 1.38-0.94 (m).

Example 16 Polymerization to Give pDPID P11

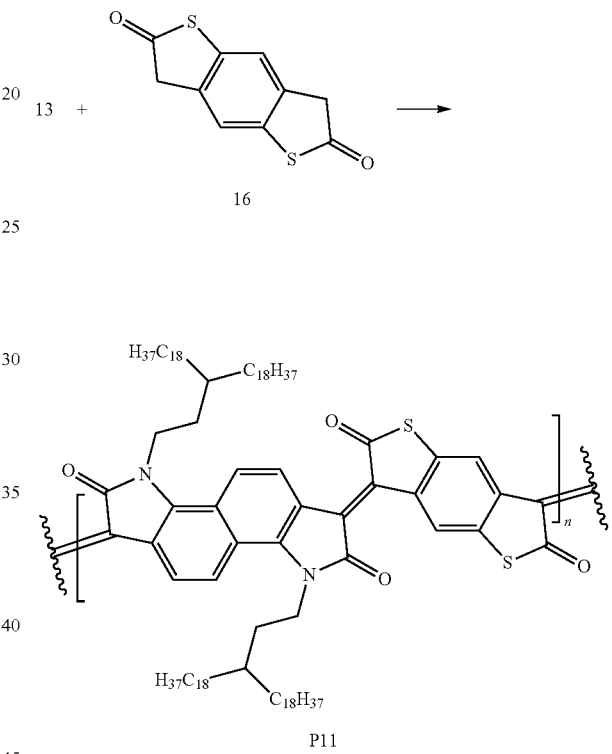

Compound 16 was synthesized according to the ref: *Organic Electronics* 37 (2016) 190-196. Polymer P11: To a vial was added 13 (80.95 mg, 0.0595 mmol, 1 equiv.) and bisoxindole 16 (24.39 mg, 0.04 mmol, 1 equiv), PTSA (4 mg). The tube was sealed and flushed with Argon, and then 0.7 ml degassed toluene was added. The mixture was thoroughly degassed under Argon for half an hour, and then the argon inlet was removed. The vial was heated at 120° C. for 3 days. After cooling to RT, the polymer was precipitated into methanol, and filtered through a Soxhlet thimble. The polymer was extracted using Soxhlet apparatus with methanol, acetone, hexane and chloroform. The hexane and chloroform fractions were concentrated and precipitated into methanol. The precipitates were filtered and dried under vacuum to afford P11 as a dark solid (65 mg, 70%). GPC (chlorobenzene, 80° C.): Mn=21.1 K, Mw=31.2 K, PDI=1.48. $^1$HNMR (TCE-d$_2$, 403 K, 400 Hz): δ=8.71 (broad), 8.01 (broad), 7.57 (broad), 4.33 (broad), 2.12-0.76 (m).

Example 17

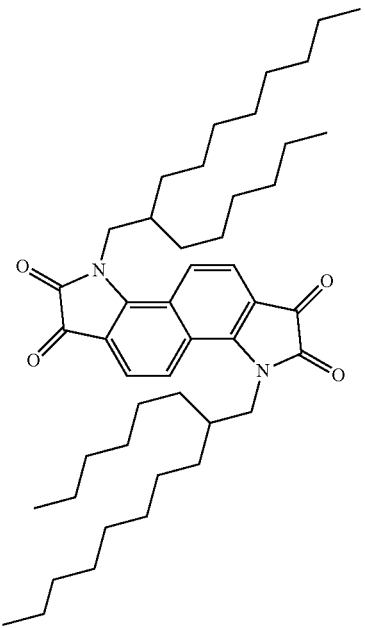

17

Compound 17 was synthesized according to compound 13 in example 13 with [1044598-79-9] as alkyl iodide instead of [1639798-42-7].

Example 18 Polymerization to Give pDPID P12

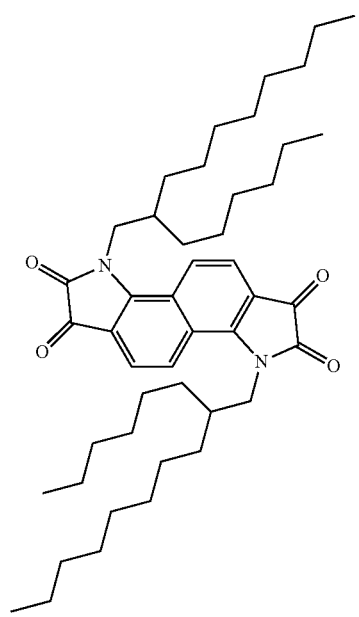

17

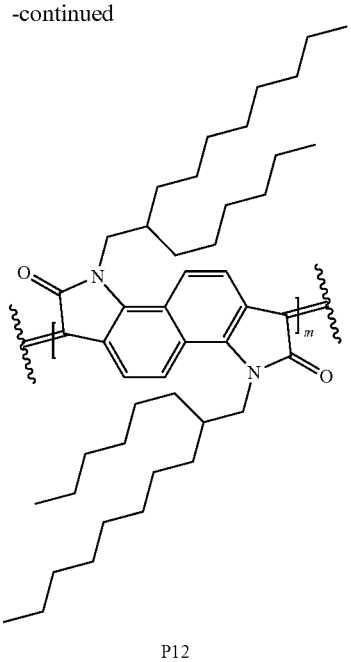

P12

To a microwave vial was added the respective bisisatin 17 (0.1 mmol, 1.0 e.q.) and then sealed. The sealed vial was degassed via vacuum and then purged with argon for three cycles. Anhydrous degassed toluene was added under argon and then tris(diethylamino)phosphine $P(NEt_2)_3$ (0.22 mmol, 2.2 e.q.) was added to the mixture at room temperature under bubbling of argon. The mixture turned dark green and then the temperature increased to 100° C. After reaction for 3 hours, the reaction mixture turned dark purple and was then poured into methanol. The resulting polymeric precipitate was filtered via thimble and then purified by Soxhlet extraction in a sequence of methanol, hexane, ethyl acetate, and finally chloroform. The chloroform fraction was concentrated by rotary evaporation, suspended in methanol and filtered to afford the polymer as a metallic dark green solid. GPC (Chlorobenzene at 80° C.): $M_n$=20.2 kDa, $M_w$=72.5 kDa, PDI=3.59.

Example 19 Synthesis of Thieno[3,2-b]thiophene Bisisatin 23

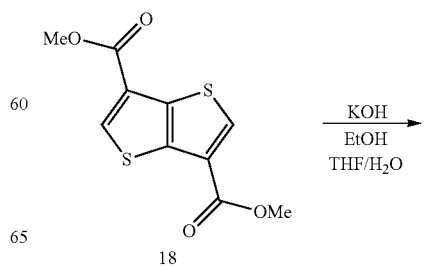

18

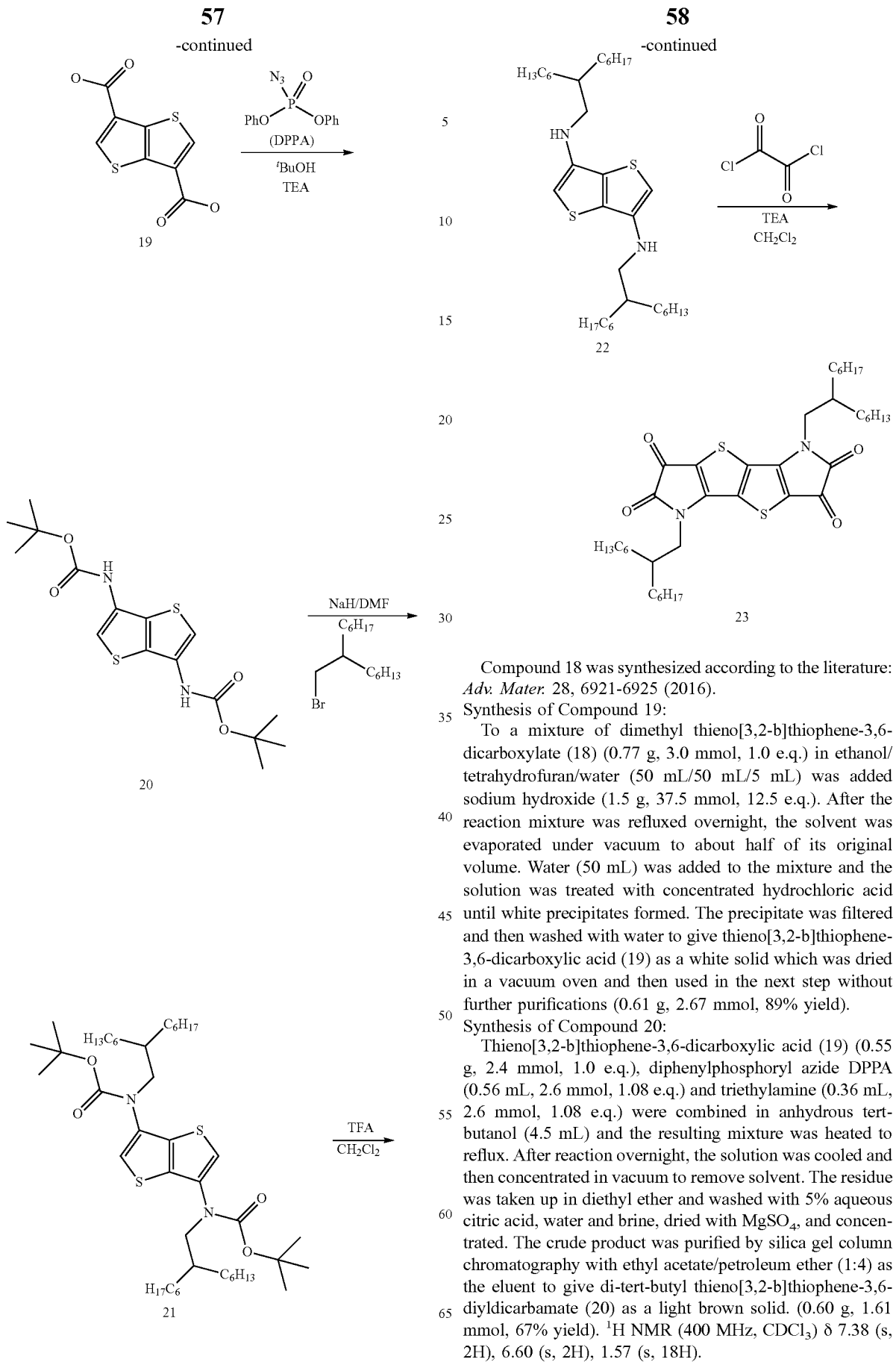

Compound 18 was synthesized according to the literature: *Adv. Mater.* 28, 6921-6925 (2016).

Synthesis of Compound 19:

To a mixture of dimethyl thieno[3,2-b]thiophene-3,6-dicarboxylate (18) (0.77 g, 3.0 mmol, 1.0 e.q.) in ethanol/tetrahydrofuran/water (50 mL/50 mL/5 mL) was added sodium hydroxide (1.5 g, 37.5 mmol, 12.5 e.q.). After the reaction mixture was refluxed overnight, the solvent was evaporated under vacuum to about half of its original volume. Water (50 mL) was added to the mixture and the solution was treated with concentrated hydrochloric acid until white precipitates formed. The precipitate was filtered and then washed with water to give thieno[3,2-b]thiophene-3,6-dicarboxylic acid (19) as a white solid which was dried in a vacuum oven and then used in the next step without further purifications (0.61 g, 2.67 mmol, 89% yield).

Synthesis of Compound 20:

Thieno[3,2-b]thiophene-3,6-dicarboxylic acid (19) (0.55 g, 2.4 mmol, 1.0 e.q.), diphenylphosphoryl azide DPPA (0.56 mL, 2.6 mmol, 1.08 e.q.) and triethylamine (0.36 mL, 2.6 mmol, 1.08 e.q.) were combined in anhydrous tert-butanol (4.5 mL) and the resulting mixture was heated to reflux. After reaction overnight, the solution was cooled and then concentrated in vacuum to remove solvent. The residue was taken up in diethyl ether and washed with 5% aqueous citric acid, water and brine, dried with $MgSO_4$, and concentrated. The crude product was purified by silica gel column chromatography with ethyl acetate/petroleum ether (1:4) as the eluent to give di-tert-butyl thieno[3,2-b]thiophene-3,6-diyldicarbamate (20) as a light brown solid. (0.60 g, 1.61 mmol, 67% yield). $^1$H NMR (400 MHz, $CDCl_3$) δ 7.38 (s, 2H), 6.60 (s, 2H), 1.57 (s, 18H).

Synthesis of Compound 21:

Di-tert-butyl thieno[3,2-b]thiophene-3,6-diyldicarbamate (20) (0.93 g, 2.5 mmol, 1.0 e.q.) was dissolved in DMF (25 mL) and cooled to 0° C. Sodium hydride (0.40 g, 60% dispersion in mineral oil, 10.0 mmol, 4.0 e.q.) was added and the solution was stirred at room temperature for 1 hour. 7-(bromomethyl)pentadecane (2.29 g, 7.5 mmol, 3.0 e.q.) was added to the mixture and the solution was stirred at 80° C. for 3 hours. After the solution cooled to room temperature, the mixture was poured into iced water, followed by extraction with ethyl acetate for three times. The organic layers were combined, washed with water, brine and then dried over $MgSO_4$, concentrated. The resulting brown oil was purified via silica gel column chromatography with dichloromethane/petroleum ether (1:1) as the eluent to give di-tert-butyl thieno[3,2-b]thiophene-3,6-diylbis((2-hexyldecyl)carbamate) as a light brown oil (21) (1.64 g, 2.0 mmol, 80% yield). $^1$H NMR (400 MHz, $CDCl_3$) δ 7.04 (s, 2H), 3.62 (d, J=7.2 Hz, 4H), 1.58-1.48 (m, 2H), 1.34-1.11 (m, 48H), 0.87 (q, J=6.8 Hz, 12H). $^{13}$C NMR (101 MHz, $CDCl_3$) δ 154.13, 134.76, 133.70, 119.18, 80.64, 53.38, 36.93, 31.90, 31.77, 31.21, 30.03, 29.68, 29.52, 29.29, 28.15, 26.31, 26.25, 22.66, 22.62, 14.08.

Synthesis of Compound 22:

Di-tert-butylthieno[3,2-b]thiophene-3,6-diylbis((2-hexyldecyl)carbamate) (21) (1.64 g, 2.0 mmol, 1.0 e.q.) was dissolved in dichloromethane (20 mL) and cooled to 0° C. Trifluoroacetic acid (2.7 mL) was added and the reaction mixture was allowed to warm to room temperature and stirred for overnight. The mixture was poured into water, washed with sodium bicarbonate, brine, dried over $MgSO_4$ and then concentrated to afford $N^3,N^6$-bis(2-hexyldecyl)thieno[3,2-b]thiophene-3,6-diamine (22) a light brown oil. The product is unstable in air and used immediately without further purifications in the next step (1.1 g, 1.78 mmol, 89% yield). $^1$H NMR (400 MHz, $CDCl_3$) δ 5.97 (s, 2H), 3.53 (s, 2H), 3.10 (d, J=6.1 Hz, 4H), 1.72-1.63 (m, 2H), 1.50-1.16 (m, 48H), 0.91 (t, J=6.6 Hz, 12H).

Synthesis of Compound 23:

$N^3,N^6$-bis(2-hexyldecyl)thieno[3,2-b]thiophene-3,6-diamine (22) (1.1 g, 1.78 mmol, 1.0 e.q.) in anhydrous dichloromethane (5 mL) was added dropwise to a stirring solution of oxalyl chloride (0.39 mL, 4.63 mmol, 2.6 e.q.) in anhydrous dichloromethane (10 mL) at 0° C. The mixture was allowed to warm to room temperature and stirred for one hour. Triethylamine (2.23 mL, 16.02 mmol, 9.0 e.q.) in anhydrous dichloromethane (5 mL) was added dropwise at room temperature and the solution was stirred for overnight. The mixture was poured into water and then extracted with dichloromethane for three times. The organic layers were combined, washed with water, brine and then dried over $MgSO_4$, concentrated. The crude product was purified via silica gel column chromatography with dichloromethane/petroleum ether (3:2) as the eluent and then recrystallized with dichloromethane/methanol to the product (23) as a purple solid. $^1$H NMR (400 MHz, $CDCl_3$) δ 3.70 (d, J=7.7 Hz, 4H), 1.87 (q, J=6.4 Hz, 2H), 1.47-1.20 (m, 48H), 0.93-0.86 (m, 12H). 13C NMR (101 MHz, $CDCl_3$) δ 173.02, 160.00, 157.06, 134.45, 116.98, 47.23, 38.99, 31.86, 31.73, 31.28, 29.97, 29.64, 29.49, 29.28, 26.24, 26.19, 22.67, 22.64, 14.13, 14.09.

Example 20 Polymerization to Give pDPID P14

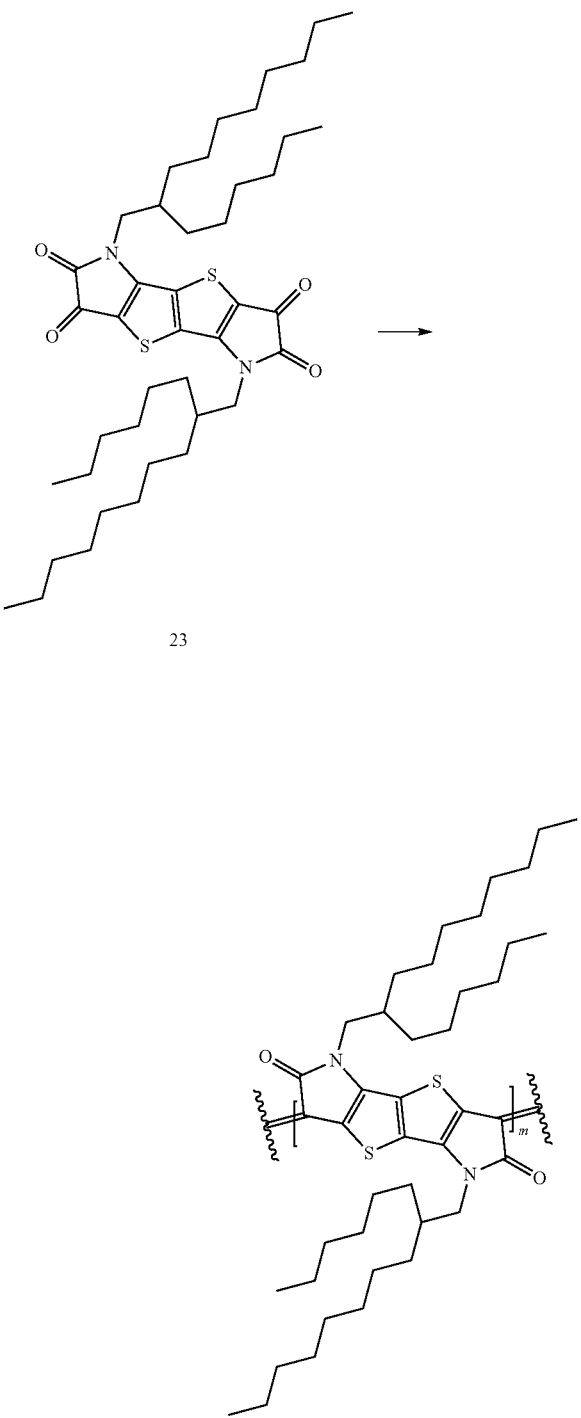

Polymer P14 was synthesized from compound 23 according to the procedure for polymer P12 in example 18.

The invention claimed is:

1. A polymer, consisting of unit having a structure of formula (II')

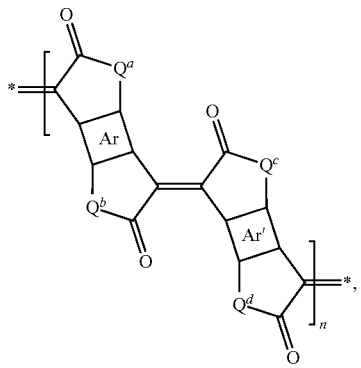

(II')

wherein $Q^a$, $Q^b$, $Q^c$ and $Q^d$ are independently O, S or an $NR^1$ group, Ar and Ar' are independently selected from the group consisting of

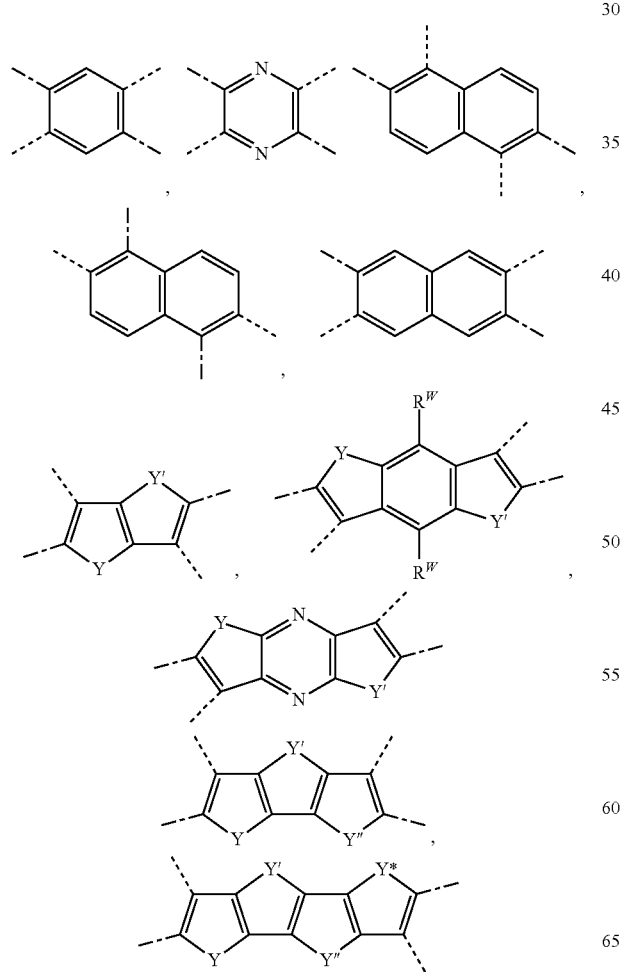

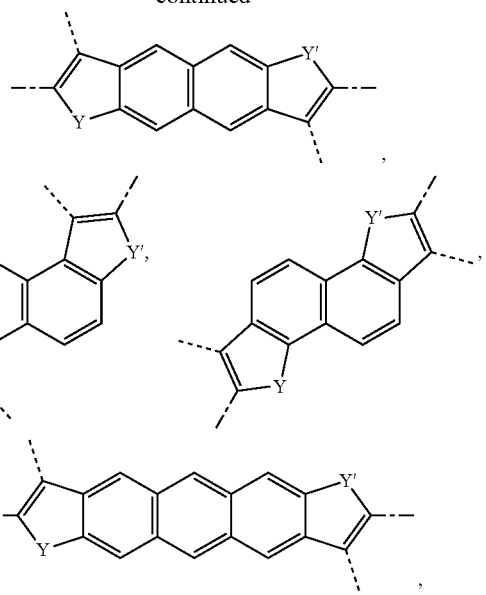

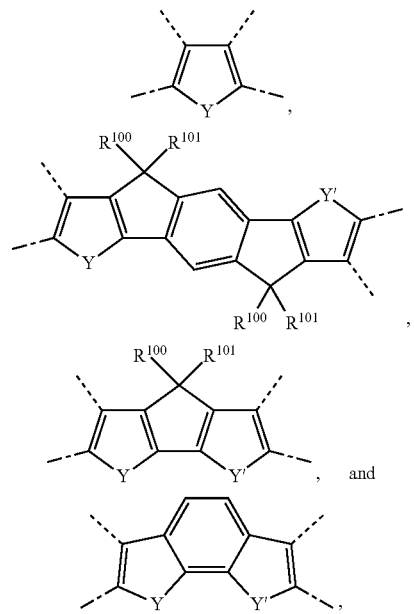

each Y, Y', Y" and Y* is independently O, S, an $NR^{1a}$ group, Se, or Te, and each $R^W$ is independently H, a $C_{1-30}$-alkyl group, a $C_{1-30}$-alkoxy group, or a moiety

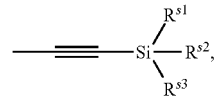

$R^{s1}$, $R^{s2}$ and $R^{s3}$ are independently H, a $C_{1-20}$-alkyl group, a $C_{2-20}$-alkenyl group, or a phenyl group, Ar or Ar' is bound via the single bonds ----- and --- to the moieties

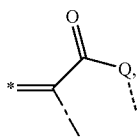

Q is $Q^a$, $Q^b$, $Q^c$ or $Q^d$,

Ar and/or Ar' optionally comprise a substituent $R^2$, each $R^1$ and $R^{1a}$ is independently selected from the group consisting of H, a $C_{1-100}$-alkyl group, a $C_{2-100}$-alkenyl group, a $C_{2-100}$-alkynyl group, a $C_{5-12}$-cycloalkyl group, a $C_{6-18}$-aryl group, a 5 to 20 membered heteroaryl group, a C(O)—$C_{1-100}$-alkyl group, a C(O)—$C_{5-12}$-cycloalkyl group and a C(O)—$OC_{1-100}$-alkyl group, the $C_{1-100}$-alkyl group, the $C_{2-100}$-alkenyl group and the $C_{2-100}$-alkynyl group optionally comprise one to forty substituents independently selected from the group consisting of a $C_{5-8}$-cycloalkyl group, a $C_{6-14}$-aryl group, a 5 to 14 membered heteroaryl group, an $OR^a$ group, an OC(O)—$R^a$ group, a C(O)—$OR^a$ group, a C(O)—$R^a$ group, an $NR^aR^b$ group, an $NR^a$—C(O)$R^b$ group, a C(O)—$NR^aR^b$ group, an N[C(O)$R^a$][C(O)$R^b$] group, an $SR^a$ group, an Si($R^{Sia}$)($R^{Sib}$)($R^{Sic}$) group, an —O—Si($R^{Sia}$)($R^{Sib}$)($R^{Sic}$) group, a halogen, CN, and $NO_2$, at least two $CH_2$-groups, but not adjacent $CH_2$-groups, of the $C_{1-100}$-alkyl group, the $C_{2-100}$-alkenyl group and/or the $C_{2-100}$-alkynyl group can be replaced by O or S, the $C_{5-12}$-cycloalkyl group optionally comprises one to six substituents independently selected from the group consisting of a $C_{1-60}$-alkyl group, a $C_{2-60}$-alkenyl group, a $C_{2-60}$-alkynyl group, a $C_{5-8}$-cycloalkyl group, a $C_{6-14}$-aryl group, a 5 to 14 membered heteroaryl group, an $OR^a$ group, an OC(O)—$R^a$ group, a C(O)—$OR^a$ group, a C(O)—$R^a$ group, an $NR^aR^b$ group, an $NR^a$—C(O)$R^b$ group, a C(O)—$NR^aR^b$ group, an N[C(O)$R^a$][C(O)$R^b$] group, an $SR^a$ group, an Si($R^{Sia}$)($R^{Sib}$)($R^{Sic}$) group, an —O—Si($R^{Sia}$)($R^{Sib}$)($R^{Sic}$) group, a halogen, CN, and $NO_2$, one or two $CH_2$-groups, but not adjacent $CH_2$-groups, of the $C_{5-12}$-cycloalkyl group can be replaced by O, S, OC(O), CO, an $NR^a$ group or an $NR^a$—CO group, the $C_{6-18}$-aryl group and the 5 to 20 membered heteroaryl group optionally comprise one to six substituents independently selected from the group consisting of a $C_{1-60}$-alkyl group, a $C_{2-60}$-alkenyl group, a $C_{2-60}$-alkynyl group, a $C_{5-8}$-cycloalkyl group, a $C_{6-14}$-aryl group, a 5 to 14 membered heteroaryl group, an $OR^a$ group, an OC(O)—$R^a$ group, a C(O)—$OR^a$ group, a C(O)—$R^a$ group, an $NR^aR^b$ group, an $NR^a$—C(O)$R^b$ group, a C(O)—$NR^aR^b$ group, an N[C(O)$R^a$][C(O)$R^b$] group, an $SR^a$ group, an Si($R^{Sia}$)($R^{Sib}$)($R^{Sic}$) group, an —O—Si($R^{Sia}$)($R^{Sib}$)($R^{Sic}$) group, a halogen, CN, and $NO_2$, $R^a$ and $R^b$ are independently selected from the group consisting of H, a $C_{1-60}$-alkyl group, a $C_{2-60}$-alkenyl group, a $C_{2-60}$-alkynyl group, a $C_{5-8}$-cycloalkyl group, a $C_{6-14}$-aryl group and a 5 to 14 membered heteroaryl group, $R^{Sia}$, $R^{Sib}$ and $R^{Sic}$ are independently selected from the group consisting of H, a $C_{1-60}$-alkyl group, a $C_{2-60}$-alkenyl group, a $C_{2-60}$-alkynyl group, a $C_{5-8}$-cycloalkyl group, a $C_{6-14}$-aryl group, a 5 to 14 membered heteroaryl group, an O—$C_{1-60}$-alkyl group, an O—$C_{2-60}$-alkenyl group, an O—$C_{2-60}$-alkynyl group, an O—$C_{5-8}$-cycloalkyl group, an O—$C_{6-14}$-aryl group, an O-5 to 14 membered heteroaryl group, an —[O—Si$R^{Sid}R^{Sie}$]$_o$—$R^{Sif}$ group, an $NR^5R^6$ group, a halogen and an O—C(O)—$R^5$ group, o is an integer from 1 to 50, $R^{Sid}$, $R^{Sie}$, $R^{Sif}$ are independently selected from the group consisting of H, a $C_{1-60}$-alkyl group, a $C_{2-60}$-alkenyl group, a $C_{2-60}$-alkynyl group, a $C_{5-8}$-cycloalkyl group, a $C_{6-14}$-aryl group, a 5 to 14 membered heteroaryl group, an O—$C_{1-60}$-alkyl group, an O—$C_{2-60}$-alkenyl group, an O—$C_{2-60}$-alkynyl group, an O—$C_{5-8}$-cycloalkyl group, an O—$C_{6-14}$-aryl group, an O-5 to 14 membered heteroaryl group, an —[O—Si$R^{Sig}R^{Sih}$]$_p$—$R^{Sii}$ group, an $NR^{50}R^{60}$ group, a halogen and an O—C(O)—$R^{50}$ group, p is an integer from 1 to 50, $R^{Sig}$ $R^{Sih}$, $R^{Sii}$ are independently selected from the group consisting of H, a $C_{1-30}$-alkyl group, a $C_{2-30}$-alkenyl group, a $C_{2-30}$-alkynyl group, a $C_{5-6}$-cycloalkyl group, a $C_{6-10}$-aryl group, a 5 to 10 membered heteroaryl group, an O—$C_{1-30}$-alkyl group, an O—$C_{2-30}$-alkenyl group, an O—$C_{2-30}$-alkynyl group, an O—$C_{5-6}$-cycloalkyl group, an O—$C_{6-10}$-aryl group, an O-5 to 10 membered heteroaryl group, an O—Si($CH_3$)$_3$ group, an $NR^{500}R^{600}$ group, a halogen and an O—C(O)—$R^{500}$ group, $R^5$, $R^6$, $R^{50}$, $R^{60}$, $R^{500}$ and $R^{600}$ are independently selected from the group consisting of H, a $C_{1-60}$-alkyl group, a $C_{2-60}$-alkenyl group, a $C_{2-60}$-alkynyl group, a $C_{5-8}$-cycloalkyl group, a $C_{6-14}$-aryl group, and a 5 to 14 membered heteroaryl group, the $C_{1-60}$-alkyl group, the $C_{2-60}$-alkenyl group and the $C_{2-60}$-alkynyl group optionally comprise one to twenty substituents selected from the group consisting of a $C_{5-6}$-cycloalkyl group, a $C_{6-10}$-aryl group, an $OR^c$ group, an OC(O)—$R^c$ group, a C(O)—$OR^c$ group, a C(O)—$R^c$ group, an $NR^cR^d$ group, an $NR^c$—C(O)$R^d$ group, a C(O)—$NR^cR^d$ group, an N[C(O)$R^c$][C(O)$R^d$] group, an $SR^c$ group, an Si($R^{Sij}$)($R^{Sik}$)($R^{Sil}$) group, an —O—Si($R^{Sij}$)($R^{Sik}$)($R^{Sil}$) group, a halogen, CN, and $NO_2$, at least two $CH_2$-groups, but not adjacent $CH_2$-groups, of the $C_{1-60}$-alkyl group, the $C_{2-60}$-alkenyl group and/or the $C_{2-60}$-alkynyl group can be replaced by O or S, the $C_{5-8}$-cycloalkyl group optionally comprises one to five substituents selected from the group consisting of a $C_{1-30}$-alkyl group, a $C_{2-30}$-alkenyl group, a $C_{2-30}$-alkynyl group, a $C_{5-6}$-cycloalkyl group, a $C_{6-10}$-aryl group, an OR group, an OC(O)—$R^c$ group, a C(O)—$OR^c$ group, a C(O)—$R^c$ group, an $NR^cR^d$ group, an $NR^c$—C(O)$R^d$ group, a C(O)—$NR^cR^d$ group, an N[C(O)$R^c$][C(O)$R^d$] group, an $SR^c$ group, an Si($R^{Sij}$)($R^{Sik}$)($R^{Sil}$) group, an —O—Si($R^{Sij}$)($R^{Sik}$)($R^{Sil}$) group, a halogen, CN, and $NO_2$, one or two $CH_2$-groups, but not adjacent $CH_2$-groups, of the $C_{5-8}$-cycloalkyl group can be replaced by O, S, OC(O), CO, an NR group or an $NR^c$—CO group, the $C_{6-14}$-aryl group and the 5 to 14 membered heteroaryl group optionally comprise one to five substituents independently selected from the group consisting of a $C_{1-30}$-alkyl group, a $C_{2-30}$-alkenyl group, a $C_{2-30}$-alkynyl group, a $C_{5-6}$-cycloalkyl group, a $C_{6-10}$-aryl group, an OR group, an OC(O)—$R^c$ group, a C(O)—$OR^c$ group, a C(O)—$R^c$ group, an $NR^cR^d$ group, an $NR^c$—C(O)$R^d$ group, a C(O)—$NR^cR^d$ group, an N[C(O)$R^c$]

[C(O)R$^d$] group, an SR$^e$ group, an Si(R$^{Sij}$)(R$^{Sik}$)(R$^{Sil}$) group, an —O—Si(R$^{Sij}$)(R$^{Sik}$)(R$^{Sil}$) group, a halogen, CN and NO$_2$, R$^c$ and R$^d$ are independently selected from the group consisting of H, a C$_{1-30}$-alkyl group, a C$_{2-30}$-alkenyl group and a C$_{2-30}$-alkynyl group, R$^{Sij}$, R$^{Sik}$ and R$^{Sil}$ are independently selected from the group consisting of H, a C$_{1-30}$-alkyl group, a C$_{2-30}$-alkenyl group, a C$_{2-30}$-alkynyl group, a C$_{5-6}$-cycloalkyl group, a C$_{6-10}$-aryl group, a 5 to 10 membered heteroaryl group, an O—C$_{1-30}$-alkyl group, an O—C$_{2-30}$-alkenyl group, an OC$_{2-30}$-alkynyl group, an O—C$_{5-6}$-cycloalkyl group, an O—C$_{6-10}$-aryl group, an O-5 to 10 membered heteroaryl group, an —[O—SiR$^{Sim}$R$^{Sin}$]$_q$—R$^{Sio}$ group, an NR$^7$R$^8$ group, a halogen, and an O—C(O)—R$^7$ group, q is an integer from 1 to 50, R$^{Sim}$, R$^{Sin}$, R$^{Sio}$ are independently selected from the group consisting of H, a C$_{1-30}$-alkyl group, a C$_{2-30}$-alkenyl group, a C$_{2-30}$-alkynyl group, a C$_{5-6}$-cycloalkyl group, a C$_{6-10}$-aryl group, a 5 to 10 membered heteroaryl group, an O—C$_{1-30}$-alkyl group, an O—C$_{2-30}$-alkenyl group, an O—C$_{2-30}$-alkynyl group, an O—C$_{5-6}$-cycloalkyl group, an OC$_{6-10}$-aryl group, an O-5 to 10 membered heteroaryl group, an —[O—SiR$^{Sip}$R$^{Siq}$]$_r$—R$^{Sir}$ group, an NR$^{70}$R$^{80}$ group, a halogen, and an O—C(O)—R$^{70}$ group, r is an integer from 1 to 50, R$^{Sip}$, R$^{Siq}$, R$^{Sir}$ are independently selected from the group consisting of H, a C$_{1-30}$-alkyl group, a C$_{2-30}$-alkenyl group, a C$_{2-30}$-alkynyl group, a C$_{5-6}$-cycloalkyl group, a C$_{6-10}$-aryl group, a 5 to 10 membered heteroaryl group, an O—C$_{1-30}$-alkyl group, an OC$_{2-30}$-alkenyl group, an O—C$_{2-30}$-alkynyl group, an O—C$_{5-6}$-cycloalkyl group, an O—C$_{6-10}$-aryl group, an O-5 to 10 membered heteroaryl group, an O—Si(CH$_3$)$_3$ group, an NR$^{700}$R$^{800}$ group, a halogen and an O—C(O)—R$^{700}$ group, R$^7$, R$^8$, R$^{70}$, R$^{80}$, R$^{700}$ and R$^{800}$ are independently selected from the group consisting of H, a C$_{1-30}$-alkyl group, a C$_{2-30}$-alkenyl group, a C$_{2-30}$-alkynyl group, a C$_{5-6}$-cycloalkyl group, a C$_{6-10}$-aryl group, and a 5 to 10 membered heteroaryl group, the C$_{1-30}$-alkyl group, the C$_{2-30}$-alkenyl group and the C$_{2-30}$-alkynyl group optionally comprise one to ten substituents selected from the group consisting of a halogen, CN and NO$_2$, each R$^2$ is selected from the group consisting of a C$_{1-30}$-alkyl group, a C$_{2-30}$-alkenyl group, a C$_{2-30}$-alkynyl group, a C$_{5-12}$-cycloalkyl group, a C$_{6-18}$-aryl group, a 5 to 20 membered heteroaryl group, an OR$^{21}$ group, an OC(O)—R$^{21}$ group, a C(O)—OR$^{21}$ group, a C(O)—R$^{21}$ group, an NR$^{21}$R$^{22}$ group, an NR$^{21}$—C(O)R$^{22}$ group, a C(O)—NR$^{21}$R$^{22}$ group, an N[C(O)R$^{21}$][C(O)R$^{22}$] group, an SR$^{21}$ group, a halogen, CN, an SiR$^{Sis}$R$^{Sit}$R$^{Siu}$ group and OH, R$^{21}$ and R$^{22}$ and are independently selected from the group consisting of H, a C$_{1-30}$-alkyl group, a C$_{2-30}$-alkenyl group, a C$_{2-30}$-alkynyl group, a C$_{5-12}$-cycloalkyl group, a C$_{6-18}$-aryl group and a 5 to 20 membered heteroaryl group, the C$_{1-30}$-alkyl group, the C$_{2-30}$-alkenyl group and the C$_{2-30}$-alkynyl group optionally comprise one to ten substituents independently selected from the group consisting of a C$_{5-8}$-cycloalkyl group, a C$_{6-14}$-aryl group, a 5 to 14 membered heteroaryl group, an OR$^e$ group, an OC(O)—R$^e$ group, a C(O)—OR$^e$ group, a C(O)—R$^e$ group, an NR$^e$R$^f$ group, an NR$^e$—C(O)R$^f$ group, a C(O)—NR$^e$R$^f$ group, an N[C(O)R$^e$][C(O)R$^f$] group, an SR$^e$ group, a halogen, CN, an SiR$^{Sis}$R$^{Sit}$R$^{Siu}$ group and NO$_2$, at least two CH$_2$-groups, but not adjacent CH$_2$-groups, of the C$_{1-30}$-alkyl group, the C$_{2-30}$-alkenyl group and/or the C$_{2-30}$-alkynyl group can be replaced by O or S, the C$_{5-12}$-cycloalkyl optionally comprises one to six substituents independently selected from the group consisting of a C$_{1-20}$-alkyl group, a C$_{2-20}$-alkenyl group, a C$_{2-20}$-alkynyl group, a C$_{5-8}$-cycloalkyl group, a C$_{6-14}$-aryl group, a 5 to 14 membered heteroaryl group, an OR$^e$ group, an OC(O)—R$^e$ group, a C(O)—OR$^e$ group, a C(O)—R$^e$ group, an NR$^e$R$^f$ group, an NR$^e$—C(O)R$^f$ group, a C(O)—NR$^e$R$^f$ group, an N[C(O)R$^e$][C(O)R$^f$] group, an SR$^e$ group, a halogen, CN, an SiR$^{Sis}$R$^{Sit}$R$^{Siu}$ group and NO$_2$, one or two CH$_2$-groups, but not adjacent CH$_2$-groups, of the C$_{5-12}$-cycloalkyl group can be replaced by O, S, OC(O), CO, an NR$^e$ group or an NR$^e$—CO group, and the C$_{6-18}$-aryl group and the 5 to 20 membered heteroaryl group optionally comprise one to six substituents independently selected from the group consisting of a C$_{1-20}$-alkyl group, a C$_{2-20}$-alkenyl group, a C$_{2-20}$-alkynyl group, a C$_{5-8}$-cycloalkyl group, a C$_{6-14}$-aryl group, a 5 to 14 membered heteroaryl group, an OR$^e$ group, an OC(O)—R$^e$ group, a C(O)—OR$^e$ group, a C(O)—R$^e$ group, an NR$^e$R$^f$ group, an NR$^e$—C(O)R$^f$ group, a C(O)—NR$^e$R$^f$ group, an N[C(O)R$^e$][C(O)R$^f$] group, an SR$^e$ group, a halogen, CN, an SiR$^{Sis}$R$^{Sit}$R$^{Siu}$ group and NO$_2$, R$^{Sis}$, R$^{Sit}$ and R$^{Siu}$ are independently selected from the group consisting of H, a C$_{1-20}$-alkyl group, a C$_{2-20}$-alkenyl group, a C$_{2-20}$-alkynyl group, a C$_{5-6}$-cycloalkyl group, a phenyl group and an O—Si(CH$_3$)$_3$ group, R$^e$ and R$^f$ are independently selected from the group consisting of H, a C$_{1-20}$-alkyl group, a C$_{2-20}$-alkenyl group, a C$_{2-20}$-alkynyl group, a C$_{5-8}$-cycloalkyl group, a C$_{6-14}$-aryl group, and a 5 to 14 membered heteroaryl group, the C$_{1-20}$-alkyl group, the C$_{2-20}$-alkenyl group and the C$_{2-20}$-alkynyl group optionally comprise one to five substituents selected from the group consisting of a C$_{5-6}$-cycloalkyl group, a C$_{6-10}$-aryl group, a 5 to 10 membered heteroaryl group, an OR$^g$ group, an OC(O)—R$^g$ group, a C(O)—OR$^g$ group, a C(O)—R$^g$ group, an NR$^g$R$^h$ group, an NR$^g$—C(O)R$^h$ group, a C(O)—NR$^g$R$^h$ group, an N[C(O)R$^g$][C(O)R$^h$] group, an SR$^g$ group, a halogen, CN, and NO$_2$, the C$_{5-8}$-cycloalkyl group optionally comprises one to five substituents selected from the group consisting of a C$_{1-10}$-alkyl group, a C$_{2-10}$-alkenyl group, a C$_{2-10}$-alkynyl group, a C$_{5-6}$-cycloalkyl group, a C$_{6-10}$-aryl group, a 5 to 10 membered heteroaryl group, an OR$^g$ group, an OC(O)—R$^g$ group, a C(O)—OR group, a C(O)—R group, an NR$^g$R$^h$ group, an NR$^g$—C(O)R$^h$ group, a C(O)—NR$^g$R$^h$ group, an N[C(O)R$^g$][C(O)R$^h$] group, an SR$^g$ group, a halogen, CN, and NO$_2$, the C$_{6-14}$-aryl group and the 5 to 14 membered heteroaryl group optionally comprise one to five substituents independently selected from the group consisting of a C$_{1-10}$-alkyl group, a C$_{2-10}$-alkenyl group, a C$_{2-10}$-alkynyl group, a C$_{5-6}$-cycloalkyl group, a C$_{6-10}$-aryl group, a 5 to 10 membered heteroaryl group, an OR$^g$ group, an OC(O)—R group, a C(O)—OR$^g$ group, a C(O)—R group, an NR$^g$R$^h$ group, an NR$^g$—C(O)R$^h$ group, a C(O)—NR<sup>g</sup>R<sup>h</sup> group, an N[C(O)R<sup>g</sup>][C(O)R<sup>h</sup>] group, an SR<sup>g</sup> group, a halogen, CN, and NO$_2$, R<sup>g</sup> and R<sup>h</sup> are independently selected from the group consisting of H, a C$_{1-10}$-alkyl group, a C$_{2-10}$-alkenyl group and a C$_{2-10}$-alkynyl group, the C$_{1-10}$-alkyl group, the C$_{2-10}$-alkenyl group and the C$_{2-10}$-alkynyl group optionally comprise one to five substituents selected from the group consisting of a halogen, CN and NO$_2$, each R$^{100}$ and R$^{101}$ is independently selected from the group consisting of H, a C$_{1-20}$-alkyl group, a C$_{2-20}$-alkenyl group, a C$_{2-20}$-alkynyl group, a C$_{5-8}$-cycloalkyl group, a C$_{6-14}$-aryl group, and a 5 to 14 membered heteroaryl group; or wherein R$^{100}$ and R$^{101}$, if attached to a same atom, together with the same atom, form a 5 to 12 membered ring system, the C$_{1-20}$-alkyl group, the C$_{2-20}$-alkenyl group and the C$_{2-20}$-alkynyl group optionally comprise one to five substituents selected from the group consisting of a C$_{5-6}$-cycloalkyl group, a C$_{6-10}$-aryl group, a 5 to 10 membered heteroaryl group, an OR$^q$ group, an OC(O)—R$^q$ group, a C(O)—OR$^q$ group, a C(O)—R$^q$ group, an NR$^q$R$^r$ group, an NR$^q$C(O)R$^r$ group, a C(O)—NR$^q$R$^r$ group, an N[C(O)R$^q$][C(O)R$^r$] group, an SR$^q$ group, a halogen, CN, and NO$_2$, the C$_{5-8}$-cycloalkyl group optionally comprises one to five substituents selected from the group consisting of a C$_{1-10}$-alkyl group, a C$_{2-10}$-alkenyl group, a C$_{2-10}$-alkynyl group, a C$_{5-6}$-cycloalkyl group, a C$_{6-10}$-aryl group, a 5 to 10 membered heteroaryl group, an OR$^q$ group, an OC(O)—R$^q$ group, a C(O)—OR$^q$ group, a C(O)—R$^q$ group, an NR$^q$R$^r$ group, an NR$^q$—C(O)R$^r$ group, a C(O)—NR$^q$R$^r$ group, an N[C(O)R$^q$][C(O)R$^r$] group, an SR$^q$ group, a halogen, CN, and NO$_2$, the C$_{6-14}$-aryl group and the 5 to 14 membered heteroaryl group optionally comprise one to five substituents independently selected from the group consisting of a C$_{1-10}$-alkyl group, a C$_{2-10}$-alkenyl group, a C$_{2-10}$-alkynyl group, a C$_{5-6}$-cycloalkyl group, a C$_{6-10}$-aryl group, a 5 to 10 membered heteroaryl group, an OR$^q$ group, an OC(O)—R$^g$ group, a C(O)—OR$^g$ group, a C(O)—R$^g$ group, an NR$^q$R$^r$ group, an NR$^q$—C(O)R$^r$ group, a C(O)—NR$^q$R$^r$ group, an N[C(O)R$^q$][C(O)R$^r$] group, a SR$^q$ group, a halogen, CN, and NO$_2$, the 5 to 12 membered ring system optionally comprises one to five substituents selected from the group consisting of a C$_{1-10}$-alkyl group, a C$_{2-10}$-alkenyl group, a C$_{2-10}$-alkynyl group, a C$_{5-6}$-cycloalkyl group, a C$_{6-10}$-aryl group, a 5 to 10 membered heteroaryl group, an OR$^q$ group, an OC(O)—R$^g$ group, a C(O)—OR$^g$ group, a C(O)—R$^g$ group, an NR$^q$R$^r$ group, an NR$^q$—C(O)R$^r$ group, a C(O)—NR$^q$R$^r$ group, an N[C(O)R$^q$][C(O)R$^r$] group, an SR$^q$ group, a halogen, CN, and NO$_2$, R$^q$ and R$^r$ are independently selected from the group consisting of H, a C$_{1-10}$alkyl group, a C$_{2-10}$-alkenyl group and a C$_{2-10}$-alkynyl group, the C$_{1-10}$-alkyl group, the C$_{2-10}$-alkenyl group and the C$_{2-10}$-alkynyl group optionally comprise one to five substituents selected from the group consisting of a halogen, CN and NO$_2$, and n is in a range from 3 to 1000.

2. The polymer of claim 1, wherein Ar and Ar' are independently selected from the group consisting of

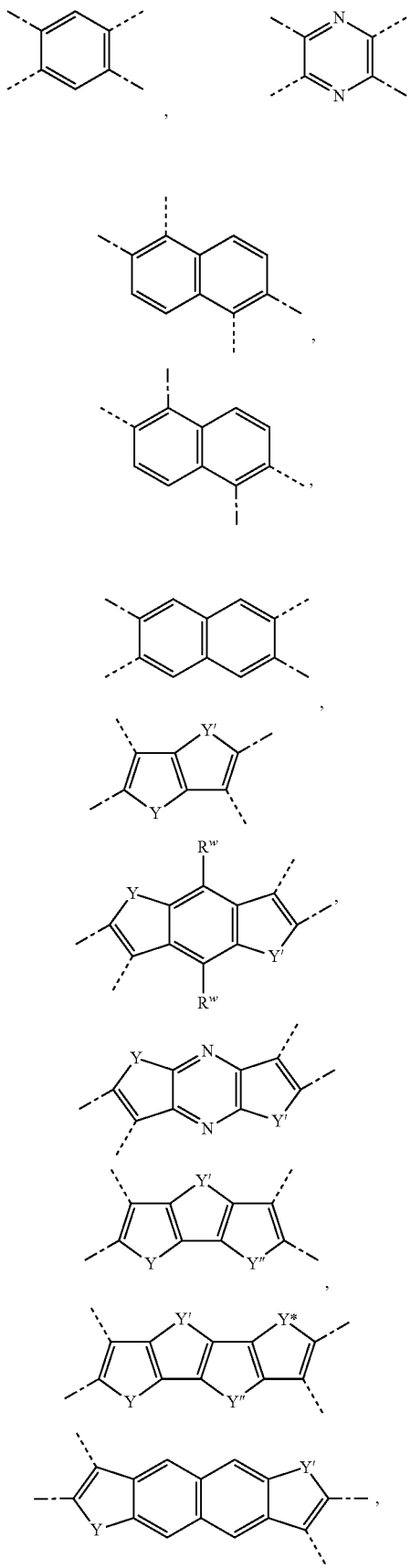

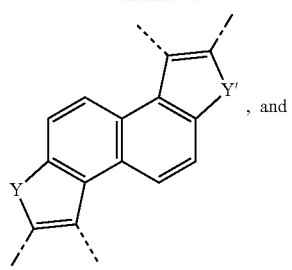, and

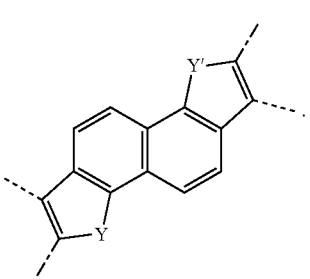

3. The polymer of claim 1, wherein Ar and Ar' are independently selected from the group consisting of

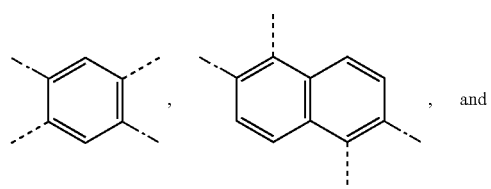, and

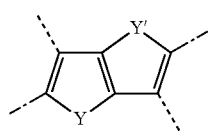.

4. The polymer of claim 1, consisting of units having a structure of formula 1', 2' or 3'

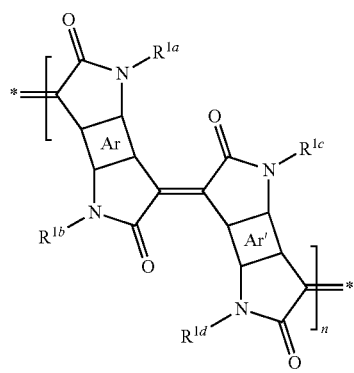

1'

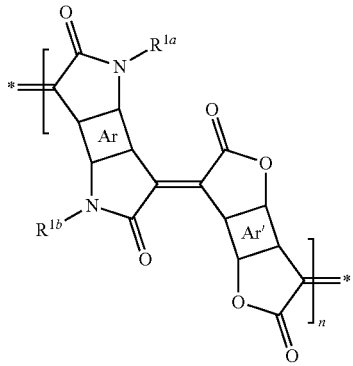

2'

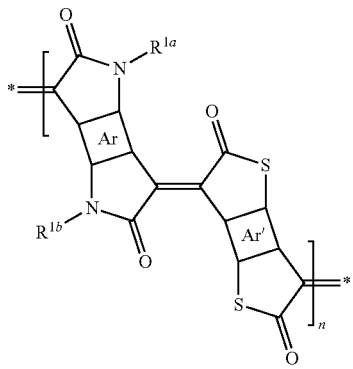

3' wherein $R^{1b}$, $R^{1c}$ and $R^{1d}$ are independently defined as $R^{1a}$.

5. A polymer consisting of units having a a structure of formula II''

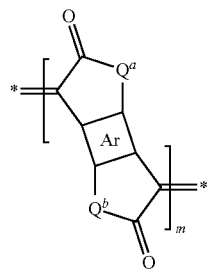

II''

$Q^a$ and $Q^b$ are independently O, S or an $NR^1$ group,

Ar is selected from the group consisting of:

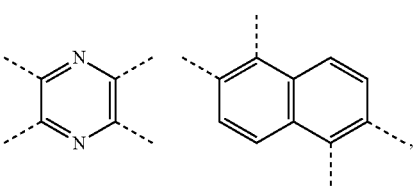

-continued

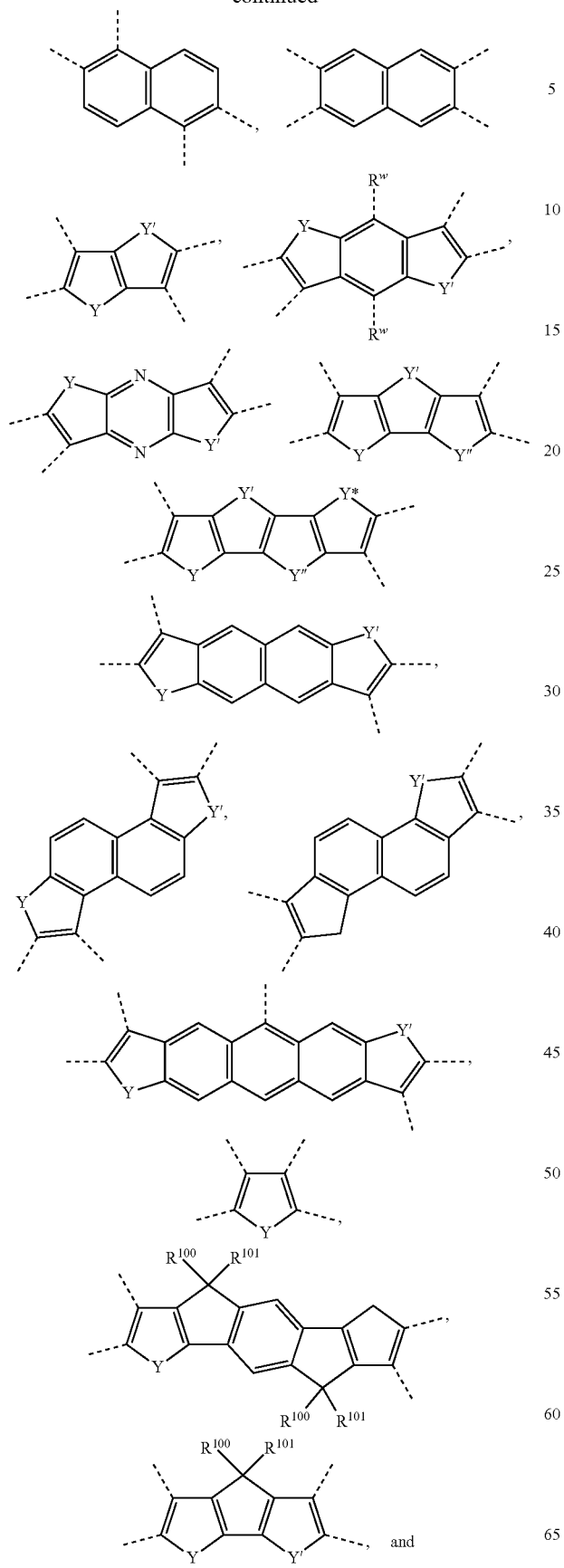

each Y, Y', Y" and Y* is independently O, S, and NR$^{1a}$ group, Se, or Te, and
each R$^W$ is independently H, a C$_{1-20}$-alkyl group, a C$_{1-30}$-alkoxy group, or a moiety:

R$^{a1}$, R$^{a2}$ and R$^{a3}$ are independently H, a C$_{1-20}$-alkyl group, a C$_{2-20}$-alkenyl group or a phenyl group,
Ar or Ar' is bound via the single bonds ----- and —··— to the moieties:

Q is Q$^a$, Q$^b$, Q$^c$, or Q$^d$,
Ar and/or Ar' optionally comprise a substituent R$^2$,
each R$^1$ and R$^{1a}$ is independently selected from the group consisting of H, a C$_{1-100}$-alkyl group, a C$_{2-100}$-alkenyl group, a C$_{2-100}$-alkynyl group, a C$_{5-12}$-cycloalkyl group, a C$_{6-18}$-aryl group, a 5 to 20 membered heteroaryl group, a C(O)—C$_{1-100}$-alkyl group, a C(O)—C$_{5-12}$-cycloalkyl group and a C(O)—OC$_{1-100}$-alkyl group,
the C$_{1-100}$-alkyl group, the C$_{2-100}$-alkenyl group and the C$_{2-100}$-alkynyl group optionally comprise one to forty substituents independently selected from the group consisting of a C$_{5-8}$-cycloalkyl group, a C$_{6-14}$-aryl group, a 5 to 14 membered heteroaryl group, an OR$^a$ group, an OC(O)—R$^a$ group, a C(O)—OR$^a$ group, a C(O)—R$^a$ group, an NR$^a$R$^b$ group, an NR$^a$—C(O)R$^b$ group, a C(O)—NR$^a$R$^b$ group, an N[C(O)R$^a$][C(O)R$^b$] group, an SR$^a$ group, an Si(R$^{Sia}$)(R$^{Sib}$)(R$^{Sic}$) group, an —O—Si(R$^{Sia}$)(R$^{Sib}$)(R$^{Sic}$) group, a halogen, CN, and NO$_2$,
at least two CH$_2$-groups, but not adjacent CH$_2$-groups, of the C$_{1-100}$-alkyl group, the C$_{2-100}$-alkenyl group and/or the C$_{2-100}$-alkynyl group can be replaced by O or S,
the C$_{5-12}$-cycloalkyl group optionally comprises one to six substituents independently selected from the group consisting of a C$_{1-60}$-alkyl group, a C$_{2-60}$-alkenyl group, a C$_{2-60}$-alkynyl group, a C$_{5-8}$-cycloalkyl group, a C$_{6-14}$-aryl group, a 5 to 14 membered heteroaryl group, an OR$^a$ group, an OC(O)—R$^a$ group, a C(O)—OR$^a$ group, a C(O)—R$^a$ group, an NR$^a$R$^b$ group, an NR$^a$—C(O)R$^b$ group, a C(O)—NR$^a$R$^b$ group, an N[C(O)R$^a$][C(O)R$^b$] group, an SR$^a$ group, an Si(R$^{Sia}$)(R$^{Sib}$)(R$^{Sic}$) group, an —O—Si(R$^{Sia}$)(R$^{Sib}$)(R$^{Sic}$) group, a halogen, CN, and NO$_2$,
one or two CH$_2$-groups, but not adjacent CH$_2$-groups, of the C$_{5-12}$-cycloalkyl group can be replaced by O, S, OC(O), CO, an NR$^a$ group or an NR$^a$—CO group, the $C_{6-18}$-aryl group and the 5 to 20 membered heteroaryl group optionally comprise one to six substituents independently selected from the group consisting of a $C_{1-60}$-alkyl group, a $C_{2-60}$-alkenyl group, a $C_{2-60}$-alkynyl group, a $C_{5-8}$-cycloalkyl group, a $C_{6-14}$-aryl group, a 5 to 14 membered heteroaryl group, an $OR^a$ group, an $OC(O)$—$R^a$ group, a $C(O)$—$OR^a$ group, a $C(O)$—$R^a$ group, an $NR^aR^b$ group, an $NR^a$—$C(O)R^b$ group, a $C(O)$—$NR^aR^b$ group, an $N[C(O)R^a][C(O)R^b]$ group, an $SR^a$ group, an $Si(R^{Sia})(R^{Sib})(R^{Sic})$ group, an —O—$Si(R^{Sia})(R^{Sib})(R^{Sic})$ group, a halogen, CN, and $NO_2$, $R^a$ and $R^b$ are independently selected from the group consisting of H, a $C_{1-60}$-alkyl group, a $C_{2-60}$-alkenyl group, a $C_{2-60}$-alkynyl group, a $C_{5-8}$-cycloalkyl group, a $C_{6-14}$-aryl group and a 5 to 14 membered heteroaryl group, $R^{Sia}$, $R^{Sib}$ and $R^{Sic}$ are independently selected from the group consisting of H, a $C_{1-60}$-alkyl group, a $C_{2-60}$-alkenyl group, a $C_{2-60}$-alkynyl group, a $C_{5-8}$-cycloalkyl group, a $C_{6-14}$-aryl group, a 5 to 14 membered heteroaryl group, an O—$C_{1-60}$-alkyl group, an O—$C_{2-60}$-alkenyl group, an O—$C_{2-60}$-alkynyl group, an O—$C_{5-8}$-cycloalkyl group, an O—$C_{6-14}$-aryl group, an O-5 to 14 membered heteroaryl group, an —$[O-SiR^{Sid}R^{Sie}]_o$—$R^{Sif}$ group, an $NR^5R^6$ group, a halogen and an O—C(O)—$R^5$ group, o is an integer from 1 to 50, $R^{Sid}$, $R^{Sie}$, $R^{Sif}$ are independently selected from the group consisting of H, a $C_{1-60}$-alkyl group, a $C_{2-60}$-alkenyl group, a $C_{2-60}$-alkynyl group, a $C_{5-8}$-cycloalkyl group, a $C_{6-14}$-aryl group, a 5 to 14 membered heteroaryl group, an O—$C_{1-60}$-alkyl group, an O—$C_{2-60}$-alkenyl group, an O—$C_{2-60}$-alkynyl group, an O—$C_{5-8}$-cycloalkyl group, an O—$C_{6-14}$-aryl group, an O-5 to 14 membered heteroaryl group, an —$[O-SiR^{Sig}R^{Sih}]_p$—$R^{Sii}$ group, an $NR^{50}R^{60}$ group, a halogen and an O—C(O)—$R^{50}$ group, p is an integer from 1 to 50, $R^{Sig}$, $R^{Sih}$, $R^{Sii}$ are independently selected from the group consisting of H, a $C_{1-30}$-alkyl group, a $C_{2-30}$-alkenyl group, a $C_{2-30}$-alkynyl group, a $C_{5-6}$-cycloalkyl group, a $C_{6-10}$-aryl group, a 5 to 10 membered heteroaryl group, an O—$C_{1-30}$-alkyl group, an O—$C_{2-30}$-alkenyl group, an O—$C_{2-30}$-alkynyl group, an O—$C_{5-6}$-cycloalkyl group, an O—$C_{6-10}$-aryl group, an O-5 to 10 membered heteroaryl group, an O—$Si(CH_3)_3$ group, an $NR^{500}R^{600}$ group, a halogen and an O—C(O)—$R^{500}$ group, $R^5$, $R^6$, $R^{50}$, $R^{60}$, $R^{500}$ and $R^{600}$ are independently selected from the group consisting of H, a $C_{1-60}$-alkyl group, a $C_{2-60}$-alkenyl group, a $C_{2-60}$-alkynyl group, a $C_{5-8}$-cycloalkyl group, a $C_{6-14}$-aryl group, and a 5 to 14 membered heteroaryl group, the $C_{1-60}$-alkyl group, the $C_{2-60}$-alkenyl group and the $C_{2-60}$-alkynyl group optionally comprise one to twenty substituents selected from the group consisting of a $C_{5-6}$-cycloalkyl group, a $C_{6-10}$-aryl group, an $OR^c$ group, an $OC(O)$—$R^c$ group, a $C(O)$—$OR^c$ group, a $C(O)$—$R^c$ group, an $NR^cR^d$ group, an $NR^c$—$C(O)R^d$ group, a $C(O)$—$NR^cR^d$ group, an $N[C(O)R^c][C(O)R^d]$ group, an $SR^c$ group, an $Si(R^{Sij})(R^{Sik})(R^{Sil})$ group, an —O—$Si(R^{Sij})(R^{Sik})(R^{Sil})$ group, a halogen, CN, and $NO_2$, at least two $CH_2$-groups, but not adjacent $CH_2$-groups, of the $C_{1-60}$-alkyl group, the $C_{2-60}$-alkenyl group and/or the $C_{2-60}$-alkynyl group can be replaced by O or S, the $C_{5-8}$-cycloalkyl group optionally comprises one to five substituents selected from the group consisting of a $C_{1-30}$-alkyl group, a $C_{2-30}$-alkenyl group, a $C_{2-30}$-alkynyl group, a $C_{5-6}$-cycloalkyl group, a $C_{6-10}$-aryl group, an OR group, an $OC(O)$—$R^c$ group, a $C(O)$—$OR^c$ group, an $C(O)$—$R^c$ group, an $NR^cR^d$ group, an $NR^c$—$C(O)R^d$ group, a $C(O)$—$NR^cR^d$ group, an $N[C(O)R^c][C(O)R^d]$ group, an $SR^c$ group, an $Si(R^{Sij})(R^{Sik})(R^{Sil})$ group, an —O—$Si(R^{Sij})(R^{Sik})(R^{Sil})$ group, a halogen, CN, and $NO_2$, one or two $CH_2$-groups, but not adjacent $CH_2$-groups, of the $C_{5-8}$-cycloalkyl group can be replaced by O, S, OC(O), CO, an NR group or an $NR^c$—CO group, the $C_{6-14}$-aryl group and the 5 to 14 membered heteroaryl group optionally comprise one to five substituents independently selected from the group consisting of a $C_{1-30}$-alkyl group, a $C_{2-30}$-alkenyl group, a $C_{2-30}$-alkynyl group, a $C_{5-6}$-cycloalkyl group, a $C_{6-10}$-aryl group, an OR group, an $OC(O)$—$R^c$ group, a $C(O)$—$OR^c$ group, a $C(O)$—$R^c$ group, an $NR^cR^d$ group, an $NR^c$—$C(O)R^d$ group, a $C(O)$—$NR^cR^d$ group, an $N[C(O)R^c][C(O)R^d]$ group, an $SR^c$ group, an $Si(R^{Sij})(R^{Sik})(R^{Sil})$ group, an —O—$Si(R^{Sij})(R^{Sik})(R^{Sil})$ group, a halogen, CN and $NO_2$, $R^c$ and $R^d$ are independently selected from the group consisting of H, a $C_{1-30}$-alkyl group, a $C_{2-30}$-alkenyl group and a $C_{2-30}$-alkynyl group, $R^{Sij}$, $R^{Sik}$ and $R^{Sil}$ are independently selected from the group consisting of H, a $C_{1-30}$-alkyl group, a $C_{2-30}$-alkenyl group, a $C_{2-30}$-alkynyl group, a $C_{5-6}$-cycloalkyl group, a $C_{6-10}$-aryl group, a 5 to 10 membered heteroaryl group, an O—$C_{1-30}$-alkyl group, an O—$C_{2-30}$-alkenyl group, an O—$C_{2-30}$-alkynyl group, an O—$C_{5-6}$-cycloalkyl group, an O—$C_{6-10}$-aryl group, an O-5 to 10 membered heteroaryl group, an —$[O-SiR^{Sim}R^{Sin}]_q$—$R^{Sio}$ group, an $NR^7R^8$ group, a halogen, and an O—C(O)—$R^7$ group, q is an integer from 1 to 50, $R^{Sim}$, $R^{Sin}$, $R^{Sio}$ are independently selected from the group consisting of H, a $C_{1-30}$-alkyl group, a $C_{2-30}$-alkenyl group, a $C_{2-30}$-alkynyl group, a $C_{5-6}$-cycloalkyl group, a $C_{6-10}$-aryl group, a 5 to 10 membered heteroaryl group, an O—$C_{1-30}$-alkyl group, an O—$C_{2-30}$-alkenyl group, an O—$C_{2-30}$-alkynyl group, an O—$C_{5-6}$-cycloalkyl group, an O—$C_{6-10}$-aryl group, an O-5 to 10 membered heteroaryl group, an —$[O-SiR^{Sip}R^{Siq}]_r$—$R^{Sir}$ group, an $NR^{70}R^{80}$ group, a halogen, and an O—C(O)—$R^{70}$ group, r is an integer from 1 to 50, $R^{Sip}$, $R^{Siq}$, $R^{Sir}$ are independently selected from the group consisting of H, a $C_{1-30}$-alkyl group, a $C_{2-30}$-alkenyl group, a $C_{2-30}$-alkynyl group, a $C_{5-6}$-cycloalkyl group, a $C_{6-10}$-aryl group, a 5 to 10 membered heteroaryl group, an O—$C_{1-30}$-alkyl group, an O—$C_{2-30}$-alkenyl group, an O—$C_{2-30}$-alkynyl group, an O—$C_{5-6}$-cycloalkyl group, an O—$C_{6-10}$-aryl group, an O-5 to 10 membered heteroaryl group, an O—$Si(CH_3)_3$ group, an $NR^{700}R^{800}$ group, a halogen and an O—C(O)—$R^{700}$ group, $R^7$, $R^8$, $R^{70}$, $R^{80}$, $R^{700}$ and $R^{800}$ are independently selected from the group consisting of H, a $C_{1-30}$-alkyl group, a $C_{2-30}$-alkenyl group, a $C_{2-30}$-alkynyl group, a $C_{5-6}$-cycloalkyl group, a $C_{6-10}$-aryl group, and a 5 to 10 membered heteroaryl group, the $C_{1-30}$-alkyl group, the $C_{2-30}$-alkenyl group and the $C_{2-30}$-alkynyl group optionally comprise one to ten substituents selected from the group consisting of a halogen, CN and $NO_2$, each $R^2$ is selected from the group consisting of a $C_{1-30}$-alkyl group, a $C_{2-30}$-alkenyl group, a $C_{2-30}$-alkynyl group, a $C_{5-12}$-cycloalkyl group, a $C_{6-18}$-aryl group, a 5 to 20 membered heteroaryl group, an $OR^{21}$ group, an $OC(O)$—$R^{21}$ group, a $C(O)$—$OR^{21}$ group, a $C(O)$—$R^{21}$ group, an $NR^{21}R^{22}$ group, an $NR^{21}$—$C(O)R^{22}$ group, a $C(O)$—$NR^{21}R^{22}$ group, an $N[C(O)R^{21}][C(O)R^{22}]$ group, an $SR^{21}$ group, a halogen, CN, an $SiR^{Sis}R^{Sit}R^{Siu}$ group and OH, $R^{21}$ and $R^{22}$ and are independently selected from the group consisting of H, a $C_{1-30}$-alkyl group, a $C_{2-30}$-alkenyl group, a $C_{2-30}$-alkynyl group, a $C_{5-12}$-cycloalkyl group, a $C_{6-18}$-aryl group and a 5 to 20 membered heteroaryl group, the $C_{1-30}$-alkyl group, the $C_{2-30}$-alkenyl group and the $C_{2-30}$-alkynyl group optionally comprise one to ten substituents independently selected from the group consisting of a $C_{5-8}$-cycloalkyl group, a $C_{6-14}$-aryl group, a 5 to 14 membered heteroaryl group, an $OR^e$ group, an $OC(O)$—$R^e$ group, a $C(O)$—$OR^e$ group, a $C(O)$—$R^e$ group, an $NR^eR^f$ group, an $NR^e$—$C(O)R^f$ group, a $C(O)$—$NR^eR^f$ group, an $N[C(O)R^e][C(O)R^f]$ group, an $SR^e$ group, a halogen, CN, an $SiR^{Sis}R^{Sit}R^{Siu}$ group and $NO_2$, at least two $CH_2$-groups, but not adjacent $CH_2$-groups, of the $C_{1-30}$-alkyl group, the $C_{2-30}$-alkenyl group and/or the $C_{2-30}$-alkynyl group can be replaced by O or S, the $C_{5-12}$-cycloalkyl optionally comprises one to six substituents independently selected from the group consisting of a $C_{1-20}$-alkyl group, a $C_{2-20}$-alkenyl group, a $C_{2-20}$-alkynyl group, a $C_{5-8}$-cycloalkyl group, a $C_{6-14}$-aryl group, a 5 to 14 membered heteroaryl group, an $OR^e$ group, an $OC(O)$—$R^e$ group, a $C(O)$—$OR^e$ group, a $C(O)$—$R^e$ group, an $NR^eR^f$ group, an $NR^e$—$C(O)R^f$ group, a $C(O)$—$NR^eR^f$ group, an $N[C(O)R^e][C(O)R^f]$ group, an $SR^e$ group, a halogen, CN, an $SiR^{Sis}R^{Sit}R^{Siu}$ group and $NO_2$, one or two $CH_2$-groups, but not adjacent $CH_2$-groups, of the $C_{5-12}$-cycloalkyl group can be replaced by O, S, OC(O), CO, an $NR^e$ group or an $NR^e$—CO group, the $C_{6-18}$-aryl group and the 5 to 20 membered heteroaryl group optionally comprise one to six substituents independently selected from the group consisting of a $C_{1-20}$-alkyl group, a $C_{2-20}$-alkenyl group, a $C_{2-20}$-alkynyl group, a $C_{5-8}$-cycloalkyl group, a $C_{6-14}$-aryl group, a 5 to 14 membered heteroaryl group, an $OR^e$ group, an $OC(O)$—$R^e$ group, a $C(O)$—$OR^e$ group, a $C(O)$—$R^e$ group, an $NR^eR^f$ group, an $NR^e$—$C(O)R^f$ group, a $C(O)$—$NR^eR^f$ group, an $N[C(O)R^e][C(O)R^f]$ group, an $SR^e$ group, a halogen, CN, an $SiR^{Sis}R^{Sit}R^{Siu}$ group and $NO_2$, $R^{Sis}$, $R^{Sit}$ and $R^{Siu}$ are independently selected from the group consisting of H, a $C_{1-20}$-alkyl group, a $C_{2-20}$-alkenyl group, a $C_{2-20}$-alkynyl group, a $C_{5-6}$-cycloalkyl group, a phenyl group and an O—$Si(CH_3)_3$ group, $R^e$ and $R^f$ are independently selected from the group consisting of H, a $C_{1-20}$-alkyl group, a $C_{2-20}$-alkenyl group, a $C_{2-20}$-alkynyl group, a $C_{5-8}$-cycloalkyl group, a $C_{6-14}$-aryl group, and a 5 to 14 membered heteroaryl group, the $C_{1-20}$-alkyl group, the $C_{2-20}$-alkenyl group and the $C_{2-20}$-alkynyl group optionally comprise one to five substituents selected from the group consisting of a $C_{5-6}$-cycloalkyl group, a $C_{6-10}$-aryl group, a 5 to 10 membered heteroaryl group, an $OR^g$ group, an $OC(O)$—$R^g$ group, a $C(O)$—$OR^g$ group, a $C(O)$—$R^g$ group, an $NR^gR^h$ group, an $NR^g$—$C(O)R^h$ group, a $C(O)$—$NR^gR^h$ group, an $N[C(O)R^g][C(O)R^h]$ group, an $SR^g$ group, a halogen, CN, and $NO_2$, the $C_{5-8}$-cycloalkyl group optionally comprises one to five substituents selected from the group consisting of a $C_{1-10}$-alkyl group, a $C_{2-10}$-alkenyl group, a $C_{2-10}$-alkynyl group, a $C_{5-6}$-cycloalkyl group, a $C_{6-10}$-aryl group, a 5 to 10 membered heteroaryl group, an $OR^g$ group, an $OC(O)$—$R^g$ group, a $C(O)$—OR group, a $C(O)$—R group, an $NR^gR^h$ group, an $NR^g$—$C(O)R^h$ group, a $C(O)$—$NR^gR^h$ group, an $N[C(O)R^g][C(O)R^h]$ group, an $SR^g$ group, a halogen, CN, and $NO_2$, the $C_{6-14}$-aryl group and the 5 to 14 membered heteroaryl group optionally comprise one to five substituents independently selected from the group consisting of a $C_{1-10}$-alkyl group, a $C_{2-10}$-alkenyl group, a $C_{2-10}$-alkynyl group, a $C_{5-6}$-cycloalkyl group, a $C_{6-10}$-aryl group, a 5 to 10 membered heteroaryl group, an $OR^g$ group, an OC(O)—R group, a $C(O)$—$OR^g$ group, a $C(O)$—R group, an $NR^gR^h$ group, an $NR^g$—$C(O)R^h$ group, a $C(O)$—$NR^gR^h$ group, an $N[C(O)R^g][C(O)R^h]$ group, an $SR^g$ group, a halogen, CN, and $NO_2$, $R^g$ and $R^h$ are independently selected from the group consisting of H, a $C_{1-10}$-alkyl group, a $C_{2-10}$-alkenyl group and a $C_{2-10}$-alkynyl group, the $C_{1-10}$-alkyl group, the $C_{2-10}$-alkenyl group and the $C_{2-10}$-alkynyl group optionally comprise one to five substituents selected from the group consisting of a halogen, CN and $NO_2$, each $R^{100}$ and $R^{101}$ is independently selected from the group consisting of H, a $C_{1-20}$-alkyl group, a $C_{2-20}$-alkenyl group, a $C_{2-20}$-alkynyl group, a $C_{5-8}$-cycloalkyl group, a $C_{6-14}$-aryl group, and a 5 to 14 membered heteroaryl group; or wherein $R^{100}$ and $R^{101}$, if attached to a same atom, together with the same atom, form a 5 to 12 membered ring system, the $C_{1-20}$-alkyl group, the $C_{2-20}$-alkenyl group and the $C_{2-20}$-alkynyl group optionally comprise one to five substituents selected from the group consisting of a $C_{5-6}$-cycloalkyl group, a $C_{6-10}$-aryl group, a 5 to 10 membered heteroaryl group, an $OR^q$ group, an OC(O)—$R^q$ group, a C(O)—$OR^q$ group, a C(O)—$R^q$ group, an $NR^qR^r$ group, an $NR^qC(O)R^r$ group, a C(O)—$NR^gR^r$ group, an $N[C(O)R^q][C(O)R^r]$ group, an $SR^q$ group, a halogen, CN, and $NO_2$, the $C_{5-8}$-cycloalkyl group optionally comprises one to five substituents selected from the group consisting of a $C_{1-10}$-alkyl group, a $C_{2-10}$-alkenyl group, a $C_{2-10}$-alkynyl group, a $C_{5-6}$-cycloalkyl group, a $C_{6-10}$-aryl group, a 5 to 10 membered heteroaryl group, an $OR^q$ group, an OC(O)—$R^q$ group, a C(O)—$OR^q$ group, a C(O)—$R^q$ group, an $NR^qR^r$ group, an $NR^q$—C(O)$R^r$ group, a C(O)—$NR^qR^r$ group, an $N[C(O)R^q][C(O)R^r]$ group, an $SR^q$ group, a halogen, CN, and $NO_2$, the $C_{6-14}$-aryl group and the 5 to 14 membered heteroaryl group optionally comprise one to five substituents independently selected from the group consisting of a $C_{1-10}$-alkyl group, a $C_{2-10}$-alkenyl group, a $C_{2-10}$-alkynyl group, a $C_{5-6}$-cycloalkyl group, a $C_{6-10}$-aryl group, a 5 to 10 membered heteroaryl group, an $OR^q$ group, an OC(O)—$R^g$ group, a C(O)—$OR^g$ group, a C(O)—$R^g$ group, an $NR^qR^r$ group, an $NR^q$—C(O)$R^r$ group, a C(O)—$NR^qR^r$ group, an $N[C(O)R^q][C(O)R^r]$ group, a $SR^q$ group, a halogen, CN, and $NO_2$, the 5 to 12 membered ring system optionally comprises one to five substituents selected from the group consisting of a $C_{1-10}$-alkyl group, a $C_{2-10}$-alkenyl group, a $C_{2-10}$-alkynyl group, a $C_{5-6}$-cycloalkyl group, a $C_{6-10}$-aryl group, a 5 to 10 membered heteroaryl group, an $OR^q$ group, an OC(O)—$R^g$ group, a C(O)—$OR^g$ group, a C(O)—$R^g$ group, an $NR^qR^r$ group, an $NR^q$—C(O)$R^r$ group, a C(O)—$NR^qR^r$ group, an $N[C(O)R^q][C(O)R^r]$ group, an $SR^q$ group, a halogen, CN, and $NO_2$, $R^q$ and $R^r$ are independently selected from the group consisting of H, a $C_{1-10}$alkyl group, a $C_{2-10}$-alkenyl group and a $C_{2-10}$-alkynyl group, the $C_{1-10}$-alkyl group, the $C_{2-10}$-alkenyl group and the $C_{2-10}$-alkynyl group optionally comprise one to five substituents selected from the group consisting of a halogen, CN and $NO_2$, and m is in a range from 3 to 1000.

6. The polymer of claim 5, consisting of units haing a structure of formula 4'

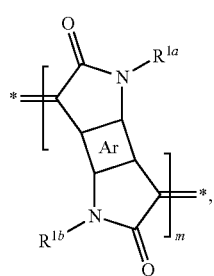

$R^{1b}$ is independently defined as $R^{1a}$, and m is in a range from 3 to 1000.

7. A process for preparing the polymer of claim 1, the process comprising condensing a tetraone A and a dione B:

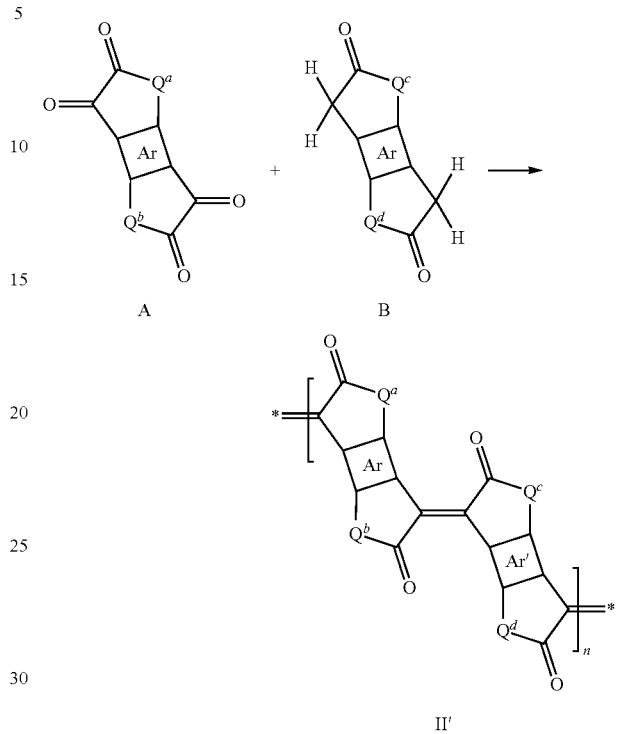

wherein $Q^a$, $Q^b$, $Q^c$, $Q^d$, Ar and Ar' are as defined in claim 1.

8. The process of claim 7, wherein:

$Q^a$ and $Q^b$ are an $NR^1$ group, and $Q^c$ and $Q^d$ are O or an $NR^1$ group.

9. A process for preparing the polymer of claim 5, the process comprising homopolymerizing a tetraone A:

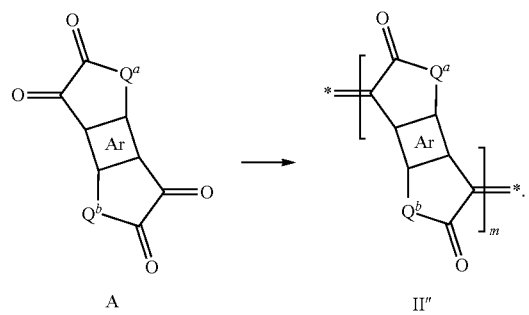

10. An electronic device comprising the polymer of claim 1.

11. The electronic device of claim 10, wherein the electronic device is an organic field effect transistor.

12. A polymer consisting of units having a formula selected from P1 to P11:

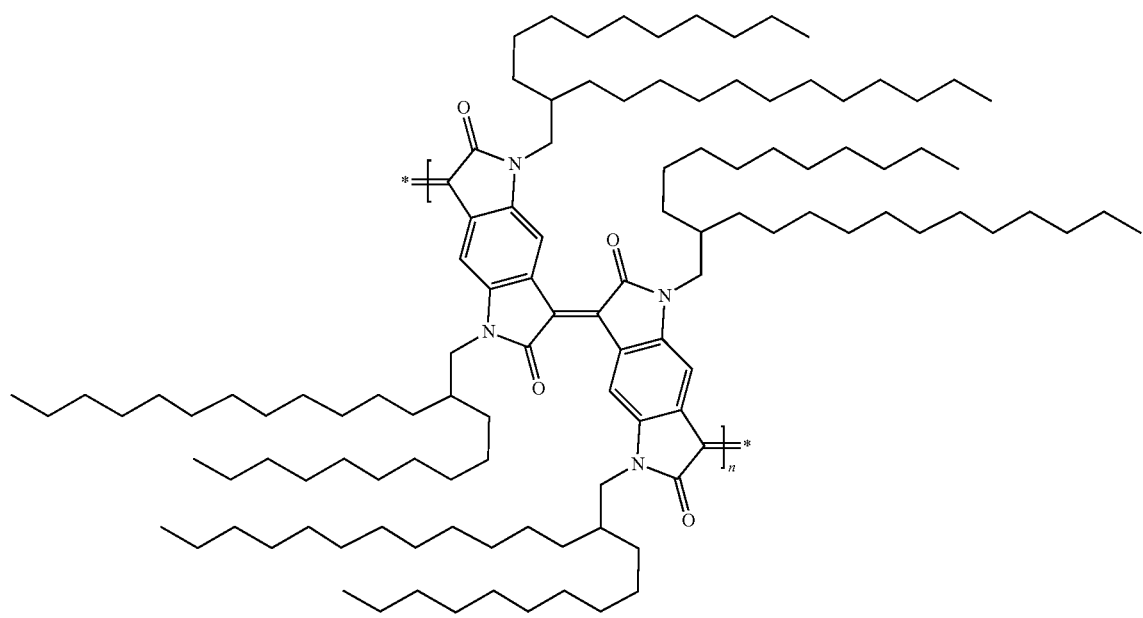
P1
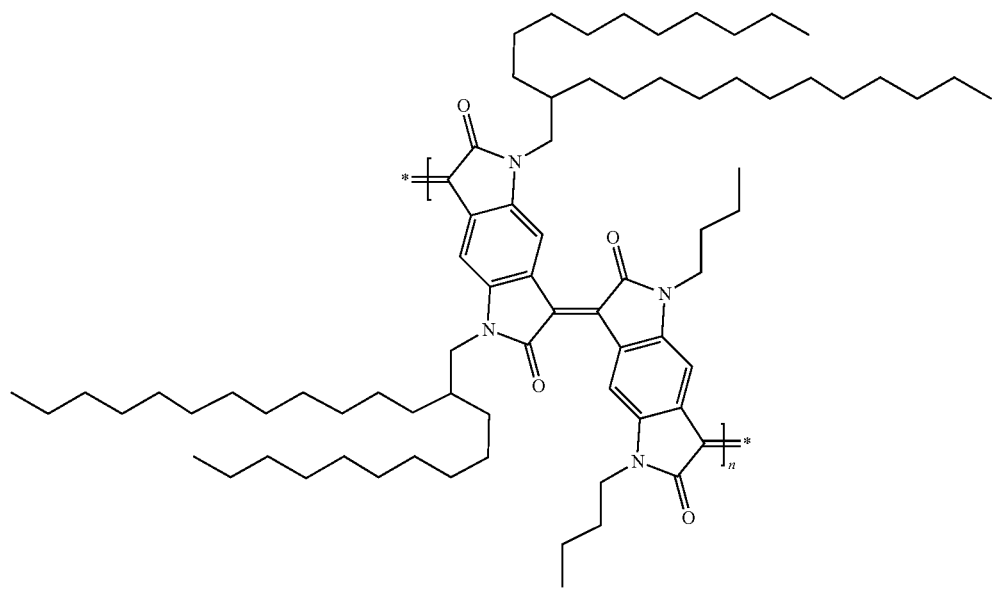
P2

-continued
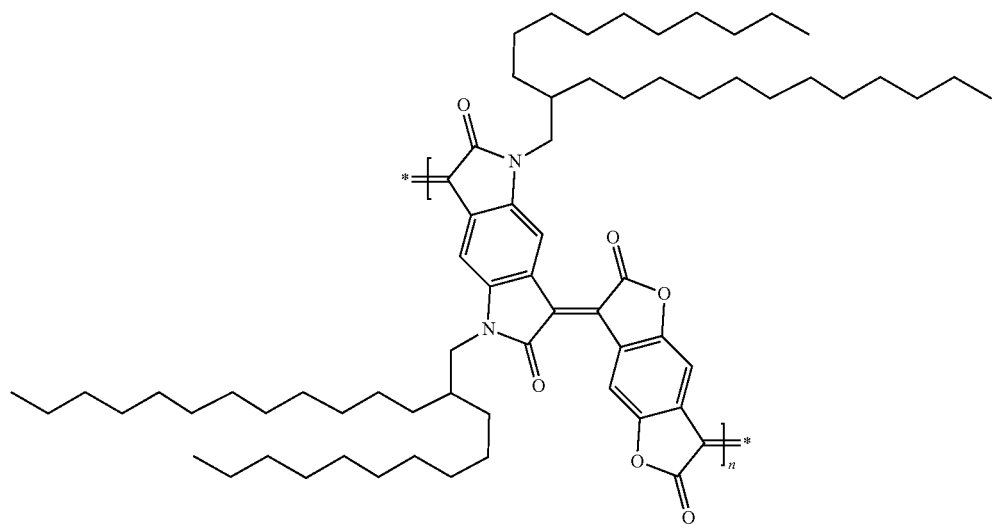
P3
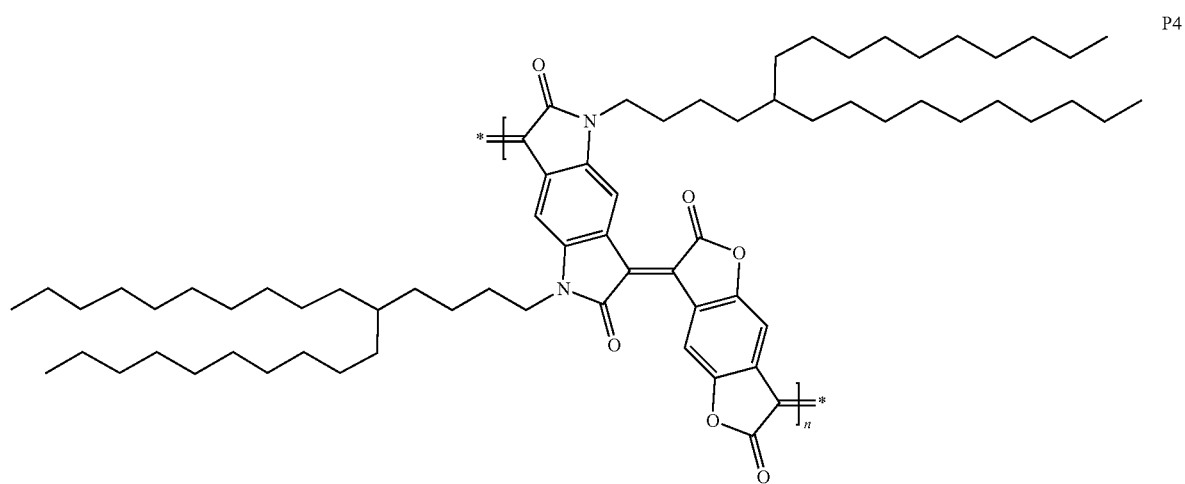
P4
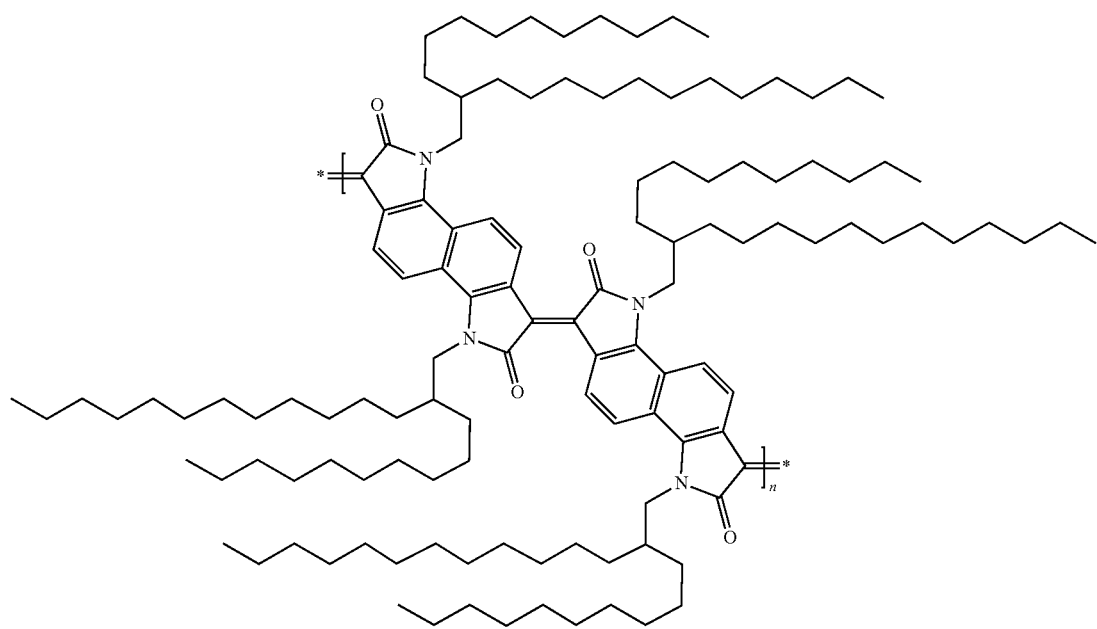
P5

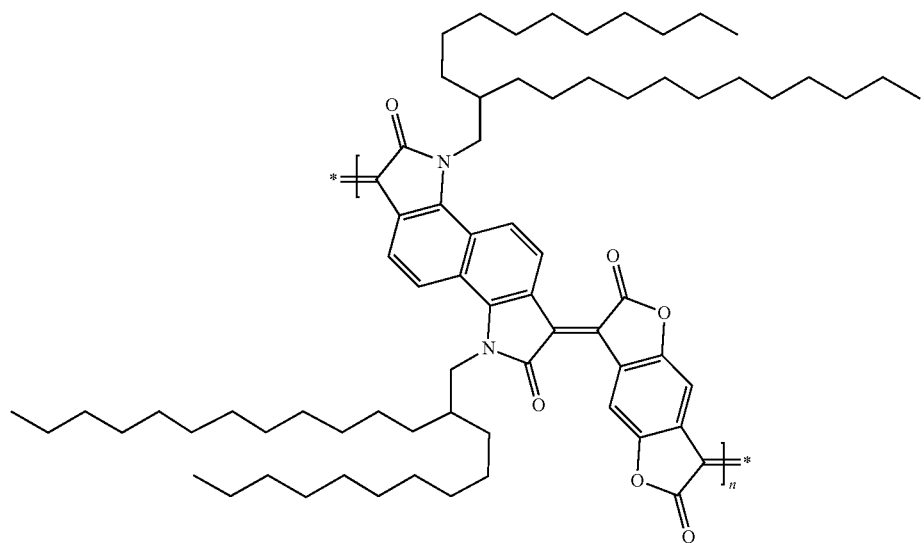
P6
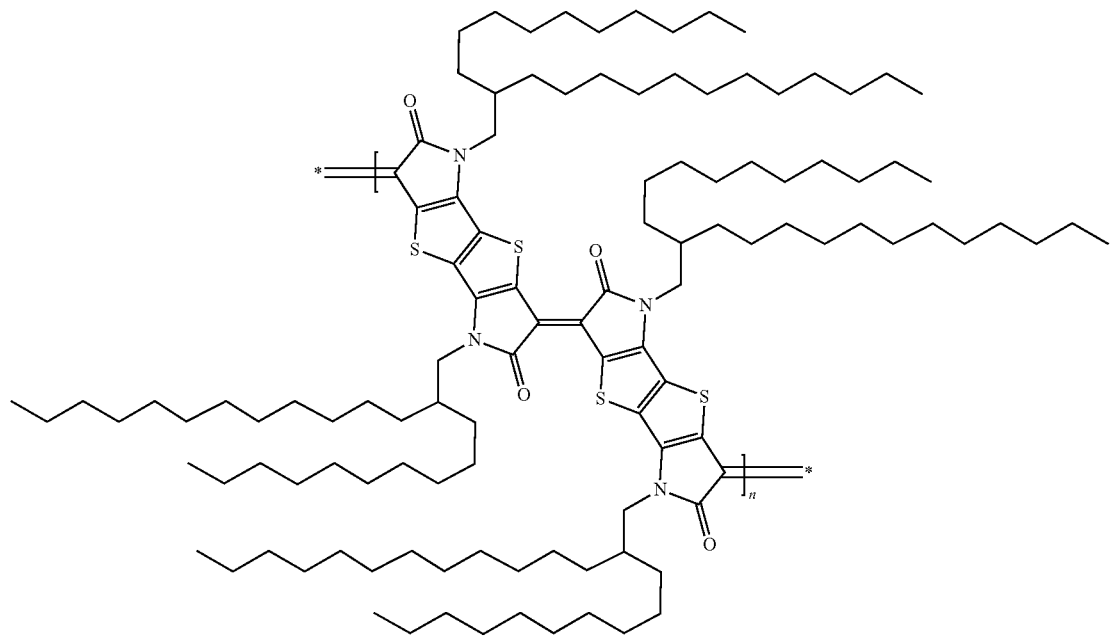
P7

-continued
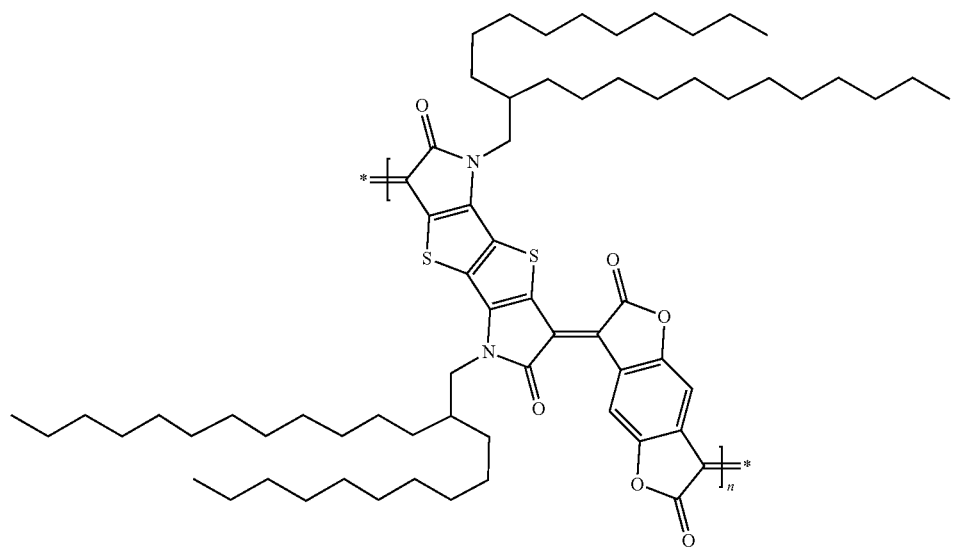
P8
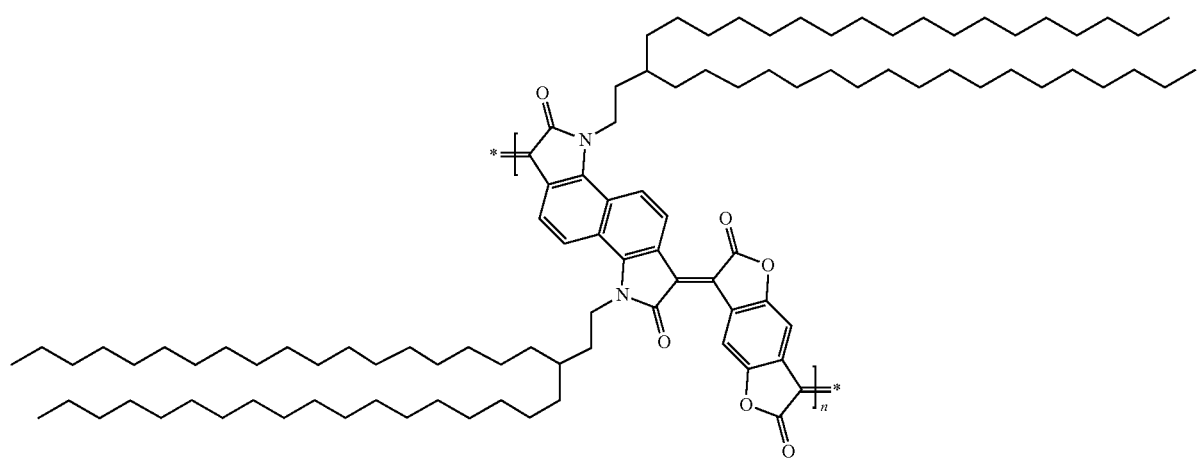
P9
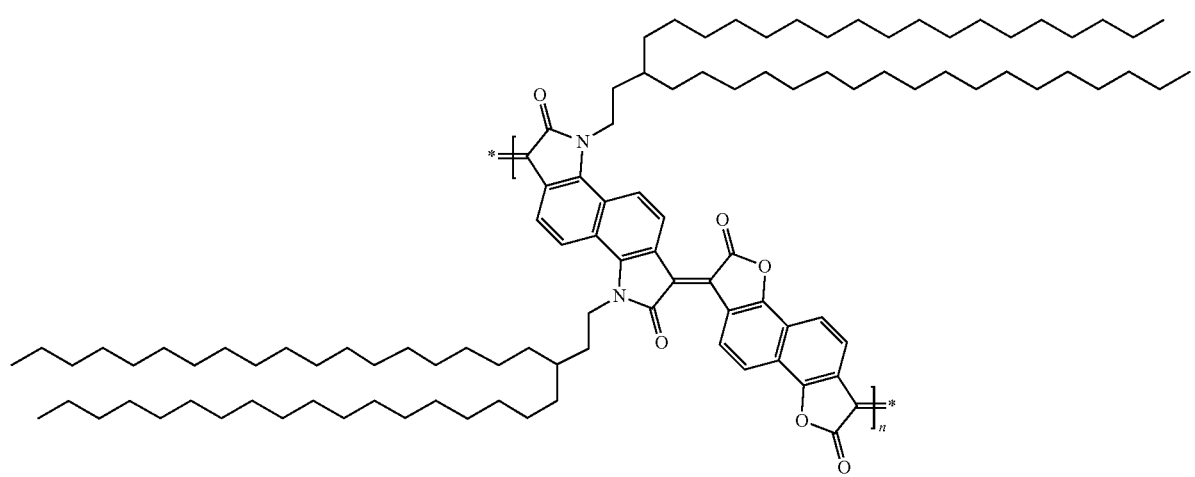
P10

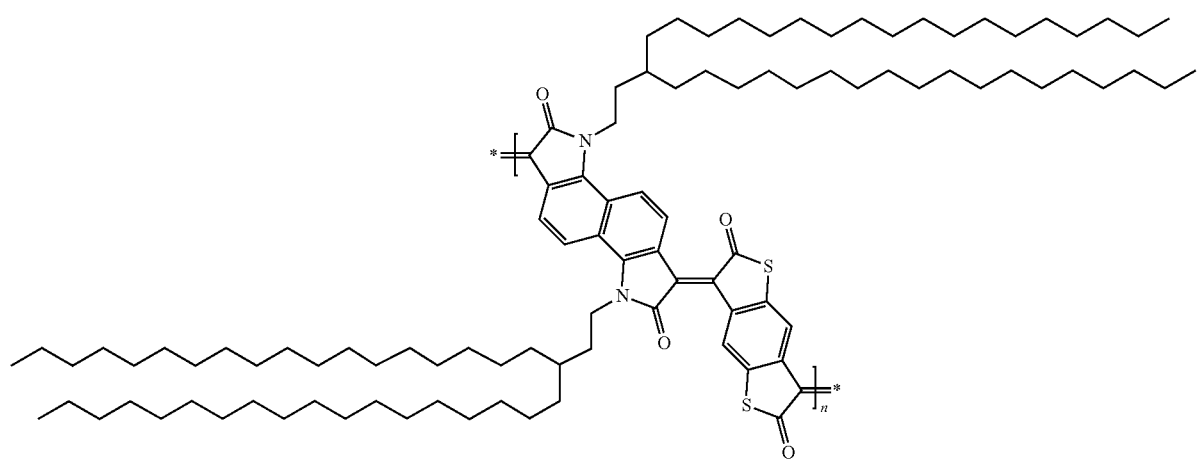
wherein:
n is an integer from 3 to 1000.
13. polymer consisting of units having a formula selected from P12 to P14:
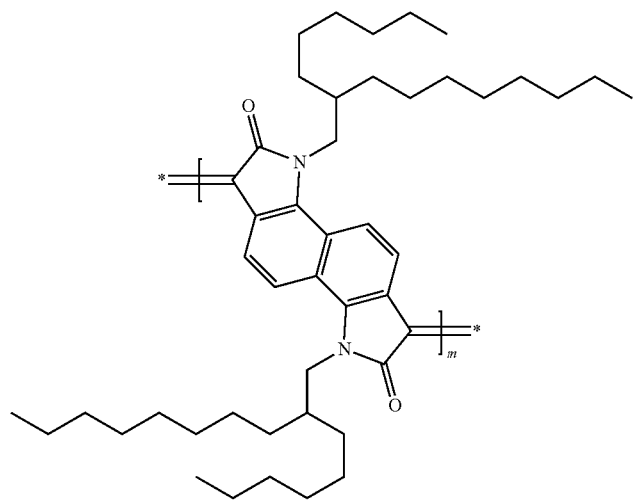
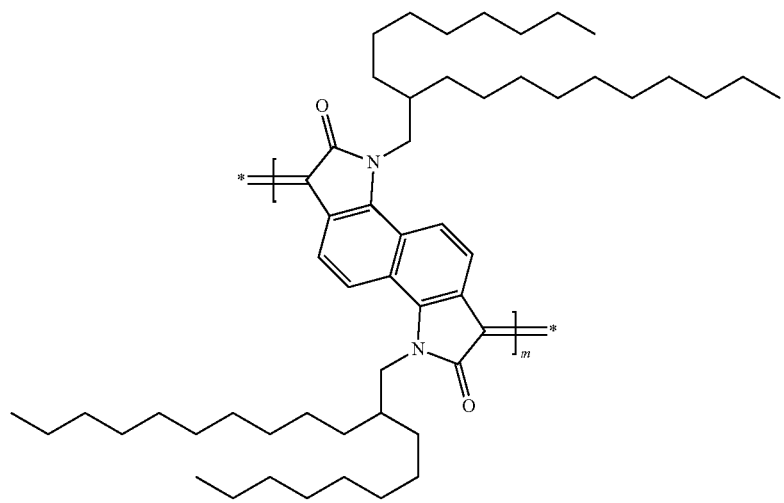

P14
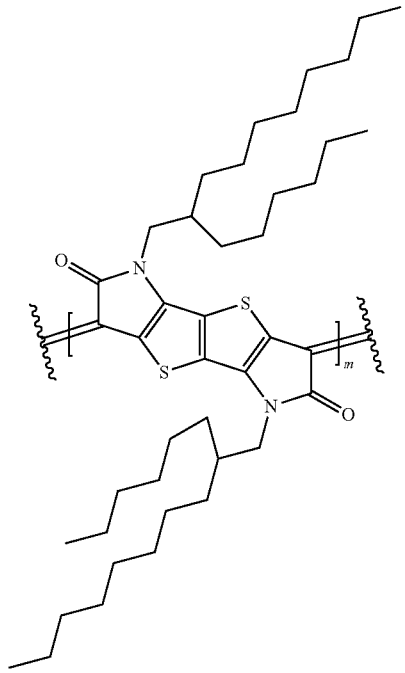
wherein:
m is an integer from 3 to 1000.